United States Patent
Zomer et al.

(10) Patent No.: US 11,576,924 B2
(45) Date of Patent: Feb. 14, 2023

(54) COMPOUNDS FOR THE PREVENTION AND TREATMENT OF DISEASES AND THE USE THEREOF

(71) Applicant: Galectin Sciences, LLC, Norcross, GA (US)

(72) Inventors: Eliezer Zomer, Newton, MA (US); Peter G. Traber, Alpharetta, GA (US); Raphael Nir, Needham, MA (US); Sharon Shechter, Andover, MA (US); Joseph M. Johnson, Arlington, MA (US); Ryan George, Framingham, MA (US)

(73) Assignee: GALECTIN SCIENCES, LLC, Norcross, GA (US)

( * ) Notice: Subject to any disclaimer, the term of this patent is extended or adjusted under 35 U.S.C. 154(b) by 0 days.

(21) Appl. No.: 16/611,609

(22) PCT Filed: May 11, 2018

(86) PCT No.: PCT/US2018/032349
§ 371 (c)(1),
(2) Date: Nov. 7, 2019

(87) PCT Pub. No.: WO2018/209255
PCT Pub. Date: Nov. 15, 2018

(65) Prior Publication Data
US 2020/0155586 A1 May 21, 2020

Related U.S. Application Data

(60) Provisional application No. 62/505,544, filed on May 12, 2017.

(51) Int. Cl.
| | | |
|---|---|---|
| *A61K 31/7056* | (2006.01) | |
| *A61P 1/16* | (2006.01) | |
| *A61P 9/00* | (2006.01) | |
| *A61P 13/12* | (2006.01) | |
| *A61K 45/06* | (2006.01) | |
| *C07H 17/00* | (2006.01) | |
| *C07H 17/02* | (2006.01) | |
| *C07H 99/00* | (2006.01) | |

(52) U.S. Cl.
CPC .......... *A61K 31/7056* (2013.01); *A61K 45/06* (2013.01); *A61P 1/16* (2018.01); *A61P 9/00* (2018.01); *A61P 13/12* (2018.01); *C07H 17/00* (2013.01); *C07H 17/02* (2013.01); *C07H 99/00* (2013.01)

(58) Field of Classification Search
CPC .... A61K 31/7056; A61K 45/06; C07H 17/02; C07H 17/00; C07H 99/00; A61P 9/00; A61P 1/16; A61P 13/12
USPC ......................................................... 514/43
See application file for complete search history.

(56) References Cited

U.S. PATENT DOCUMENTS

| | | | |
|---|---|---|---|
| 5,070,190 A | * | 12/1991 | Lockhoff ............... C07H 15/12 536/29.1 |
| 6,680,306 B2 | | 1/2004 | Chang et al. |
| 7,230,096 B2 | | 6/2007 | Nilsson et al. |
| 7,638,623 B2 | | 12/2009 | Nilsson et al. |
| 7,700,763 B2 | | 4/2010 | Leffler et al. |
| 8,672,857 B2 | | 3/2014 | Muntendam |
| 8,697,862 B2 | | 4/2014 | Nilsson et al. |
| 8,703,720 B2 | | 4/2014 | Leffler et al. |
| 8,828,971 B2 | | 9/2014 | Traber et al. |
| 9,243,021 B2 | | 1/2016 | Sethi et al. |
| 2008/0213297 A1 | | 9/2008 | Finn et al. |
| 2011/0294755 A1 | | 12/2011 | Eliaz |
| 2013/0171151 A1 | | 7/2013 | Traber et al. |
| 2014/0336146 A1 | | 11/2014 | Nillson et al. |
| 2015/0320782 A1 | | 11/2015 | Panjwani et al. |
| 2018/0221400 A1 | | 8/2018 | Gelovani et al. |
| 2019/0367552 A1 | | 12/2019 | Schechter et al. |
| 2020/0061095 A1 | | 2/2020 | Traber et al. |

FOREIGN PATENT DOCUMENTS

| | | |
|---|---|---|
| CA | 2794066 A1 | 4/2014 |
| WO | 1998028318 A1 | 7/1998 |
| WO | 2005113568 A1 | 12/2005 |
| WO | 20050113569 A1 | 12/2005 |
| WO | 2008060617 A2 | 5/2008 |
| WO | 2010126435 A1 | 11/2010 |
| WO | 2011095772 A2 | 8/2011 |
| WO | 2013040316 A1 | 3/2013 |
| WO | 2013101314 A1 | 7/2013 |
| WO | 2014067986 A1 | 5/2014 |
| WO | 2014078655 A1 | 5/2014 |
| WO | 2015138438 A1 | 9/2015 |
| WO | 2015155207 A1 | 10/2015 |
| WO | 2016005311 A1 | 1/2016 |
| WO | 2016120403 A1 | 8/2016 |
| WO | 2017080973 A1 | 5/2017 |
| WO | 2017152048 A1 | 9/2017 |

OTHER PUBLICATIONS

Schierholt et al. (Eur. J. Org. Chem. 2009, 3783-3789).*
Ahn, Sang Joon et al., "Regulation of Melanin Synthesis by Selenium-Containing Carbohydrates", Chem. Pharm. Bulletin, vol. 54(3), pp. 281-286, Mar. 2006.
Blanchard, et al. "Galectin-3 Inhibitors: A Patent Review (2008-Present)" Expert Opinion on Therapeutic Patents, vol. 24, No. 10, pp. 1053-1065, Aug. 9, 2014.
Kumar, et al. 'Convenient syntheses of 1,2-trans selenoglycosides using isoselenuronium salts as glycosylselenenyl transfer reagents', Carbohydrate Research, vol. 360, pp. 8-18, p. 9, col. 1, para 3, Scheme 1; p. 10, Table 1; p. 10, col. 2, para 2 to p. 11, col. 1, para 1, Oct. 2012.
Li, et al. "Hematopoietic-Derived Galectin-3 Causes Cellular and Systemic Insulin Resistance" Cell, vol. 167, pp. 973-984, Nov. 3, 2016.

(Continued)

*Primary Examiner* — Shaojia A Jiang
*Assistant Examiner* — Michael C Henry
(74) *Attorney, Agent, or Firm* — Greenberg Traurig, LLP

(57) ABSTRACT

Aspects of the invention relate to novel synthetic compounds having binding affinity with galectin proteins.

4 Claims, 35 Drawing Sheets

(56) References Cited

OTHER PUBLICATIONS

Pusuroglu, et al. "Galectin-3 is Associated with Coronary Plaque Burden and Obstructive Sleep Apnoea Syndrome Severity" Kardiologia Polska, vol. 75, No. 4, pp. 351-359, Dec. 27, 2016.
Sabine, et al., "Thio- and selenoglycosides as ligands for biomedically relevant lectins: Valency-activity correlations for benzene-based dithiogalactoside clusters and first assessment for (di)selenodigalactosides11", Bioorganic & Medicinal Chemistry Letters, vol. 25, No. 4, pp. 931-935, Feb. 1, 2015.
Salameh, et al., "1H-1,2,3-Triazol-1-yl thiodigalactoside derivatives as high affinity galectin-3 inhibitors", BioOrganic & Medicinal Chemistry: A Tetrahedron Publication for the Rapid Dissemination of Full Original Research Papers and Critical Reviews on Biomolecular Chemistry and Related Disciplines, Elsevier, NL, vol. 18, No. 14, pp. 5367-5378, Jul. 15, 2010.
Swarts, et al. "Chemical Synthesis of Glycosylphosphatidylinositol Anchors", Advances in Carbohydrate Chemistry and Biochemistry, vol. 67, pp. 137-219, Jul. 13, 2012.
van Hattum et al., "Tuning the Preference of Thiodigalactoside- and Lactosamine-Based Ligands to Galectin-3 over Galectin-1", Journal of Medicinal Chemistry, vol. 56, pp. 1350-1354, Jan. 1, 2013.
van Scherpenzeel et al., "Synthesis and Evaluation of New Thiodigalactoside-Based Chemical Probes to Label Galectin-3", ChemBioChem, vol. 10, pp. 1724-1733, 2009.
Yilmaz et al. "Increased levels of galectin-3 were associated with prediabetes and diabetes: New risk factor?" Journal of Endocrinol Investigation, pp. 1-8, Dec. 12, 2014.
Pubchem CID 102382435—Create Date Dec. 26, 2015 (Dec. 26, 2015) Date Accessed: Sep. 5, 2018 (Sep. 5, 2018); p. 3.
Tejler "Synthetic Galectin Inhibitors Selective O-galactosyl aldoximes, multivalent lactosides and galactose-mimicking mannosides" Lund University. Jan. 1, 2006 (Jan. 1, 2006) p. 1-70; p. 18, scheme 1.
International Search Report in International Application No. PCT/US2018/032349 dated Sep. 21, 2018.
Wang et al., "Design of Glycosyltransferase Inhibitors: Pyridine as a Pyrophosphate Surrogate," Chemistyr—A European Journal, Sep. 23, 2013, vol. 19, No. 45, pp. 15346-15357.
Murphy et al., "Development of Carbohydrate-Based Scaffolds for Restricted Presentation of Recognition Groups. Extension to Divalent Ligands and Implications for the Structure of Dimerized Receptors," The Journal of Organic Chemistry, Jun. 18, 2003, vol. 68, No. 14, pp. 5692-5704.

\* cited by examiner

Galectin-3 Carbohydrate Recognition Domain (CRD)-- 3 potential sites of interaction The Carbohydrate recognition Domain (CRD) location in the Galectin-3 C-terminal Galectin-3 CRD site vicinity - potential cooperative aminoacids

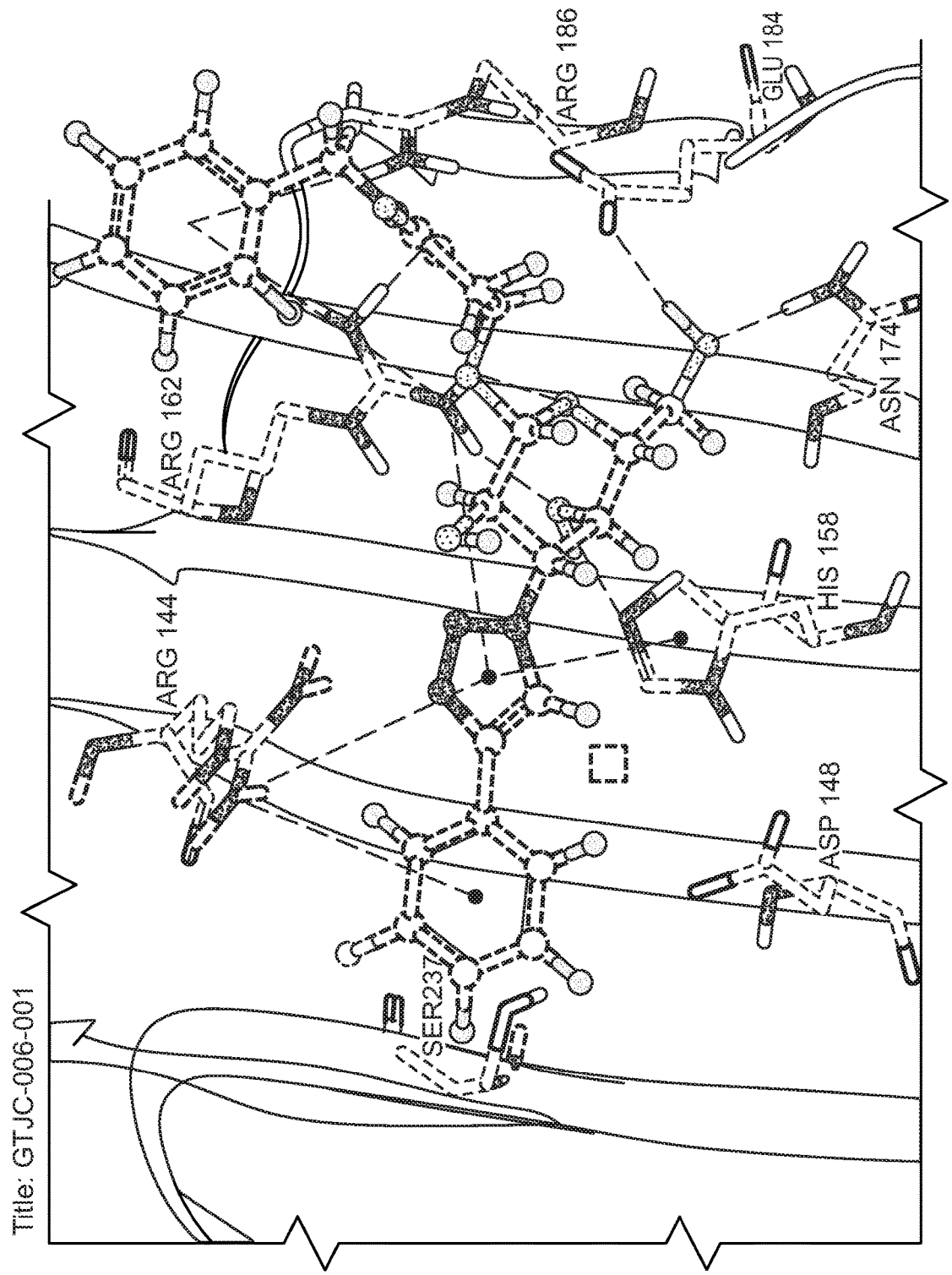

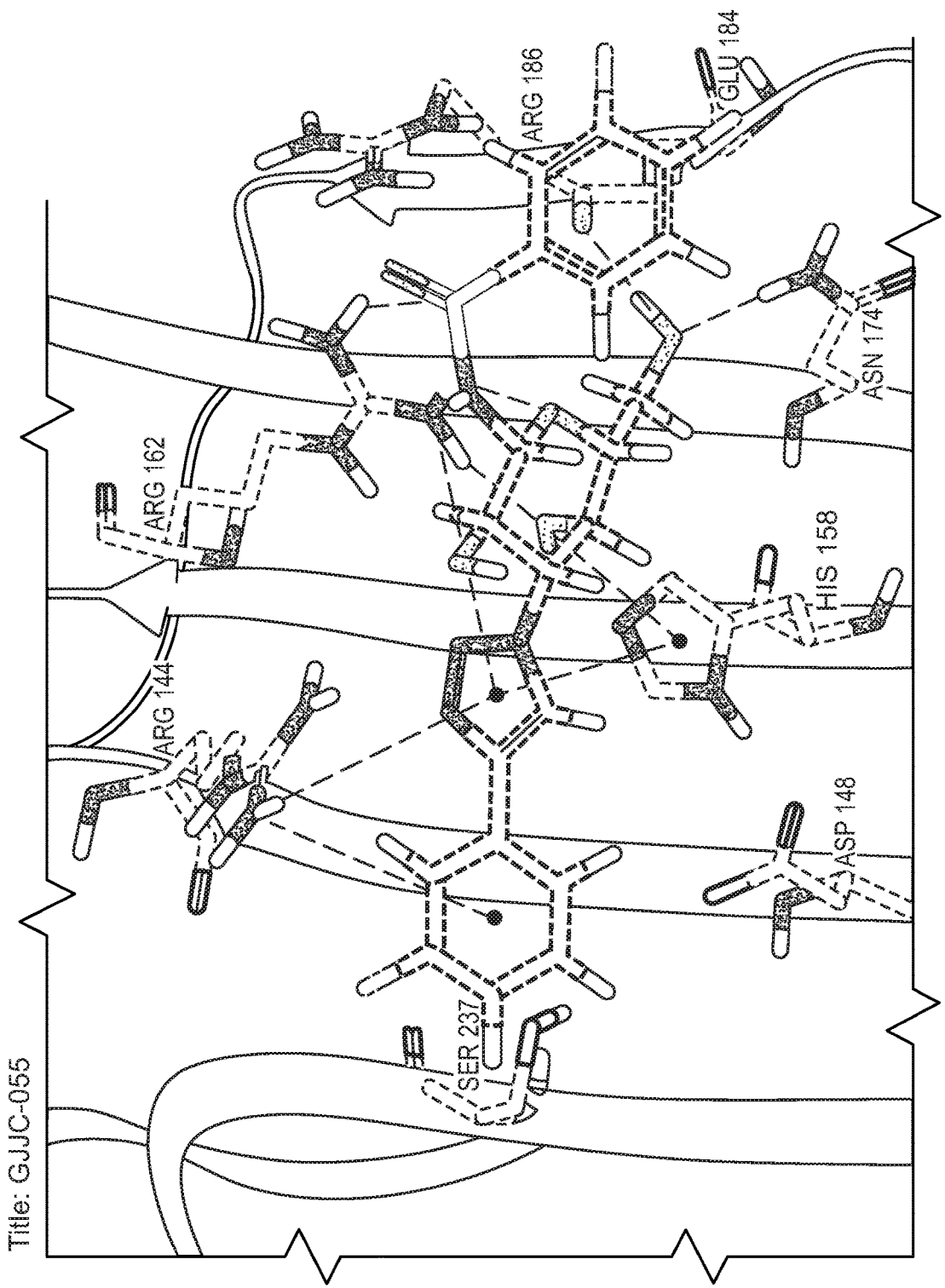
Figure 3B  Predicted docking pose of GalactoAmide linked compound
Title: GJJC-055

Synthesis of GalactoAmide and GalactoSulfonamide Compositions:
*Synthesis of Intermediate compound:*
Scheme 1

Scheme 2

*Compounds: GTJC-013 series:*

Scheme 3 – *Compound: G623*

Scheme 4 – *Compound: G620*

Figure 4B Cont.

*Compound: G649*

2-(3,4-difluorophenyl)-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylacetamide (GTJC-013-37)

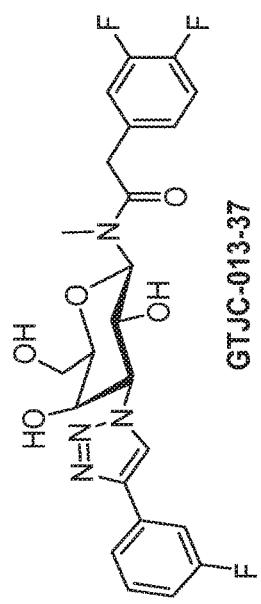

GTJC-013-37

Synthesized following the standard procedure used for GTJC-013-03 or GTJC-013-04

*Compound: G651*

2-(3,4-difluorophenoxy)-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylacetamide (GTJC-013-38)

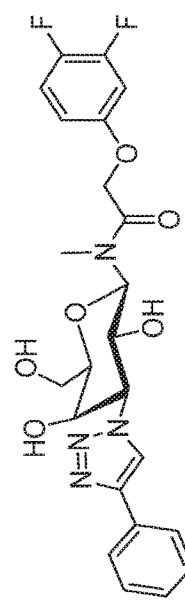

GTJC-013-38

Synthesized following the standard procedure used for GTJC-013-03 or GTJC-013-04

Figure 4B Cont.

*Compound: G652*

3-(3,4-difluorophenyl)-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylpropanamide (GTJC-013-41):

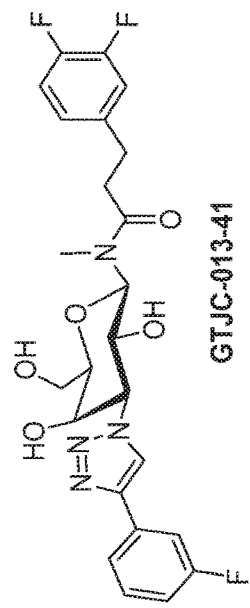

GTJC-013-41

Synthesized following the standard procedure used for GTJC-013-03 or GTJC-013-04

*Compound: G658*

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-3,4-dimethoxy-N-methylbenzamide (GTJC-013-46-1):

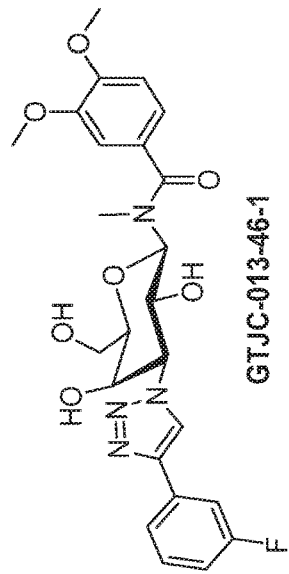

GTJC-013-46-1

Synthesized following the standard procedure used for GTJC-013-03 or GTJC-013-04

Figure 4B Cont.

*Compound: G655*
N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-3,4-dihydroxy-N-methylbenzamide (GTJC-013-46):

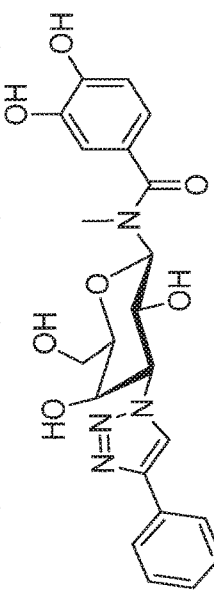

GTJC-013-46

Synthesized following the standard procedure used for GTJC-013-23

*Compound: G642*
N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methyl-3-(trifluoromethoxy)benzamide (GTJC-013-45)

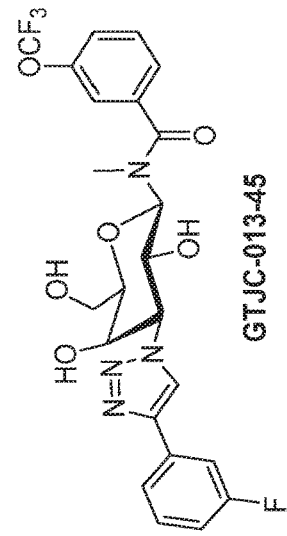

GTJC-013-45

Synthesized following the standard procedure used for GTJC-013-03 or GTJC-013-04

Figure 4B Cont.

*Compound: G650*

Synthesis of 2,3,4,5,6-pentafluoro-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylbenzamide (GTJC-013-47)

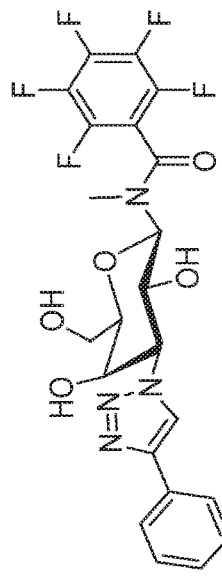

GTJC-013-47

Synthesized following the standard procedure used for GTJC-013-03 or GTJC-013-04

*Compound: G629*

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-1-methoxy-N-methyl-2-naphthamide (GTJC-013-22)

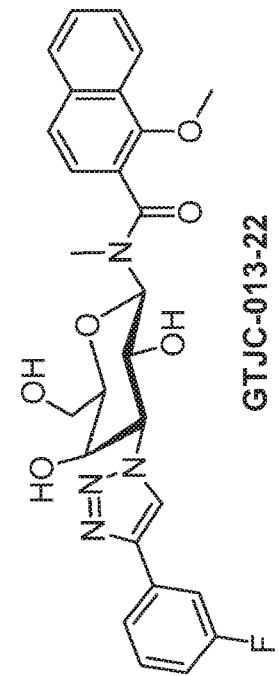

GTJC-013-22

Synthesized following the standard procedure used for GTJC-013-03 or GTJC-013-04

Figure 4C
*Compound: G635*
Scheme 5
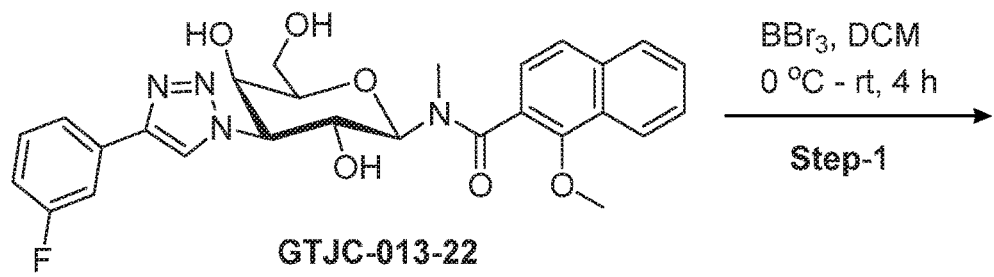
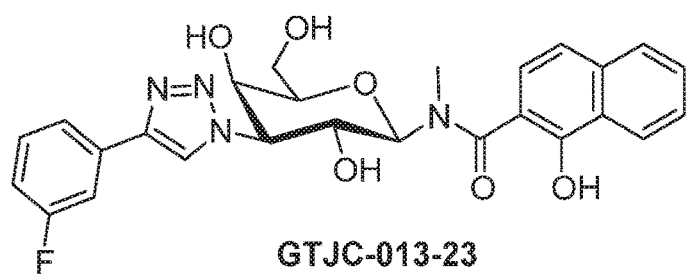
N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-1-hydroxy-N-methyl-2-naphthamide (GTJC-013-23):

*Compound: G637*

Scheme 6

N1,N4-bis((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N1,N4-dimethylterephthalamide (GTJC-013-12):

*Compound: G638*
Scheme 7

Figure 4F
*Compound: G633*
Scheme 8
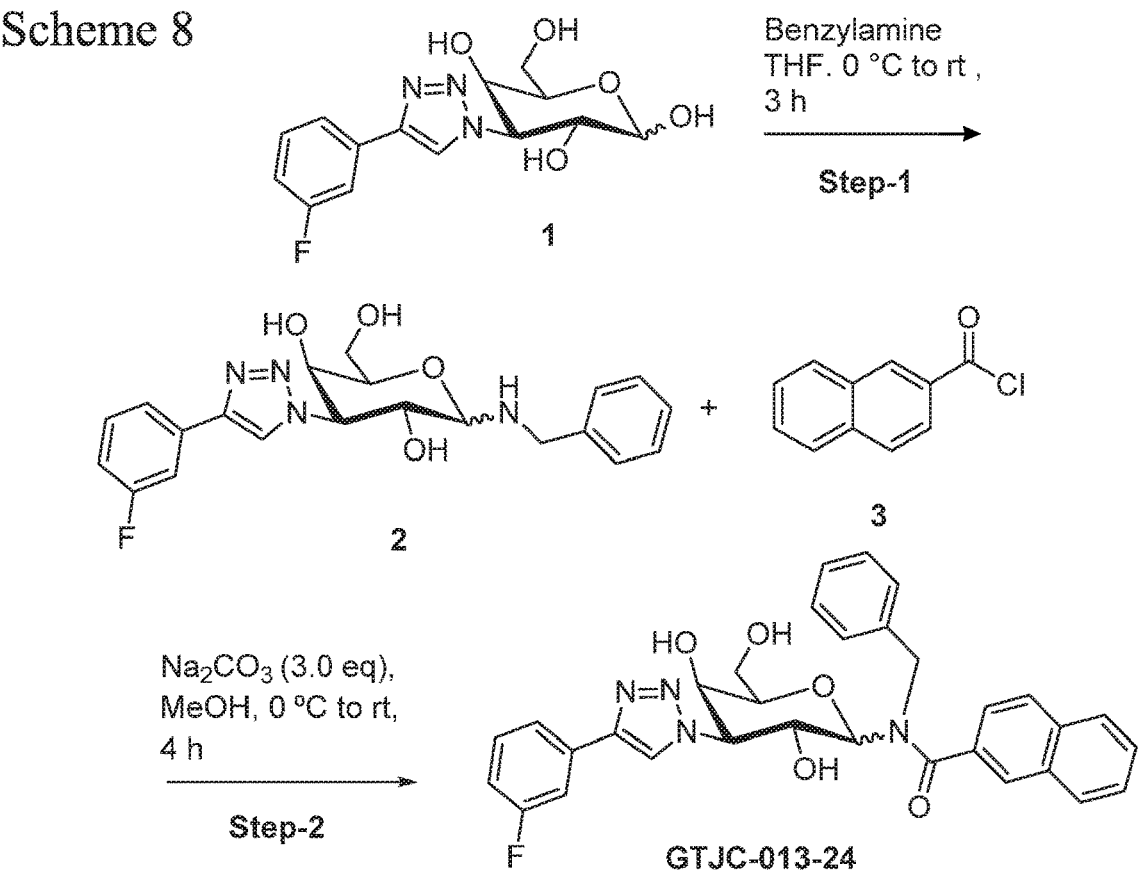
*Compound: G639*
N-benzyl-N-((2R,3R,4S,5R,6R)-4-(4-(3-fluorophenyl)-
1H-1,2,3-triazol-1-yl)-3,5-dihydroxy-6-
(hydroxymethyl)tetrahydro-2H-pyran-2-yl)
benzamide (GTJC-013-20)
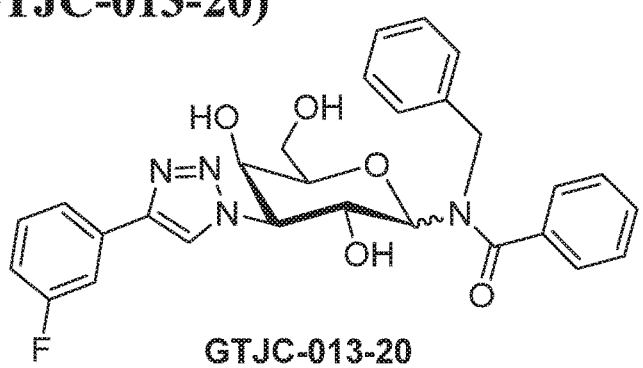
Synthesized following the standard procedure used for
GTJC-013-24

*Compound: G643*

Scheme 9

*Compound: G653*
Scheme 10

Figure 4I
*Compound: G630*
Scheme 11
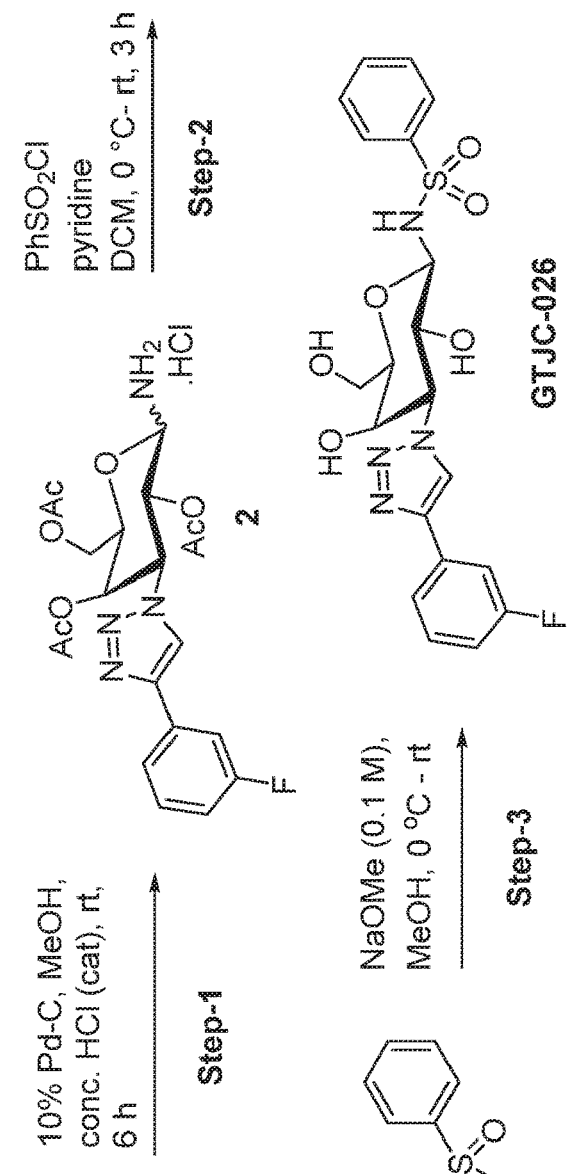
*Compound: G666*
N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)benzenesulfonamide (GTJC-055):
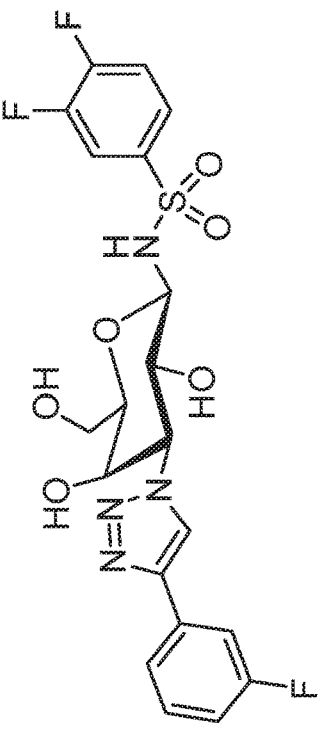

*Compound: G632*
Scheme 12

Compound: G670
Scheme 13

ELISA MAb Anti-Galectin-3 Assay Format - Galectin 3 Specific binding Assay

ELISA Integrin-Galectin-3 Inhibition Assay Format - Physiological assay

FRET ASSAY Binding Format (Fluorescence Resonance Energy Transfer)

FLUORESCENT POLARIZATION ASSAY FORMAT - CRD binding specific test

Correlation between the ELISA MAb and the ELISA Integrin aMB2 assays

Figure 7B

Example of Compounds IC50 Inhibition by the Integrin aMB2-Gal-3 and the MAb-Gal-3 ELISA assays

| List by GTJC Synthesis code | ID | Integrin-Gal-3 | MAb-Gal-3 |
|---|---|---|---|
| GTJC-013 | G610 | 8.8 | 13.48 |
| GTJC-014 | G611 | 9.8 | 14.28 |
| GTJC-013-10 | G628 | 0.99 | 4.06 |
| GTJC-013-12 | G637 | 7.9 | 5.2 |
| GTJC-013-20 (2 Deriv.) | G639 | 19.87 | 17.31 |
| GTJC-013-20 (2 Deriv.) | G640 | 46.24 | 53.8 |
| GTJC-013-27 | G641 | 36.46 | 24.43 |
| GTJC-013-45 | G642 | 10.82 | 9.64 |
| GTJC-013-42 | G643 | 12.6 | 10.1 |
| GTJC-006-001(3 Deriv.) | G646 | 5.98 | 6.45 |
| GTJC-013-16 | G647 | 6.02 | 10.19 |
| GTJC-013-21 | G648 | 39.65 | 43.15 |
| GTJC-013-37 | G649 | 26.08 | 31.95 |
| GTJC-013-41 | G652 | 38.23 | 36.4 |
| GTJC-013-43 | G653 | 17.02 | 19.14 |
| GTJC-013-43-001 | G654 | 9.33 | 11.38 |
| GTJC-013-46 | G655 | 6.14 | 5.61 |

Figure 8A

Example of compounds hinder Fluorescent Polarization - a CRD specific assay

| | |
|---|---|
| G666 - (GTJC-055) a sulfonamide derivative | FP IC50 = 5.48 ug/mL |
| [Dose-response curve: mP vs Inhibitor Concentration (ug/ml), ranging 0.1 to 100] | [Structure of G666] G666 -IC50 = 5.48ug/mL |
| G611 - (GTJC-014) Hydrazine- derivative | FP IC50 = 35 |
| Week FP | [Structure of hydrazine derivative] |
| G647 - (GTJC-013-16) a Carboamide derivative | FP = 10.5 ug/mL |
| [Dose-response curve: IC50 ~ 10.9ug/mL, G647, Series1] | [Structure of G662] G662 -IC50 = 9.3ug/mL |

Inhibition of MCP-1 Secreted by Inflammatory Macrophages (LPS Stressed THP-1 cells)

COMPOUNDS FOR THE PREVENTION AND TREATMENT OF DISEASES AND THE USE THEREOF

RELATED APPLICATION(S)

This application is a U.S. national phase application under 35 U.S.C. 371 of PCT International Application No. PCT/US2018/032349, filed on May 11, 2018, which claims the benefit of and priority to U.S. Provisional Application Ser. No. 62/505,544, filed May 12, 2017, the entire disclosure of each of which is incorporated herein by reference in its entirety.

FIELD OF THE INVENTION

Aspects of the invention relate to compounds, pharmaceutical compositions, methods for the manufacturing of compounds and methods for treatment of various disorders mediated at least in part by one or more galactose binding proteins also referred to as Galectins.

BACKGROUND OF THE INVENTION

Galectins are a family of S-type lectins that bind beta-galactose-containing glycoconjugates. To date, fifteen mammalian galectins have been isolated. Galectins regulate different biological processes such as cell adhesion, regulation of growth, apoptosis, inflammation, fibrogenesis, tumor development and progression. Galectins have been shown to be involved in inflammation, fibrosis formation, cell adhesion, cell proliferation, metastasis formation, angiogenesis, cancer and immunosuppression.

SUMMARY OF THE INVENTION

Aspects of the invention relate to compounds or compositions comprising a compound in an acceptable pharmaceutical carrier for parenteral or enteral administration, for use in therapeutic formulations. In some embodiments, the composition can be administered parenterally via an intravenous, subcutaneous, dermal or oral route.

Aspects of the invention relate to compounds or compositions for the treatment of various disorders in which lectin proteins play a role in the pathogenesis, including but not limited to, chronic inflammatory diseases, fibrotic diseases, and cancer. In some embodiments, the compound is capable of mimicking glycoprotein interactions with lectins or galectin proteins which are known to modulate the pathophysiological pathways leading to inflammation, fibrogenesis, angiogenesis, cancer progression and metastasis.

According to some aspects of the invention, the compounds comprise pyranosyl and/or furanosyl structures conjugated through an A-M spacer of at least 2 atoms comprising an amide —N(—Ra)—C(=O)—, sulfonamide —N(—H)—S(=O2)—, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, Hydrazide —N(—H)—N(—H)— and/or an amino acid.

In some embodiments, the A-M spacer comprises of an amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, carbohydrazide —C(=O)—NH—NH—, sulfonohydrazide —S(=O)2-NH—NH—, or a phosphonic dihydrazide —P(=O)(—NH—NH2)(NH—NH—) spacer or any combination of the foregoing.

In some embodiments, the spacer is linked to the anomeric carbon of the pyranosyl and/or furanosyl structure.

In some embodiments, the compound comprises organic substituents. In some embodiments, specific aromatic substitutions can be linked to the galactose core or the "AM" linker of the anomeric carbon of the pyranosyl and/or furanosyl structures. Such aromatic substitutions can enhance the interaction of the compound with amino acid residues (e.g. Arginine, Tryptophan, Histidine, Glutamic acid etc. . . . ) composing the carbohydrate-recognition-domains (CRD) of the lectins or with amino acid residues in the CRD neighborhood and thus strengthen the association and binding specificity.

In some embodiments, the organic substituents comprise monosaccharides, disaccharides, oligosaccharides or a heteroglycoside such as iminosugar or thiosugar carbohydrates.

In some embodiments, the compound is a symmetric digalactoside, wherein the two galactosides are bound by an A-M spacer. Yet in other embodiments, the compound can be comprised of asymmetric carbohydrates. For example, each of the galactoside can have different aromatic or aliphatic substitutions or heterotatoms derivatives of the galactose where the C5 oxygen is replaced with S (5-Thio-D-galactose) or N (5-imino-D-galactose).

Without being bound to the theory, it is believed that A-M spacer render the compounds metabolically stable while maintaining the chemical, physical and allosteric characteristics for specific interaction with lectins or galectins known to recognize carbohydrates. In some embodiments, the GalactoAmide and the GalactoSulfonamide of the invention are metabolically more stable than compounds having an O-glycosidic bond.

Aspects of the invention relate to a compound of formula 1 or a pharmaceutically acceptable salt or solvate thereof:

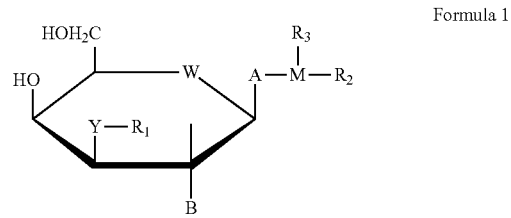

Formula 1 wherein A is selected from the group consisting of NRa, CRb, PRc, and amino acid, wherein M is selected from the group consisting of NRa, CRb, PRc, ORd, SRe amino acid, and hydrophobic hydrocarbons derivatives including heterocyclic substitutions of 3 or more atoms, wherein Ra is selected from the group consisting of H, H2, CH3, COOH, NH2, COMe, halogen and combinations thereof, wherein Rb is selected from the group consisting of H, H2, O, OH, CH3, COOH, NH2, COMe, halogen and combinations thereof, wherein Rc is selected from the group consisting of O2, PO2, OH, halogen and combinations thereof, wherein Rd is selected from the group consisting of H and CH3, and combinations thereof, wherein Re is selected from the group consisting of OH, O2, S, halogen and combinations thereof, wherein B is OH, NH2, NHAc, or NH-alkyl wherein the alkyl comprises 1 to 18 Carbons, wherein W is selected from the group consisting of O, S, CH2, NH, or Se, wherein Y is selected from the group consisting of O, S, NH, CH2, Se, S, P, amino acid, and hydrophobic linear and cyclic hydrophobic hydrocarbons derivatives including heterocyclic substitutions of molecular weight of about 50-200 D and combinations thereof, wherein $R_1$, $R_2$, and $R_3$ are independently selected from the group consisting of H, O2, CO, NH2, SO2, SO, PO2, PO, CH3, linear hydrocarbon, and cyclic hydrocarbon, and wherein the hydrocarbon is one of a) an alkyl group of at least 3 carbons, an alkenyl group of at least 3 carbons, an alkyl group of at least 3 carbons substituted with a carboxy group, an alkenyl group of at least 3 carbons substituted with a carboxy group, an alkyl group of at least 3 carbons substituted with an amino group, an alkenyl group of at least 3 carbons substituted with an amino group, an alkyl group of at least 3 carbons substituted with both an amino and a carboxy group, an alkenyl group of at least 3 carbons substituted with both an amino and a carboxy group, and an alkyl group substituted with one or more halogens, b) a phenyl group substituted with at least one carboxy group, a phenyl group substituted with at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group, c) a naphthyl group, a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted With at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group, d) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and a heteroaryl group substituted with at least one substituted carbonyl group, and e) a saccharide, a substituted saccharide, D-galactose, Deoxygalactose, substituted D-Galactose, C3-[1,2,3]-triaZol-1-yl-substituted D-galactose, hydrogen, an alkyl group, an alkenyl group, an aryl group, a heteroaryl group, and a heterocycle and derivatives, an amino group, a substituted amino group, an imino group, or a substituted imino group.

In some embodiments, wherein A-M is representing a spacer of at least 2 atoms comprising an amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, Hydrazide —N(—H)—N(—H)—, and amino acid, or combinations thereof.

In some embodiments, the A-M spacer comprises of an amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, carbohydrazide —C(=O)—NH—NH—, sulfonohydrazide —S(=O)2-NH—NH—, or a phosphonic dihydrazide —P(=O)(—NH—NH2)(NH—NH—) spacer or any combination of the foregoing.

In some embodiments, the A-M spacer 2 or more atoms linked by single or double bond: C—C, C=C, C—P, C—N, C—O, N—C, N—N, N=N, N—S, N—P, S—N, P—O, O—P, S—C, S—N, S—S or combination thereof.

In some embodiments, the A-M spacer comprises PO2 or PO2-PO2 bond linked to the anomeric carbon and to one or more atoms such as C or N or O or S. In some embodiments, C or N is linked to the anomeric carbon and PO2 or PO2-PO2 is linked to C or N.

In some embodiments, the A-M is methylamide linked R1, R2 is N'-methylamide-3,4-difluorobenzene and Y—$R_1$ is triazole-3-fluorobenzene

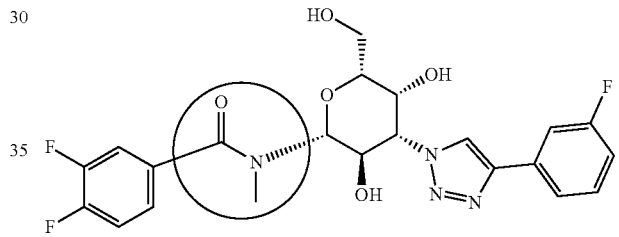

In some embodiments, the A-M spacer is linked to a galactose, a hydroxyl cyclohexane, an aromatic moiety, an alkyl group, an aryl group, an amine group, or amide group.

In some embodiments, the A-M spacer symmetrically links two galactosides or substituted derivatives thereof.

In some embodiments, the A-M spacer asymmetrically links two galactosides or substituted derivatives thereof.

In some embodiments, the anomeric carbon of the galactoside has a spacer of 2 or more atoms linked by single or double bond: C—C, C=O, C—P, C—N, C—O, N—C, N—N, N=N, N—S, N—P, S—N, P—O, O—P, or combination thereof.

Aspects of the invention relate to a compound or a pharmaceutically acceptable salt or solvate thereof having Formula 2:

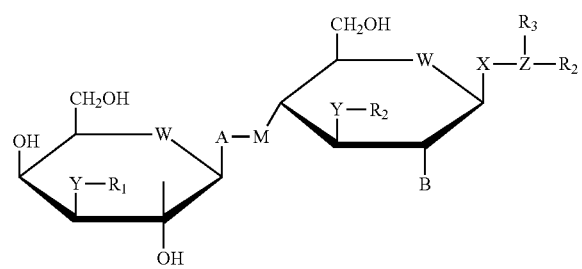

wherein A is independently selected the group consisting of NRa, CRb, PRc, or amino acid, wherein M is independently selected from the group consisting of NRa, CRb, PRc, ORd, SRe amino acid, or hydrophobic hydrocarbons derivatives including heterocyclic substitutions of 3 or more atoms, wherein Ra is selected from the group consisting of H, H2, CH3, COOH, NH2, COMe, halogen and combinations thereof, wherein Rb is selected from the group consisting of H, H2, O, OH, CH3, COOH, NH2, COMe, halogen and combinations thereof, wherein Rc is selected from the group consisting of O2, PO2, OH, halogen and combinations thereof, wherein Rd is selected from the group consisting of H and CH3, wherein Re is selected from the group consisting of OH, O2, S, halogen and combinations thereof, wherein B is OH, NH2, NHAc, or NH-alkyl wherein the alkyl comprises 1 to 18 Carbons, wherein W is selected from the group consisting of O, S, CH2, NH, and Se, wherein X is selected from the group consisting of O, N, S, CH2, NH, and PO2, wherein Y and Z are selected from the group consisting of O, S, C, NH, CH2, Se, S, P, amino acid, and hydrophobic linear and cyclic hydrophobic hydrocarbons derivatives including heterocyclic substitutions of molecular weight of about 50-200 D and combinations thereof, wherein R1, R2, R3, are independently selected from the group consisting of CO, O2, SO2, SO, PO2, PO, CH, Hydrogen, hydrophobic linear hydrocarbon, and hydrophobic cyclic hydrocarbon, wherein the hydrocarbon is one of:
a) an alkyl group of at least 3 carbons, an alkenyl group of at least 3 carbons, an alkyl group of at least 3 carbons substituted with a carboxy group, an alkenyl group of at least 3 carbons substituted with a carboxy group, an alkyl group of at least 3 carbons substituted with an amino group, an alkenyl group of at least 3 carbons substituted With an amino group, an alkyl group of at least 3 carbons substituted with both an amino and a carboxy group, an alkenyl group of at least 3 carbons substituted with both an amino and a carboxy group, and an alkyl group substituted with one or more halogens;
b) a phenyl group substituted with at least one carboxy group, a phenyl group substituted With at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group;
c) a naphthyl group, a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted With at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group; and
d) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and a heteroaryl group substituted with at least one substituted carbonyl group;
e) saccharide, a substituted saccharide, D-galactose, substituted D-galactose, C3-[1,2,3]-triaZol-1-yl-substituted D-galactose, hydrogen, an alkyl group, an alkenyl group, an aryl group, a heteroaryl group, and a heterocycle and derivatives, an amino group, a substituted amino group, an imino group, or a substituted imino group.

In some embodiments, A-M represents a spacer of at least 2 atoms comprising an amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, carbohydrazide —C(=O)—NH—NH—, sulfonohydrazide —S(=O)2-NH—NH—, and phosphonic dihydrazide —P(=O)(—NH—NH2)(NH—NH—) or combinations thereof.

In some embodiments, the A-M spacer 2 or more atoms linked by single or double bond: C—C, C=C, C—P, C—N, C—O, N—C, N—N, N=N, N—S, N—P, S—N, P—O, O—P, S—C, S—N, S—S or combination thereof.

In some embodiments, the A-M spacer of at least 2 atoms has a rotational freedom and length configured to allow an interaction of about 1 nM to about 50 μM to a galectin CRD epitope.

In some embodiments, the hydrophobic linear and cyclic hydrocarbons including heterocyclic substitutions have a molecule weight of about 50 to 200 D.

Aspects of the invention relate to a compound or a pharmaceutically acceptable salt or solvate thereof having formula of Table 1.

In some embodiments, the compound is in a free form. In some embodiments, the free form is an anhydrate. In some embodiments, the free form is a solvate, such as a hydrate.

In some embodiments, the compound of Formula (1) or Formula (2) is a crystalline form.

Some aspects of the invention relate to a compound of formula (1) for use as a therapeutic agent in a mammal, such as a human.

Some aspects of the invention relate to a pharmaceutical composition comprising the compound of Formula (1) or Formula (2) and optionally a pharmaceutically acceptable additive, such as carrier or excipient.

In some embodiments, the compounds of the invention bind to one or more galectins. In some embodiments, the compound binds to Galectin-3, Galectin-1, Galectin 8, and/or Galectin 9.

In some embodiments, the compounds of the invention have high selectivity and affinity for Galectin-3. In some embodiments, the compounds of the invention have an affinity of about 1 nM to about 50 μM for Galectin-3.

Aspects of the invention relate to compositions comprising the compound of the invention. In some embodiments, the composition comprises a therapeutically effective amount of the compound and a pharmaceutically acceptable adjuvant, excipient, formulation carrier or combinations thereof. In some embodiments, the composition comprises a therapeutically effective amount of the compound and of an anti-inflammatory drug, vitamin, pharmaceutical drug, nutraceutical drug, supplement, or combinations thereof.

Aspects of the invention relate to compounds, composition and methods that can be used in the treatment of diseases in a subject in need thereof. Aspects of the invention relate to compounds, composition and methods that can be used in the treatment of diseases in which galectins are at least in part involved in the pathogenesis.

Aspects of the invention relate to methods of treatment of a disease in a subject in need thereof. In some embodiments, the subject is a mammal. In some embodiments, the subject is a human.

In some embodiments, the compounds, composition and methods can be used in the treatment of nonalcoholic steatohepatitis with or without liver fibrosis, inflammatory and autoimmune disorders, neoplastic conditions or cancers.

In some embodiments, the compounds, composition and methods can be used in the treatment of liver fibrosis, kidney fibrosis, lung fibrosis, or heart fibrosis.

In some embodiments, the composition or the compound is capable of enhancing anti-fibrosis activity in organs, including but not limited to, liver, kidney, lung, and heart.

In some embodiments, the compounds, composition and methods can be used in treatment of inflammatory disorders of the vasculature including atherosclerosis and pulmonary hypertension.

In some embodiments, the compounds, composition and methods can be used in the treatment of heart disorders including heart failure, arrhythmias, and uremic cardiomyopathy.

In some embodiments, the compounds, composition and methods can be used in the treatment of kidney diseases including glomerulopathies and interstitial nephritis.

In some embodiments, the compounds, composition and methods can be used in the treatment of inflammatory, proliferative and fibrotic skin disorders, including but not limited to, psoriasis and scleroderma.

In some embodiments, the invention relates to a method of treating inflammatory and fibrotic disorders in which galectins are at least in part involved in the pathogenesis, by enhancing anti-fibrosis activity in organs, including, but not limited to, liver, kidney, lung, and heart.

In some embodiments, the invention relates to a composition or a compound that has a therapeutic activity to treat nonalcoholic steatohepatitis (NASH). In other aspects, the invention relates to a method to reduce the pathology and disease activity associated with nonalcoholic steatohepatitis (NASH).

In some embodiments, the invention relates to compounds, composition and methods for treating inflammatory and autoimmune disorders in which galectins are at least in part involved in the pathogenesis including but not limited to arthritis, rheumatoid arthritis, asthma, and inflammatory bowel disease.

In some embodiments, the invention relates to a composition or a compound to treat neoplastic conditions (e.g. benign or malignant neoplastic diseases) in which galectins are at least in part involved in the pathogenesis by inhibiting processes promoted by the increase in galectins. In some embodiments, the invention relates a method of treating neoplastic conditions (e.g. benign or malignant neoplastic diseases) in which galectins are at least in part involved in the pathogenesis by inhibiting processes promoted by the increase in galectins. In some embodiments, the composition or the compound can be used to treat or prevent tumor cell invasion, metastasis, and neovascularization. In some embodiments, the composition or the compound can be used to treat primary and secondary cancers.

In some embodiments, a therapeutically effective amount of the compound or of the composition can be compatible and effective in combination with a therapeutically effective amount of anti-inflammatory drugs, vitamins, other pharmaceuticals and nutraceuticals drugs or supplement, or combinations thereof without limitation.

Some aspects of the invention relate to a compound of Formula (1) Formula or (2) for use in a method for treating a disorder relating to the binding of a galectin. Some aspects of the invention relate to a compound of Formula (1) or Formula (2) for use in a method for treating a disorder relating to the binding of galectin-3 to a ligand.

Some aspects of the invention relate to a method for treatment of a disorder relating to the binding of a galectin, such as galectin-3, to a ligand in a human, wherein the method comprises administering a therapeutically effective amount of at least one compound of Formula (1) or Formula (2) to a human in need thereof.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

FIG. 3A depicts in-silico 3D model predicted docking pose of a GalactoamideSuccinimide linked Compound according to some embodiments.

FIG. 3B depicts in-silico 3D model predicted docking pose of a GalactoAmide linked compound according to some embodiments.

FIGS. 4A-4K depict the synthesis of exemplary Galacto-Amide compounds according to some embodiments.

FIG. 7B provides examples of Compounds IC50 (Inhibition concentration 50% score) by the ELISA Integrin-Gal-3 and ELISA MAb-Gal-3 assays according to some embodiments.

DETAILED DESCRIPTION OF THE INVENTION

Figure 1A:
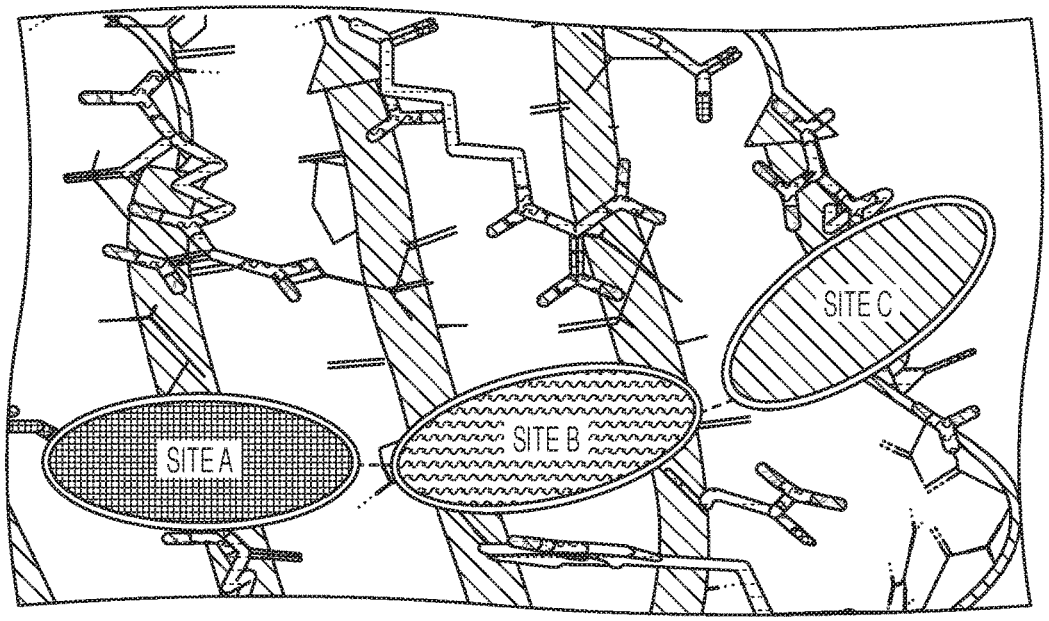
FIG. 1A depicts a high-definition 3D structure of galectin-3 Carbohydrate Recognition Domain (CRD) binding pocket with 3 potential sites of interaction.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Citation of documents herein is not intended as an admission that any of the documents cited herein is pertinent prior art, or an admission that the cited documents are considered material to the patentability of the claims of the present application.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for additional factors not described, unless the context clearly dictates otherwise. In addition, throughout the specification, the meaning of "a," "an," and "the" include plural references.

Unless otherwise specified, all percentages expressed herein are weight/weight.

Aspects of the invention relate to compositions of mono, disaccharides and oligosaccharides of Galactose (or heteroglycoside) core bound to an "amide" or "sulfonamide" linkage on the anomeric carbon of the Galactose (or heteroglycoside). In some embodiments, the "AM" containing molecules render them metabolically active while maintaining the chemical, physical and allosteric characteristics for specific interaction with lectins known to recognize carbohydrates. In some embodiments, the specific aromatic substitutions added to the galactose core further enhance the affinity of the "amide" bound pyranosyl and/or furanosyl structures by enhancing their interaction with amino acid residues (e.g. Arginine, Tryptophan, Histidine, Glutamic acid etc. . . . ) composing the carbohydrate-recognition-domains (CRD) of the lectins and thus strengthen the association and binding specificity.

Galectins

Galectins (also known as galaptins or S-lectins) are a family of lectins which bind beta-galactoside. Galectin as a general name was proposed in 1994 for a family of animal lectins (Barondes, S. H., et al.: Galectins: a family of animal beta-galactoside-binding lectins. Cell 76, 597-598, 1994). The family is defined by having at least one characteristic carbohydrate recognition domain (CRD) with an affinity for beta-galactosides and sharing certain sequence elements. Further structural characterization segments the galectins into three subgroups including: (1) galectins having a single CRD, (2) galectins having two CRDs joined by a linker peptide, and (3) a group with one member (galectin-3) which has one CRD joined to a different type of N-terminal domain. The galectin carbohydrate recognition domain is a beta-sandwich of about 135 amino acids. The two sheets are slightly bent with 6 strands forming the concave side, also called the S-face, and 5 strands forming the convex side, the F-face). The concave side forms a groove in which carbohydrate is bound (Leffler H, Carlsson S, Hedlund M, Qian Y, Poirier F (2004). "Introduction to galectins". Glycoconj. J. 19 (7-9): 433-40).

A wide variety of biological phenomena have been shown to be related to galectins, including development, differentiation, morphogenesis, tumor metastasis, apoptosis, RNA splicing, and many others.

Generally, the carbohydrate domain binds to galactose residues associated with glycoproteins. Galectins show an affinity for galactose residues attached to other organic compounds, such as in lactose [(β-D-Galactosido)-D-glucose], N-acetyl-lactosamine, poly-N-acetyllactosamine, galactomannans, or fragments of pectins. However, it should be noted that galactose by itself does not bind to galectins.

Plant polysaccharides like pectin and modified pectin have been shown to bind to galectin proteins presumably on the basis of containing galactose residues that are presented in the context of a macromolecule, in this case a complex carbohydrate rather than a glycoprotein in the case of animal cells.

At least fifteen mammalian galectin proteins have been identified which have one or two carbohydrate domain in tandem.

Galectin proteins are found in the intracellular space where they have been assigned a number of functions and they are also are secreted into the extracellular space where they have different functions. In the extracellular space, galectin proteins can have multiple functions that are mediated by their interaction with galactose containing glycoproteins including promoting interactions between glycoproteins that may modulate function or, in the case of integral membrane glycoprotein receptors, modification of cellular signaling (Sato et al "Galectins as danger signals in host-pathogen and host-tumor interactions: new members of the growing group of "Alarmins." In "Galectins," (Klyosov, et al eds.), John Wiley and Sons, 115-145, 2008, Liu et al "Galectins in acute and chronic inflammation," Ann. N.Y.

Acad. Sci. 1253: 80-91, 2012). Galectin proteins in the extracellular space can additionally promote cell-cell and cell matrix interactions (Wang et al., "Nuclear and cytoplasmic localization of galectin-1 and galectin-3 and their roles in pre-mRNA splicing." In "Galectins" (Klyosov et al eds.), John Wiley and Sons, 87-95, 2008). In regards to intracellular space, galectin functions appear to be more related to protein-protein interactions, although intracellular vesicle trafficking appears to be related to interaction with glycoproteins.

Galectins have been shown to have domains which promote homodimerization. Thus, galectins are capable of acting as a "molecular glue" between glycoproteins. Galectins are found in multiple cellular compartments, including the nucleus and cytoplasm, and are secreted into the extracellular space where they interact with cell surface and extracellular matrix glycoproteins. The mechanism of molecular interactions can depend on the localization. While galectins can interact with glycoproteins in the extracellular space, the interactions of galectin with other proteins in the intracellular space generally occurs via protein domains. In the extracellular space the association of cell surface receptors may increase or decrease receptor signaling or the ability to interact with ligands.

Galectin proteins are markedly increased in a number of animal and human disease states, including but not limited to diseases associated with inflammation, fibrosis, autoimmunity, and neoplasia. Galectins have been directly implicated in the disease pathogenesis, as described below. For example, diseases states that may be dependent on galectins include, but are not limited to, acute and chronic inflammation, allergic disorders, asthma, dermatitis, autoimmune disease, inflammatory and degenerative arthritis, immune-mediated neurological disease, fibrosis of multiple organs (including but not limited to liver, lung, kidney, pancreas, and heart), inflammatory bowel disease, atherosclerosis, heart failure, ocular inflammatory disease, a large variety of cancers.

In addition to disease states, galectins are important regulatory molecules in modulating the response of immune cells to vaccination, exogenous pathogens and cancer cells.

One of skill in the art will appreciate that compounds that can bind to galectins and/or alter galectin's affinity for glycoproteins, reduce hetero- or homo-typic interactions between galectins, or otherwise alter the function, synthesis, or metabolism of galectin proteins may have important therapeutic effects in galectin-dependent diseases.

Galectin proteins, such as galectin-1 and galectin-3 have been shown to be markedly increased in inflammation, fibrotic disorders, and neoplasia (Ito et al. "Galectin-1 as a potent target for cancer therapy: role in the tumor microenvironment", Cancer Metastasis Rev. PMID: 22706847 (2012), Nangia-Makker et al. Galectin-3 binding and metastasis," Methods Mol. Biol. 878: 251-266, 2012, Canesin et al. Galectin-3 expression is associated with bladder cancer progression and clinical outcome," Tumour Biol. 31: 277-285, 2010, Wanninger et al. "Systemic and hepatic vein galectin-3 are increased in patients with alcoholic liver cirrhosis and negatively correlate with liver function," Cytokine. 55: 435-40, 2011). Moreover, experiments have shown that galectins, particularly galectin-1 (gal-1) and galectin-3 (gal-3), are directly involved in the pathogenesis of these classes of disease (Toussaint et al., "Galectin-1, a gene preferentially expressed at the tumor margin, promotes glioblastoma cell invasion.", Mol. Cancer. 11:32, 2012, Liu al 2012, Newlaczyl et al., "Galectin-3-a jack-of-all-trades in cancer," Cancer Lett. 313: 123-128, 2011, Banh et al., "Tumor galectin-1 mediates tumor growth and metastasis through regulation of T-cell apoptosis," Cancer Res. 71: 4423-31, 2011, Lefranc et al., "Galectin-1 mediated biochemical controls of melanoma and glioma aggressive behavior," World J. Biol. Chem. 2: 193-201, 2011, Forsman et al., "Galectin 3 aggravates joint inflammation and destruction in antigen-induced arthritis," Arthritis Reum. 63: 445-454, 2011, de Boer et al., "Galectin-3 in cardiac remodeling and heart failure," Curr. Heart Fail. Rep. 7, 1-8, 2010, Ueland et al., "Galectin-3 in heart failure: high levels are associated with all-cause mortality," Int J. Cardiol. 150: 361-364, 2011, Ohshima et al., "Galectin 3 and its binding protein in rheumatoid arthritis," Arthritis Rheum. 48: 2788-2795, 2003).

High levels of serum Galectin-3 have been shown to be associated with some human diseases, such as a more aggressive form of heart failure, which make identification of high-risk patients using galectin-3 testing an important part of patient care. Galectin-3 testing may be useful in helping physicians determine which patients are at higher risk of hospitalization or death. For example, the BGM Galectin-3® Test is an in vitro diagnostic device that quantitatively measures galectin-3 in serum or plasma and can be used in conjunction with clinical evaluation as an aid in assessing the prognosis of patients diagnosed with chronic heart failure. Measure of the concentration of endogenous protein galectin-3 can be used to predict or monitor disease progression or therapeutic efficacy in patients treated with cardiac resynchronization therapy (see U.S. Pat. No. 8,672, 857, which is incorporated herein by reference in its entirety).

Galectin-8 (gal-8) has been shown to be over-expressed in lung carcinomas and is in the invasive regions of xenografted glioblastomas.

Galectin-9 (gal-9) is believed to be involved in the control of lesions arising from immunoinflammatory diseases, and be generally implicated in inflammation. Gal-9 appears to mediate apoptosis in certain activated cells.

Aspects of the invention relate to compounds that bind galectins involved in human disorders, such as inflammatory diseases, fibrotic diseases, neoplastic diseases or combinations thereof. In some embodiments, the compounds bind galectins, such as galectin-1 (gal-1), galectin-3 (gal-3), galectin-8 (gal-8) and/or galectin-9 (gal-9).

Galectin Inhibitors

Natural oligosaccharide ligands capable of binding to galectin-1 and/or galectin-3, for example, modified forms of pectins and galactomannan derived from Guar-gum have been described (see WO 2013040316, US 20110294755, WO 2015138438). Synthetic digalactosides like lactose, N-acetyllactosamine (LacNAc) and thiolactose effective against pulmonary fibrosis and other fibrotic disease (WO 2014067986 A1).

Advances in protein crystallography and availability of high definition 3D structure of the carbohydrate recognition domain (CRD) of many galectins have generated many derivatives with enhanced affinity to the CRD having a greater affinity than galactose or lactose (WO 2014067986 A). These compounds were shown to be effective for treatment of an animal model of lung fibrosis which is thought to mimic human idiopathic pulmonary fibrosis (IPF). For example a thio-digalactopyranosyl substituted with 3-fluorophenyl-2,3-triazol groups (TD-139) has been reported to bind to galectin 3 and to be effective in in a mouse model of lung fibrosis. The compound required pulmonary administration using intra-tracheal instillation or nebulizers (see U.S. Pat. Nos. 8,703,720, 7,700,763, 7,638,623 7,230,096).

Aspects of the invention relates to novel compounds that mimic the natural ligand of galectin proteins. In some embodiments, the compound mimics the natural ligand of galectin-3. In some embodiments, the compound mimics the natural ligand of galectin-1.

Figure 1B:
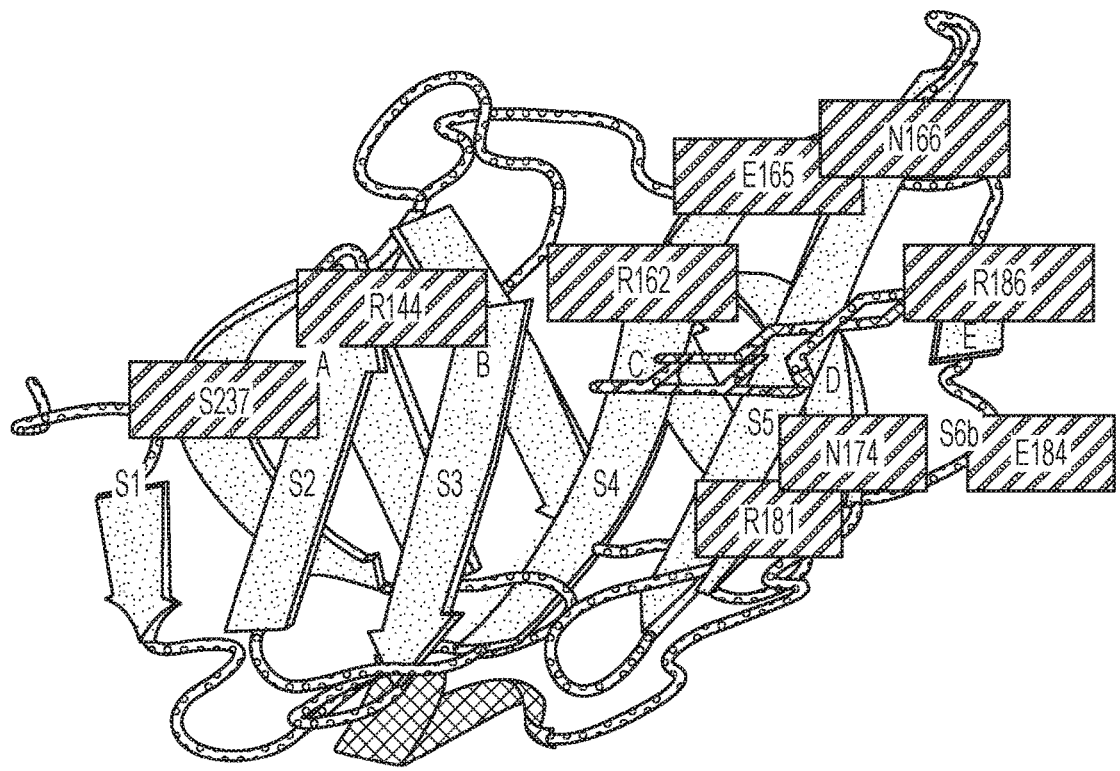
FIG. 1B depicts the CRD pocket location in the Galectin-3 C-terminal with bound lactose unit.
Figure 2:
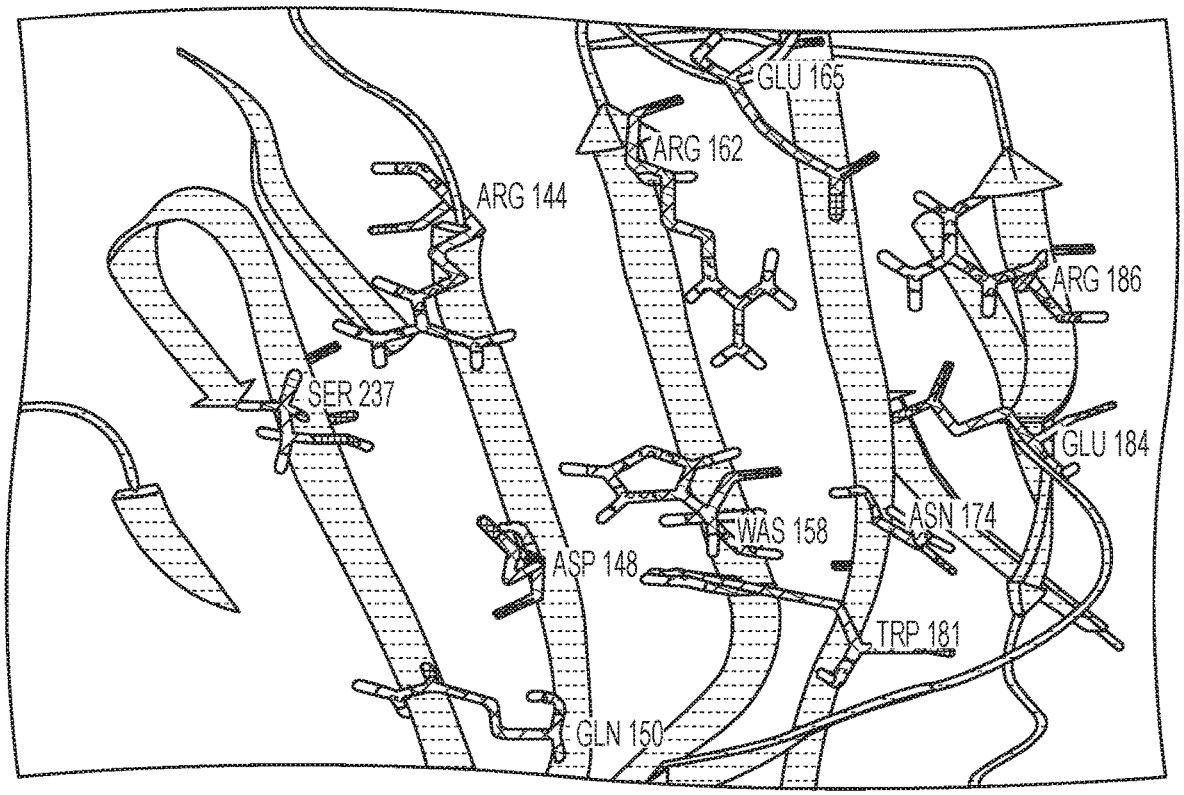
FIG. 2 depicts a map of the Galectin-3 CRD site vicinity—potential cooperative amino-acids for enhanced binding.

In some embodiments, the compound has a mono, di or oligomer structure composed of Galactose-AM core bound to the anomeric carbon on the galactose and which serves as a linker to the rest of the molecule. In some embodiments, the Galactose-AM core may be bound to other saccharide/amino acid/acids/group that bind galectin CRD (as shown in FIGS. 1A, 1B) in the high definition 3D structure of galectin-3) and together can enhance the compound's affinity to the CRD. In some embodiments, the Galactose-AM core may be bound to other saccharide/amino acid/acid/group that bind in "site B" of the galectin CRD (as shown in FIGS. 1A, 1B & FIG. 2 in the high definition 3D structure of galectin-3) and together can enhance the compound's affinity to the CRD.

According to some aspects, the compounds can have substitutions that interact with site A and/or site C to further improve the association with the CRD and enhance their potential as a therapeutic targeted to galectin-dependent pathology. In some embodiments, the substituents can be selected through in-silico analysis (computer assisted molecular modeling) as described herein. In some embodiments, the substituents can be further screened using binding assay with the galectin protein of interest. For example, the compounds can be screened using a galectin-3 binding assay and/or an in-vitro inflammatory and fibrotic model of activated cultured macrophages (see Macrophage polarization minireview, AbD Serotec).

According to some aspects, the compounds comprise one or more specific substitutions of the core Galactose-AM. For example, the core Galactose-AM can be substituted with specific substituents that interact with residues located within the CRD. Such substituents can dramatically increase the association and potential potency of the compound as well as the 'drugability' characteristic (FIGS. 3A, 3B)

Galactoside Compounds

Most "amide" and "sulfon" compounds, organic and inorganic, are readily absorbed from the diet and transported to the liver—the prime organ for metabolism. The general metabolism of "amide" compounds follows three major routes depending on the chemical properties, that is, redox-active "amide" compounds, precursors of methylamide and conjugation with amino acids.

AM Spacer

Aspects of the invention relates to compounds comprising pyranosyl and/or furanosyl galactose structures bound to an ""A-M" spacer on the anomeric carbon of the pyranosyl and/or furanosyl.

In some embodiments, wherein A-M is representing a spacer of at least 2 atoms comprising an amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, Hydrazide —N(—H)—N(—H)—, and amino acid, or combinations thereof.

In some embodiments, the A-M spacer comprises an amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, carbohydrazide —C(=O)—NH—NH—, sulfonohydrazide —S(=O)2-NH—NH—, or a phosphonic dihydrazide —P(=O)(—NH—NH2)(NH—NH—) spacer or any combination of the foregoing.

In some embodiments, the A-M spacer comprises 2 or more atoms linked by single or double bond: C—C, C=O, C—P, C—N, C—O, N—C, N—N, N=N, N—S, N—P, S—N, P—O, O—P, S—C, S—N, S—S or combination thereof.

In some embodiments, the A-M spacer comprises PO2 or PO2-PO2 bond linked to the anomeric carbon and to one or more atoms such as C or N or O or S. In some embodiments, C or N is linked to the anomeric carbon and PO2 or PO2-PO2 is linked to C or N.

Without being bound to the theory, A-M is representing a spacer of at least 2 atoms that has more rotational freedom and length thus affording closer and tighter interaction to the galectin CRD epitope and surrounding aminoacids sites. Spacers like an amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, carbohydrazide —C(=O)—NH—NH—, sulfonohydrazide —S(=O)2-NH—NH—, and phosphonic dihydrazide —P(=O)(—NH—NH2)(NH—NH—) augment the interaction with the galectin.

Aspects of the invention relates to compounds comprising pyranosyl and/or furanosyl galactose structures bound to an "amide" or "sulfon" type structures on the anomeric carbon of the pyranosyl and/or furanosyl. As used herein an amide bond refers to a C—N bond (R—C(O)—NH—R). In some embodiments, the amide bond can be a sulfonamide bond. In some embodiments, the sulfon bond can have the genera formula R—S(=O)$_2$—R'. As used herein an amide bond refers to a C—N bond (R—C(O)—NH—R). In some embodiments, the amide bond can be a N—SO2 (sulfonamide bond). or the genera R—N—S(=O)$_2$—R'. In some embodiments, the C—SO2 (sulfon bond) can have the genera formula R—C—S(=O)$_2$—R'.

In some embodiments, specific aromatic substitutions can be added to the galactose core or heteroglycoside core to further enhance the affinity of the "amide" bound pyranosyl and/or furanosyl structures. Such aromatic substitutions can enhance the interaction of the compound with amino acid residues (e.g. Arginine, Tryptophan, Histidine, Glutamic acid etc. . . . ) composing the carbohydrate-recognition-domains (CRD) of the lectins and thus strengthen the association and binding specificity.

In some embodiments, the compound comprises monosaccharides, disaccharides and oligosaccharides of galactose or a heteroglycoside core bound to an "amide" or "sulfon" atom on the anomeric carbon of the galactose or of the heteroglycoside.

In some embodiments, the compound is a symmetric digalactoside wherein the two galactosides are bound by one or more "amide" and/or "sulfon" bonds. In some embodiments, the compound is a symmetric digalactoside wherein the two galactosides are bound by one or more sulfonamide bonds. In some embodiments, the compound is a symmetric digalactoside wherein the two galactosides are bound by one or more "amide" bonds and wherein the "amide" is bound to the anomeric carbon of the galactose. In some embodiments, the compound is a symmetric digalactoside wherein the two galactosides are bound by one or more "amide" bonds and one or more sulfon bonds and wherein the "amide" is bound to the anomeric carbon of the galactose. Yet in other embodiments, the compound can be an asymmetric digalactoside.

For example, the compound can have different aromatic or aliphatic substitutions on the galactose core.

In some embodiments, the compound is asymmetric galactoside wherein a single galactoside having one or more "amide" or "sulfon" on the anomeric carbon of the galactose. In some embodiments, the galactoside has one or more "amide" bound to the anomeric carbon of the galactose and one or more sulfur bound to the "amide". In some embodiments, the compound can have different aromatic or aliphatic substitutions on the galactose core.

Without being bound to the theory, it is believed that the compounds containing the AM linkage render the compound metabolically stable while maintaining the chemical, physical and allosteric characteristics for specific interaction with lectins or galectins known to recognize carbohydrates. In some embodiments, the digalactoside or oligosaccharides of galactose of the invention are metabolically more stable than compounds having an O-glycosidic bond and resistant to most galacosidase digestion. In some embodiments, the digalactoside or oligosaccharides of galactose of the invention are metabolically more stable than compounds having an S-glycosidic bond.

Aspects of the invention relate to compounds having based on galactoside structure with "amide" type bridge [AM] to another galactose, hydroxyl cyclohexane, aromatic moiety, alkyl, aryl, amine, or amide group.

As used herein, the term "alkyl group" is meant to comprise from 1 to 12 carbon atoms, for example 1 to 7 or 1 to 4 carbon atoms. In some embodiments, the alkyl group may be a straight- or a branched-chain. In some embodiments, the alkyl group may also form a cycle comprising from 3 to 7 carbon atoms, preferably 3, 4, 5, 6, or 7 carbon atoms. Thus alkyl encompasses any of methyl, ethyl, n-propyl, isopropyl, n-butyl, sec-butyl, tert-butyl, pentyl, isopentyl, 3-methylbutyl, 2,2-dimethylpropyl, n-hexyl, 2-methylpentyl, 2,2-dimethylbutyl, 2,3-dimethylbutyl, n-heptyl, 2-methylhexyl, 2,2-dimethylpentyl, 2,3-dimethylpentyl, cyclopropyl, cyclobutyl, cyclopentyl, cyclohexyl, cycloheptyl, and 1-methylcyclopropyl.

As used herein, the term "alkenyl group" is meant to comprise from 2 to 12, for example 2 to 7 carbon atoms. The alkenyl group comprises at least one double bond. In some embodiments, the alkenyl group encompasses any of vinyl, allyl, but-1-enyl, but-2-enyl, 2,2-dimethylethenyl, 2,2-dimethylprop-1-enyl, pent-1-enyl, pent-2-enyl, 2,3-dimethylbut-1-enyl, hex-1-enyl, hex-2-enyl, hex-3-enyl, prop-1,2-dienyl, 4-methylhex-1-enyl, cycloprop-1-enyl group, and others.

As used herein, the term "alkoxy group" relates to an alkoxy group containing 1-12 carbon atoms, which may include one or more unsaturated carbon atoms. In some embodiments the alkoxy group contains 1 to 7 or 1 to 4 carbon atoms, which may include one or more unsaturated carbon atoms. Thus the term "alkoxy group" encompasses a methoxy group, an ethoxy group, a propoxy group, a isopropoxy group, a n-butoxy group, a sec-butoxy group, tert-butoxy group, pentoxy group, isopentoxy group, 3-methylbutoxy group, 2,2-dimethylpropoxy group, n-hexoxy group, 2-methylpentoxy group, 2,2-dimethylbutoxy group 2,3-dimethylbutoxy group, n-heptoxy group, 2-methylhexoxy group, 2,2-dimethylpentoxy group, 2,3-dimethylpentoxy group, cyclopropoxy group, cyclobutoxy group, cyclopentyloxy group, cyclohexyloxy group, cycloheptyloxy group, and 1-methylcyclopropyloxy group.

As used herein, the term "aryl group" is meant to comprise from 4 to 12 carbon atoms. Said aryl group may be a phenyl group or a naphthyl group. The above-mentioned groups may naturally be substituted with any other known substituents within the art of organic chemistry. The groups may also be substituted with two or more of the said substituents. Examples of substituents are halogen, alkyl, alkenyl, alkoxy, nitro, sulfo, amino, hydroxy, and carbonyl groups. Halogen substituents can be bromo, fluoro, iodo, and chloro. Alkyl groups are as defined above containing 1 to 7 carbon atoms. Alkenyl are as defined above containing 2 to 7 carbon atoms, preferably 2 to 4. Alkoxy is as defined below containing 1 to 7 carbon atoms, preferably 1 to 4 carbon atoms, which may contain an unsaturated carbon atom. Combinations of substituents can be present such as trifluoromethyl.

As used herein, the term "heteroaryl group" is meant to comprise any aryl group comprising from 4 to 18 carbon atoms, wherein at least one atom of the ring is a heteroatom, i.e. not a carbon. In some embodiments, the heteroaryl group may be a pyridine, or an indole group.

The above-mentioned groups may be substituted with any other known substituents within the art of organic chemistry. The groups may also be substituted with two or more of the substituents. Examples of substituents are halogen, alkoxy, nitro, sulfo, amino, hydroxy, and carbonyl groups. Halogen substituents can be bromo, fluoro, iodo, and chloro. Alkyl groups are as defined above containing 1 to 7 carbon atoms. Alkenyl are as defined above containing 2 to 7 carbon atoms, for example 2 to 4. Alkoxy is as defined below containing 1 to 7 carbon atoms, for example 1 to 4 carbon atoms, which may contain an unsaturated carbon atom. In some embodiments, the substituents can comprise a) an alkyl group of at least 3 carbons, an alkenyl group of at least 3 carbons, an alkyl group of at least 3 carbons substituted with a carboxy group, an alkenyl group of at least 3 carbons substituted with a carboxy group, an alkyl group of at least 3 carbons substituted with an amino group, an alkenyl group of at least 3 carbons substituted with an amino group, an alkyl group of at least 3 carbons substituted with both an amino and a carboxy group, an alkenyl group of at least 3 carbons substituted with both an amino and a carboxy group, and an alkyl group substituted with one or more halogens. Halogens can be a fluoro, a chloro, a bromo or an iodo group.

b) a phenyl group substituted with at least one carboxy group, a phenyl group substituted with at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group, c) a naphthyl group, a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted with at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group; and d) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and a heteroaryl group substituted with at least one substituted carbonyl group;

e) saccharide; a substituted saccharide, D-galactose, substituted D-galactose, C3-[1,2,3]-triazol-1-yl-substituted D-galactose, hydrogen, an alkyl group, an alkenyl group, an aryl group, a heteroaryl group, and a heterocycle and derivatives, an amino group, a substituted amino group, animino group, or a substituted imino group.

Wherein NRx is selected from the group consisting of hydrogen, an alkyl group, an alkenyl group, an aryl group, a heteroaryl group, and a heterocycle.

As used herein, the term "alkoxy group" relates to an alkoxy group containing 1-7 carbon atoms, which may include one or more unsaturated carbon atoms. In some embodiments the alkoxy group contains 1-4 carbon atoms, which may include one or more unsaturated carbon atoms. Thus the term "alkoxy group" encompasses a methoxy group, an ethoxy group, a propoxy group, a isopropoxy group, a n-butoxy group, a sec-butoxy group, tert-butoxy group, pentoxy group, isopentoxy group, 3-methylbutoxy group, 2,2-dimethylpropoxy group, n-hexoxy group, 2-methylpentoxy group, 2,2-dimethylbutoxy group 2,3-dimethylbutoxy group, n-heptoxy group, 2-methylhexoxy group, 2,2-dimethylpentoxy group, 2,3-dimethylpentoxy group, cyclopropoxy group, cyclobutoxy group, cyclopentyloxy group, cyclohexyloxy group, cycloheptyloxy group, and 1-methylcyclopropyloxy group.

Monomeric Compound

In some embodiments, the compound or a pharmaceutically acceptable salt or solvate thereof has Formula 1 wherein A is independently selected from the group consisting of NRa, CRb, PRc, and amino acid, wherein M is independently selected from the group consisting of NRa, CRb, PRc, ORd, SRe amino acid, and hydrophobic hydrocarbons derivatives including heterocyclic substitutions of 3 or more atoms, wherein Ra is selected from the group consisting of H, H2, CH3, COOH, NH2, COMe, halogen and combinations thereof, wherein Rb is selected from the group consisting of H, H2, O, OH, CH3, COOH, NH2, COMe, halogen and combinations thereof, wherein Rc is selected from the group consisting of O2, PO2, OH, halogen and combinations thereof, wherein Rd is selected from the group consisting of H, CH3, an combinations thereof, wherein Re is selected from the group consisting of OH, O2, S, halogen and combinations thereof, wherein B is OH, NH2, NHAc, or NH-alkyl, wherein the alkyl group comprises 1 to 18 Carbons, wherein W is selected from the group consisting of O, S, CH2, NH, and Se, wherein Y is selected from the group consisting of O, S, NH, CH2, Se, S, P, amino acid, and hydrophobic linear and cyclic hydrophobic hydrocarbons derivatives including heterocyclic substitutions of molecular weight of about 50-200 D and combinations thereof, wherein $R_1$, $R_2$, and $R_3$ are independently selected from the group consisting of H, O2, CO, NH2, SO2, SO, PO2, PO, CH3, linear hydrocarbon, and cyclic hydrocarbon, and wherein the hydrocarbon is one of a) an alkyl group of at least 3 carbons, an alkenyl group of at least 3 carbons, an alkyl group of at least 3 carbons substituted with a carboxy group, an alkenyl group of at least 3 carbons substituted with a carboxy group, an alkyl group of at least 3 carbons substituted with an amino group, an alkenyl group of at least 3 carbons substituted with an amino group, an alkyl group of at least 3 carbons substituted with both an amino and a carboxy group, an alkenyl group of at least 3 carbons substituted with both an amino and a carboxy group, and an alkyl group substituted with one or more halogens, b) a phenyl group substituted with at least one carboxy group, a phenyl group substituted with at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group, c) a naphthyl group, a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted With at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group, d) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and a heteroaryl group substituted with at least one substituted carbonyl group, and e) a saccharide, a substituted saccharide, D-galactose, Deoxygalactose, substituted D-Galactose, C3-[1,2,3]-triaZol-1-yl-substituted D-galactose, hydrogen, an alkyl group, an alkenyl group, an aryl group, a heteroaryl group, and a heterocycle and derivatives, an amino group, a substituted amino group, an imino group, or a substituted imino group.

In some embodiments, wherein A-M represents a spacer of at least 2 atoms comprising an amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, Hydrazide —N(—H)—N(—H)—, amino acid, or combinations thereof, In some embodiments, the compound has the general formula (1), wherein AM-R1 is for example N'-methylamide-3,4-difluorobenzene, wherein Y—R1 is triazole-3-fluorobenzene

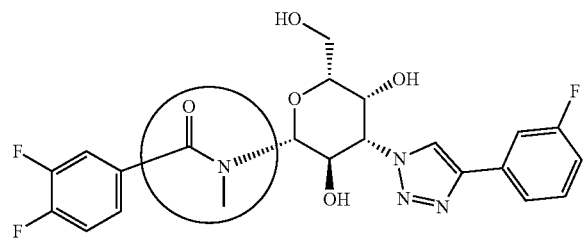

Dimeric Compounds

In some embodiments, the compound is a dimeric-polyhydroxylated-cycloalkanes compound.

In some embodiments, the compound or a pharmaceutically acceptable salt or solvate thereof has Formula 2:

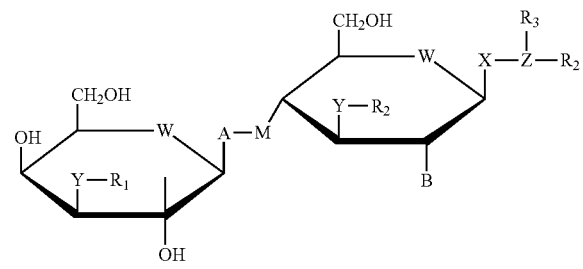

wherein A-M is representing a spacer of at least 2 atoms comprising an amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, carbohydrazide —C(=O)—NH—NH—, sulfonohydrazide —S(=O)2-NH—NH—, Hydrazide —N(—H)—N(—H)—, phosphonic dihydrazide —P(=O)(—NH—NH2)(NH—NH—) or combinations thereof, wherein A is independently selected from NRa, CRb, PRc, and amino acid, wherein M is independently selected from of NRa, CRb, PRc, ORd, SRe amino acid, and hydrophobic hydrocarbons derivatives including heterocyclic substitutions of 3 or more atoms, wherein Ra is selected from the group consisting of H, H2, CH3, COOH, NH2, COMe, halogen and combinations thereof, wherein Rb is selected from the group consisting of H, H2, O, OH, CH3, COOH, NH2, COMe, halogen and combinations thereof, wherein Rc is selected from the group consisting of O2, PO2, OH, halogen and combinations thereof, wherein Rd is selected from the group consisting of H, CH3, and combinations thereof, wherein Re is selected from the group consisting of OH, O2, S, halogen and combinations thereof, wherein B is OH, NH2, NHAc, or NH-alkyl of 1 to 18 Carbons, wherein W is selected from the group consisting of O, S, CH2, NH, or Se, Wherein X is selected from the group consisting of O, N, S, CH2, NH, and PO2, wherein Y and Z are selected from the group consisting of O, S, C, NH, CH2, Se, S, P, amino acid, and hydrophobic linear and cyclic hydrophobic hydrocarbons derivatives including heterocyclic substitutions of molecular weight of about 50-200 D and combinations thereof, wherein R1, R2, R3, are independently selected from the group consisting of CO, O2, SO2, SO, PO2, PO, CH, Hydrogen, hydrophobic linear hydrocarbon, and hydrophobic cyclic hydrocarbon, wherein the hydrocarbon is one of:

a) an alkyl group of at least 3 carbons, an alkenyl group of at least 3 carbons, an alkyl group of at least 3 carbons substituted with a carboxy group, an alkenyl group of at least 3 carbons substituted with a carboxy group, an alkyl group of at least 3 carbons substituted with an amino group, an alkenyl group of at least 3 carbons substituted With an amino group, an alkyl group of at least 3 carbons substituted with both an amino and a carboxy group, an alkenyl group of at least 3 carbons substituted with both an amino and a carboxy group, and an alkyl group substituted with one or more halogens;

b) a phenyl group substituted with at least one carboxy group, a phenyl group substituted With at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group, c) a naphthyl group, a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted With at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group; and d) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and a heteroaryl group substituted with at least one substituted carbonyl group.

e) saccharide, a substituted saccharide, D-galactose, substituted D-galactose, C3-[1,2,3]-triaZol-1-yl-substituted D-galactose, hydrogen, an alkyl group, an alkenyl group, an aryl group, a heteroaryl group, and a heterocycle and derivatives; an amino group, a substituted amino group, an imino group, or a substituted imino group.

In some embodiments, the compound has the general formulas below

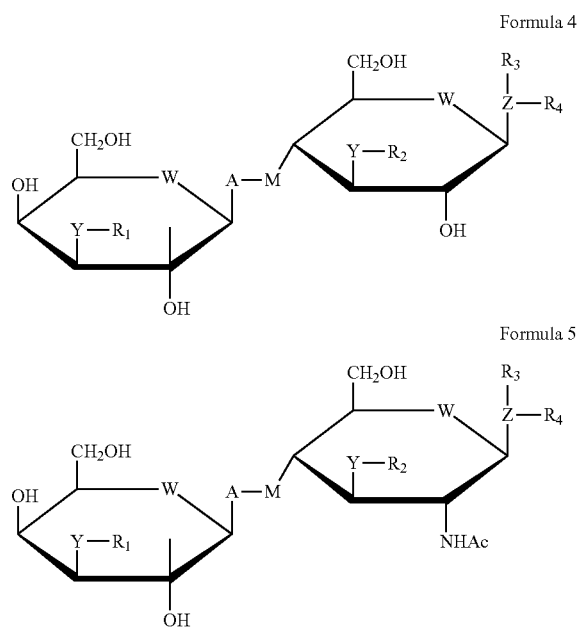

Formula 4

Formula 5

Wherein A-M is an amide, Sulfate, sulfonamide, a carbon ester and/or includes an aryl derivative like AM-Benzene-AM structure (Example 14, Scheme 6).

Wherein W is selected from the group consisting of O, N, S, CH2, NH, and Se;

Wherein Y and Z are selected from the group consisting of O, S, C, NH, CH2, NR, Se, or Amino acid.

Wherein $R_1$, $R_2$, $R_3$, and $R_4$ (Rx) are independently selected from the group consisting of CO, SO2, SO, PO2, PO, CH, Hydrogen, Hydrophobic linear and cyclic including Heterocyclic substitutions of molecular weight of 50-200 D including, but not limited to:

a) an alkyl group of at least 3 carbons, an alkenyl group of at least 3 carbons, an alkyl group of at least 3 carbons substituted with a carboxy group, an alkenyl group of at least 3 carbons substituted with a carboxy group, an alkyl group of at least 3 carbons substituted with an amino group, an alkenyl group of at least 3 carbons substituted with an amino group, an alkyl group of at least 3 carbons substituted with both an amino and a carboxy group, an alkenyl group of at least 3 carbons substituted with both an amino and a carboxy group, and an alkyl group substituted with one or more halogens;

b) a phenyl group substituted with at least one carboxy group, a phenyl group substituted With at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group, c) a naphthyl group, a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted With at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group; and d) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and a heteroaryl group substituted with at least one substituted carbonyl group.

e) saccharide, a substituted saccharide, D-galactose, substituted D-galactose, C3-[1,2,3]-triaZol-1-yl-substituted D-galactose, hydrogen, an alkyl group, an alkenyl group, an aryl group, a heteroaryl group, and a heterocycle and derivatives; an amino group, a substituted amino group, animino group, or a substituted imino group.

Rx is selected from the group consisting of hydrogen, an alkyl group, an alkenyl group, an aryl group, a heteroaryl group, and a heterocycle.

As used herein, the term "alkyl group" relates to an alkyl group containing 1-7 carbon atoms, which may include one or more unsaturated carbon atoms. In some embodiments the alkyl group contains 1-4 carbon atoms, which may include one or more unsaturated carbon atoms. The carbon atoms in the alkyl group may form a straight or branched chain. The carbon atoms in said alkyl group may also form a cycle containing 3, 4, 5, 6, or 7 carbon atoms. Thus, the term "alkyl group" used herein encompasses methyl, ethyl, n-propyl, isopropyl, n-butyl, sec-butyl, tert-butyl, pentyl, isopentyl, 3-methylbutyl, 2,2-dimethylpropyl, n-hexyl, 2-methylpentyl, 2,2-dimethylbutyl, 2,3-dimethylbutyl, n-heptyl, 2-methylhexyl, 2,2-dimethylpentyl, 2,3-dimethylpentyl, cyclopropyl, cyclobutyl, cyclopentyl, cyclohexyl, cycloheptyl, and 1-methylcyclopropyl.

Without being bound to the theory, the galactose-Amide or sulfu based linker compounds described herein have an enhanced stability as its structure is less prone to hydrolysis (metabolism) and oxidation e.g. aromatic ring without substitutions, Carbon-Oxygen systems, Carbone-Nitrogen system etc.

Synthetic Route

The compounds of this invention may be prepared by the following general methods and procedures. It should be appreciated that where typical or preferred process conditions (e.g. reaction temperatures, times, molar ratios of reactants, solvents, pressures, pH etc) are given, other process conditions may also be used unless otherwise stated. Optimum reaction conditions may vary with the particular reactants, solvents used and pH etc., but such conditions can be determined by one skilled in the art by routine optimization procedures.

In some embodiments, the compounds were synthetized using the synthetic routes as given in Example 14 and shown in FIG. 4.

For example, compound G631 (a Galactosulfonamide, GTJC-026) was prepared as shown in Example 14 Scheme 11 (as shown FIG. 4).

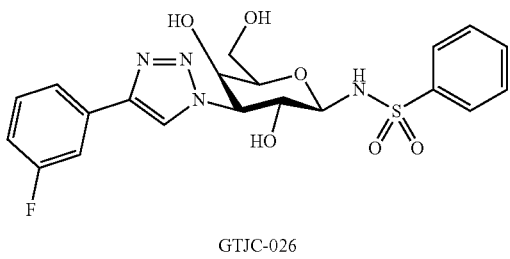

GTJC-026

In some embodiments, the di-galactoamide compounds were synthetized using the synthetic routes as given in Example 14 Scheme 6 and shown in FIG. 4.

For example, compound G637 (a di-galactoamide with arylamide linkage, GTJC-013-12) was prepared as shown in Example 14 Scheme 6 and shown in FIG. 4.

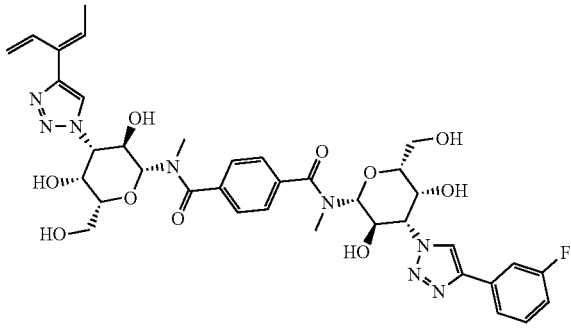 [SMILES: C=C/C(=C\C)c1cn([C@@H]2[C@@H](O)[C@H](N(C)C(=O)c3ccc(C(=O)N(C)[C@@H]4O[C@H](CO)[C@H](O)[C@H](n5cc(-c6cccc(F)c6)nn5)[C@H]4O)cc3)O[C@H](CO)[C@@H]2O)nn1]

Pharmaceutical Compositions

Aspects of the invention relate to the use of the compounds described herein for the manufacture of medicaments.

Aspects of the invention relate to pharmaceutical compositions comprising one or more of the compounds described herein. In some embodiments, the pharmaceutical compositions comprise one or more of the following: pharmaceutically acceptable adjuvant, diluent, excipient, and carrier.

In some embodiments, the pharmaceutical composition comprising a compound described herein may be adapted for oral, intravenous, topical, intraperitoneal, nasal, buccal, sublingual, or subcutaneous administration, or for administration via the respiratory tract in the form of, for example, an aerosol or an air-suspended fine powder, or, for administration via the eye, intra-ocularly, intravitreally or corneally.

T In some embodiments, the pharmaceutical composition comprising a compound described herein may be in the form of, for example, tablets, capsules, powders, solutions for injection, solutions for spraying, ointments, transdermal patches or suppositories,

Methods of Treatment

Some aspects of the invention relate to the use of the compounds described herein or the composition described herein for us in the treatment of a disorder relating to the binding of a galectin to a ligand. In some embodiments, galectin is galectin-3.

Some aspects of the invention relate to the method of treating various disorders relating to the binding of a galectin to a ligand. In some embodiments, the methods comprise administering in a subject in need thereof a therapeutically effective amount of at least one compound described herein. In some embodiments, the subject in need thereof is a human having high levels of galectin-3. Levels of galectin, for example galectin-3 can be quantified using any methods known in the art.

In some embodiments, the disorder is an inflammatory disorder, for example inflammatory bowel disease, Crohn's disease, multiple sclerosis, Systemic Lupus Erythematosus, ulcerative colitis.

In some embodiments, the disorder is fibrosis, for example liver fibrosis, pulmonary fibrosis, kidney fibrosis, heart fibrosis or fibrosis of any organ compromising the normal function of the organ.

In some embodiments, the disorder is cancer.

In some embodiments, the disorder is an autoimmune disease such as rheumatoid arthritis and multiple sclerosis.

In some embodiments, the disorder is heart disease or heart failure.

In some embodiments, the disorder is a metabolic disorder, for example diabetes.

In some embodiments, the disorder relating is pathological angiogenesis, such as ocular angiogenesis, disease or conditions associated with ocular angiogenesis and cancer.

In some embodiments, the compounds of the invention comprises pyranosyl and/or furanosyl structures conjugated through an amide or sulfonamide type linkage to organic substitutions and are designated as "GalactoAmides" and/or "GalactoSulfonamides" with the general structures R'-Gal-AM-R" where the "AM" is an "amide" or "sulfonamide" type linkage with R' and R" are organic substituents.

In some embodiments, the compound comprises of functional galactose like pyranosyl and/or furanosyl structures linked through the anomeric carbon of the pyranosyl and/or furanosyl by "AM" type linkage to an organic substituent. As used herein the "AM" linkage is not limited to simple amide and can be any of the following linkages: N'-methylamide, sulfonamide, C-amide, O-Succinimide, Acetohydrazide, bemethly amide, N-ethylbenzene-amide, N-ethylamide, N-methoxypropane-amide, N-methoxypropanolamide, methyl-sulfur or sullfon linker or any combinations of the foregoing.

In some embodiments, the organic substituents are specific aromatic substitutions linked to the galactose core or the "AM" linker of the anomeric carbon of the pyranosyl and/or furanosyl structures. Such aromatic substitutions can enhance the interaction of the compound with amino acid residues (e.g. Arginine, Tryptophan, Histidine, Glutamic acid etc. . . . ) composing the carbohydrate-recognitiondomains (CRD) of the lectins or with amino acid residues in the CRD neighborhood and thus strengthen the association and binding specificity.

In some embodiments, the organic substituents comprises monosaccharides, disaccharides, oligosaccharides or a heteroglycoside such as iminosugar or thiosugar carbohydrates with nitrogen or sulfur atoms replacing the Oxygen and bound to the "amide" linker on the anomeric carbon of the galactose core.

In some embodiments, the compound is a symmetric digalactoside, wherein the two galactosides are bound by an "amide" linker. Yet in other embodiments, the compound can be comprised of asymmetric carbohydrates. For example, each of the galactoside can have different aromatic or aliphatic substitutions or heterotatoms derivatives of the galactose where the C5 oxygen is replaced with S (5-Thio-D-galactose) or N (5-imino-D-galactose).

Without being bound to the theory, it is believed that the compounds containing the "Amide" based linker containing molecules render the compounds metabolically stable while maintaining the chemical, physical and allosteric characteristics for specific interaction with lectins or galectins known to recognize carbohydrates. In some embodiments, the GalactoAmide and the GalactoSulfonamide of the invention are metabolically more stable than compounds having an O-glycosidic bond.

Aspect the invention relates to a compound or a pharmaceutically acceptable salt or solvate thereof:

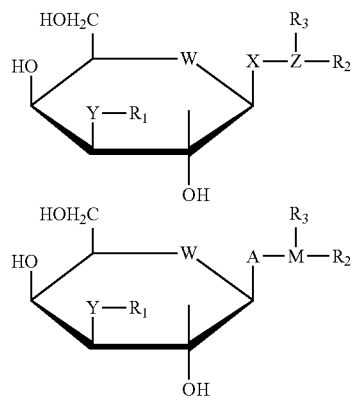

Wherein X is NH, NCH2, SNH, SO2, CH2, COH, Se, or amino acid,
Wherein Z is independently selected from a linkage consisting of C, NH, O, S, SO2, COH, Se to create the "AM" amide type linkage, e.g. amide, N'-methylamide, Sulfonamide, carbosulfon, Sulfonate, acetohydrazide linkage to the substitutions $R_2$ and $R_3$,
Wherein W is selected from the group consisting of O, N, S, CH2, NH, and Se;
Wherein Y is selected from the group consisting of O, S, C, NH, CH2, Se, and amino acid;
Wherein $R_1$, $R_2$, $R_3$, and $R_4$ are independently selected from the group consisting of H, CO, SO2, SO, PO2, PO, CH, and hydrophobic linear and cyclic hydrocarbons including heterocyclic substitutions of molecular weight of about 50-200 D.

In some embodiments, the AM linkage comprise Se or Se—Se bond and one or more atoms such as C or N. In some embodiments, Se can be directly linked to the anomeric Carbon and linked to C, N or O. In some embodiments, Se can be in the second position and C or N are linked to the anomeric carbon.

In some embodiments, the hydrophobic linear and cyclic hydrocarbons can comprise one of: a) an alkyl group of at least 4 carbons, an alkenyl group of at least 4 carbons, an alkyl group of at least 4 carbons substituted with a carboxy group, an alkenyl group of at least 4 carbons substituted with a carboxy group, an alkyl group of at least 4 carbons substituted with an amino group, an alkenyl group of at least 4 carbons substituted with an amino group, an alkyl group of at least 4 carbons substituted with both an amino and a carboxy group, an alkenyl group of at least 4 carbons substituted with both an amino and a carboxy group, and an alkyl group substituted with one or more halogens, b) a phenyl group substituted with at least one carboxy group, a phenyl group substituted with at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group, c) a naphthyl group, a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted With at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group, d) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and a heteroaryl group substituted with at least one substituted carbonyl group, and e) a saccharide, a substituted saccharide, D-galactose, substituted D-galactose, C3-[1,2,3]-triaZol-1-yl-substituted D-galactose, hydrogen, an alkyl group, an alkenyl group, an aryl group, a heteroaryl group, and a heterocycle and derivatives; an amino group, a substituted amino group, an imino group, or a substituted imino group.

EXAMPLES

Example 1

Compound Inhibition of Galectin Binding to Physiologic Ligands

Galectin proteins, including but not limited to galectin-3 and galectin-1, have multiple biologically relevant binding ligands in mammalian species, including but not limited to rodents, primates, and humans. Galectins are carbohydrate-binding proteins that bind to glycoproteins with 8-galactoside-containing sugars. The result of binding of galectin proteins to these ligands results in a plethora of biological effects in and on cells and in tissues and whole organisms including regulating cell survival and signaling, influencing cell growth and chemotaxis, interfering with cytokine secretion, mediating cell-cell and cell-matrix interactions or influencing tumor progression and metastasis. Additionally, changes in normal expression of galectin proteins are responsible for pathological effects in multiple diseases, including but not limited to inflammatory, fibrotic and neoplastic diseases. (See FIGS. 8B, 9)

Figure 5A:
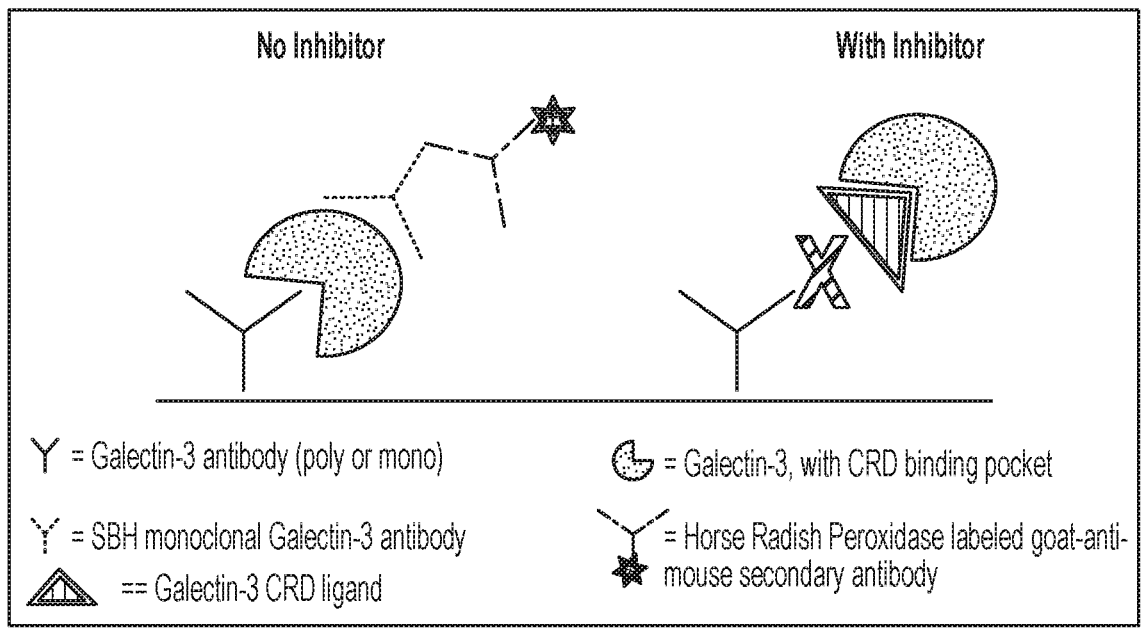
FIG. 5A depicts the inhibition of galectin binding moiety using a specific anti-Galectin-3 monoclonal antibodies binding assay (ELISA format) according to some embodiments.
Figure 7A:
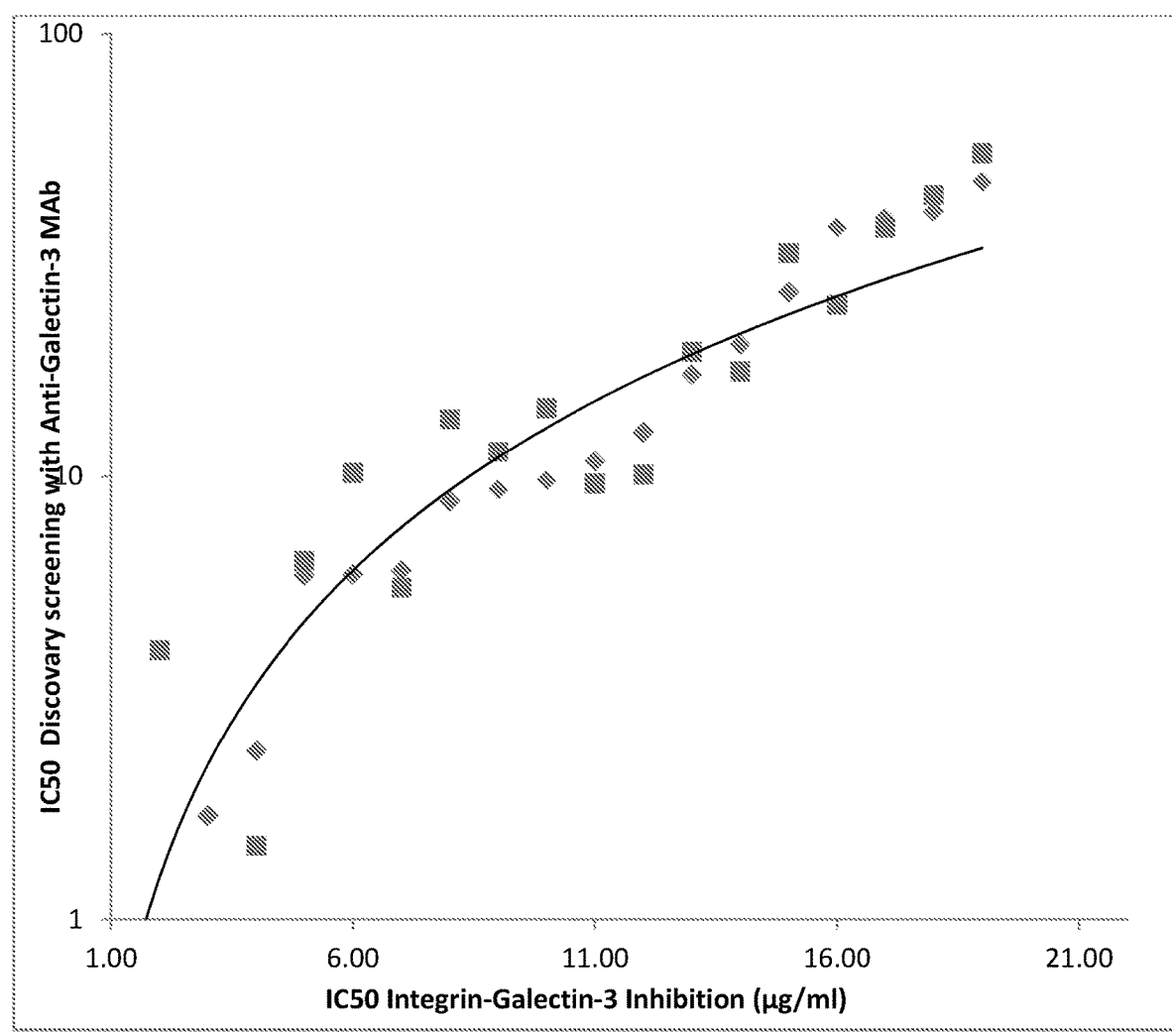
FIG. 7A depicts correlation between the ELISA MAb and the ELISA Integrin assays for multiple GalactoAmides derivatives.

To screen galectin-3 functional activity and neutralizing effects of compounds of the invention, specific monoclonal antibodies have been selected and analytical assay using an ELISA format was developed as illustrate in FIG. 5A. The inhibitory comparison of this antibodies based ELISA with the inhibition of Integrin amB2 to galectin-3 had good regression factor of better than 0.95 as presented in FIG. 7A and FIG. 7B.

Compounds described herein are designed to bind to the carbohydrate recognition domain of galectin proteins, including but not limited to galectin-3, and disrupt interactions with biologically relevant ligands. They are intended to inhibit the function of galectin proteins that may be involved in pathological processes at normal levels of expression or in situations where they are increased over physiological levels.

Some of the ligands for galectin proteins that are important in normal cellular function and pathology in disease include, but are not limited to, TIM-3 (T cell immunoglobulin mucin-3)), CD8, T cell receptor, integrins, galectin-3 binding protein, TGF-β receptor, laminins, fibronectins, BCR (B cell receptor, CTLA-4 (cytotoxic T-lymphocyte-associated protein-4), EGFR (Epidermal growth factor receptor), FGFR (fibroblast growth factor receptor), GLUT-2 (glucose transporter-2), IGFR (insulin-like growth factor receptor), various interleukins, LPG (lipophosphoglycan), MHC (major histocompatibility complex), PDGFR (platelet-derived growth factor receptor), TCR (T cell receptor), TGF-β (transforming growth factor-β), TGFβR (transforming growth factor-β receptor, CD98, Mac3 antigen (Lysosome-associated membrane protein 2 (LAMP2) also known as CD107b (Cluster of Differentiation 107b)).

Figure 5B:
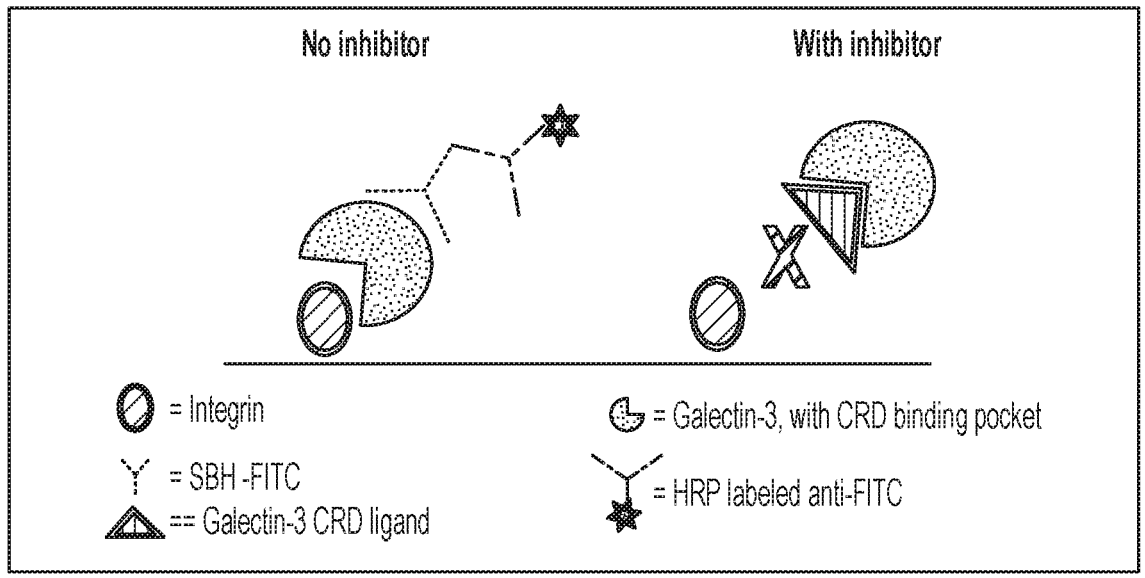
FIG. 5B depicts the inhibition of galectin using an integrin-galectin-3 functional assay (CRD ELISA format) according to some embodiments.

Experiments have been performed to evaluate the physical interaction of galectin proteins with these various biological ligands mediating cellular functions. The experiments were designed to evaluate the interaction between various galectin-3 ligands and determine whether compounds described herein are able to inhibit these interactions, as analytical assays format shown in FIG. 5B.

Figure 8B:
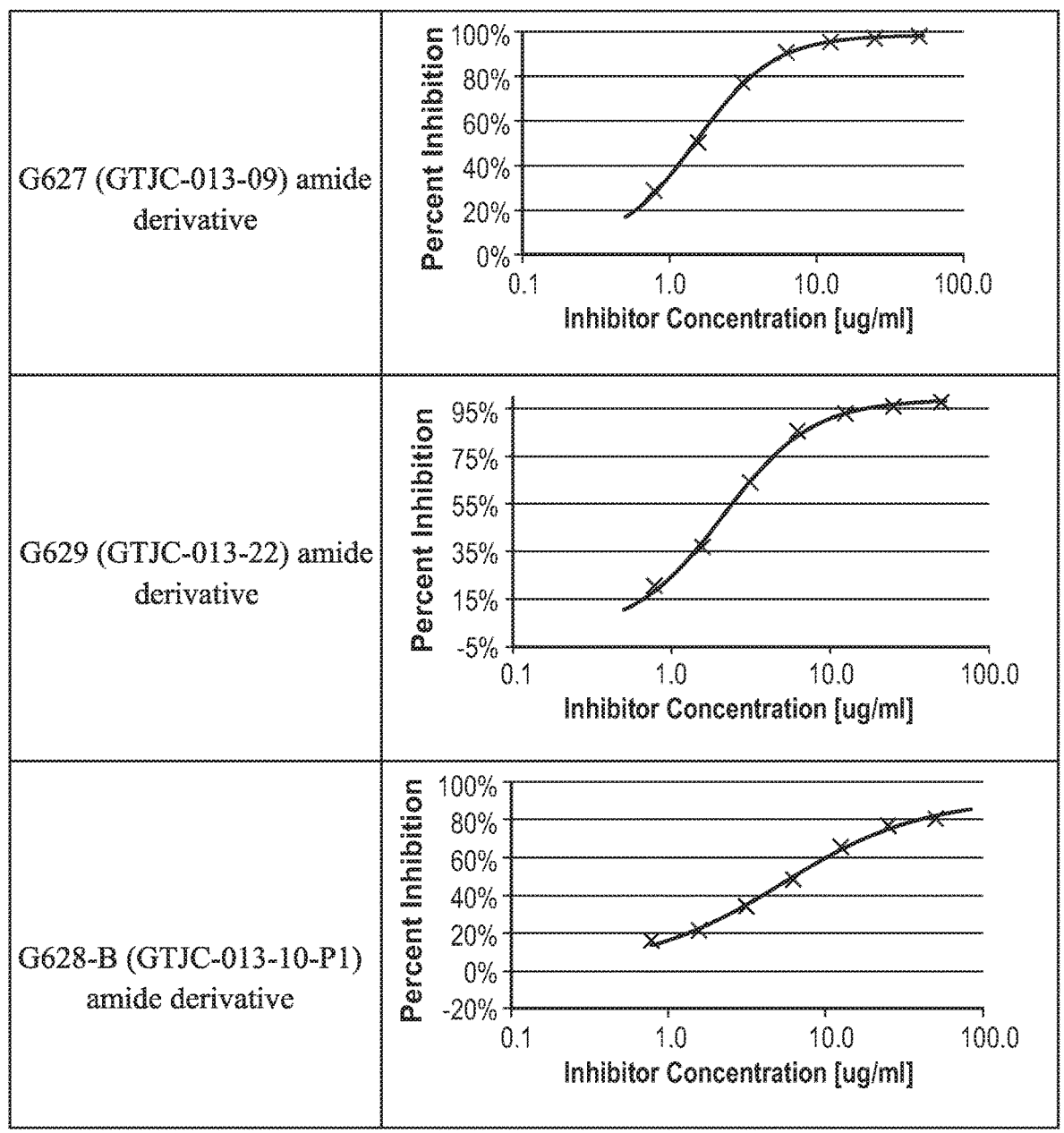
FIG. 8B shows examples of target inhibition of Galectin-3 interaction with Integrin-aMB2 by compounds according to some embodiments of the invention (600 series).
Figure 8B:
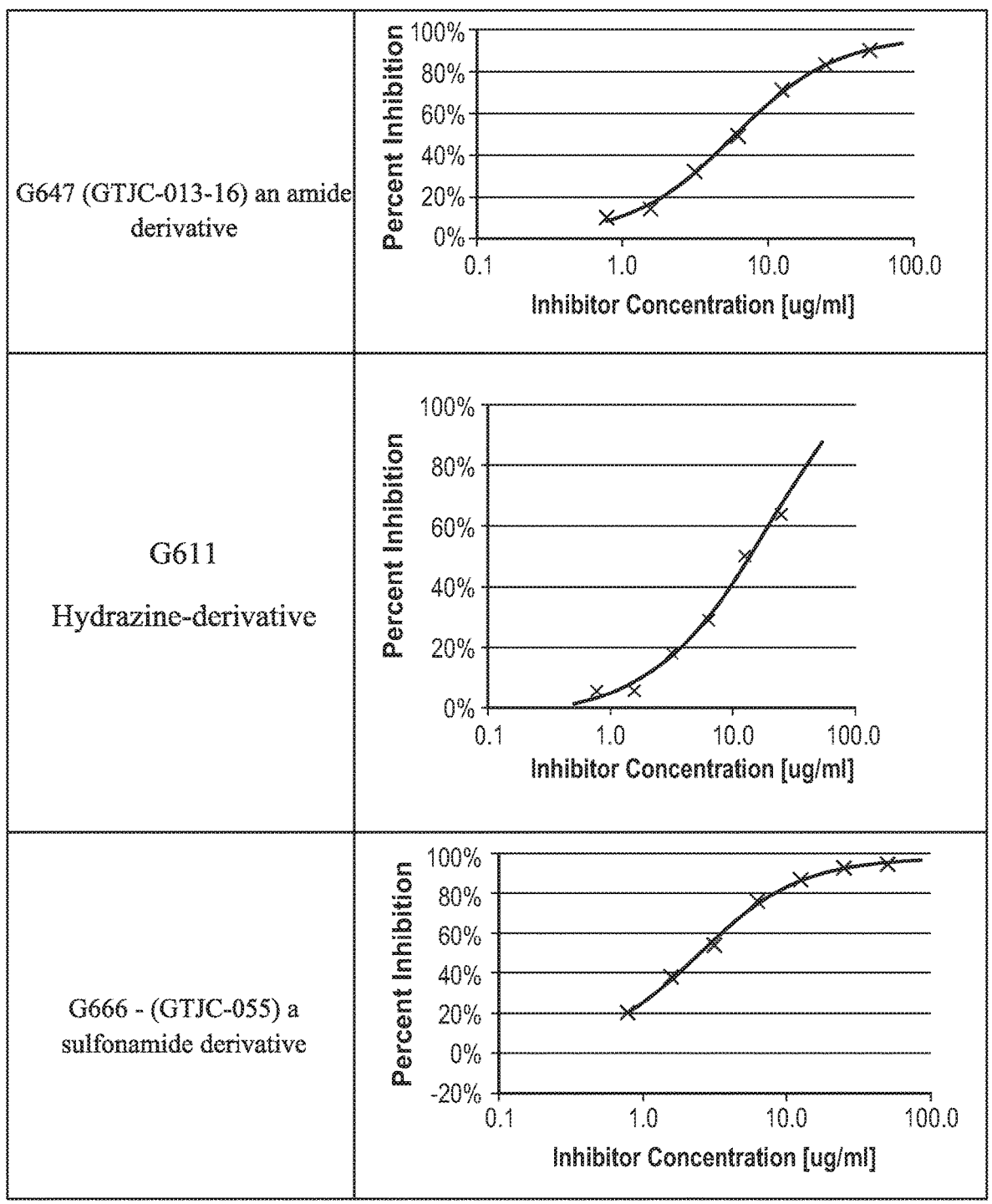
Figure 9:
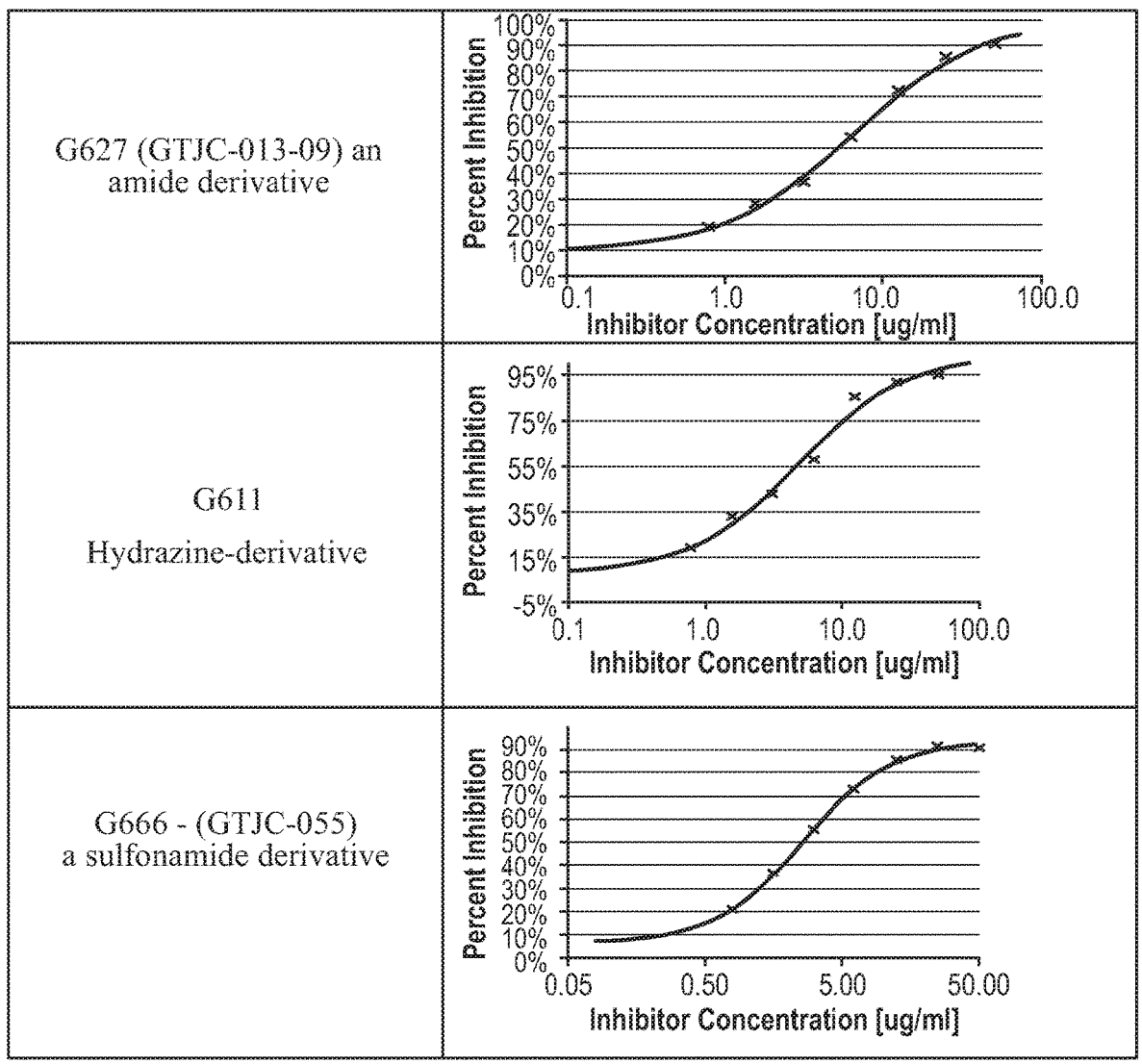
FIG. 9 shows examples of target inhibition according to some embodiments by compounds of the invention (600 series) of Galectin-3 interaction with Integrin-aVB6.

Using these assays format, the compounds described herein inhibit the interaction of galectin proteins with their ligands, including but not limited to various integrin molecules (αVβ3, αVβ6, αMβ2, α2β3, and others) with IC50's in the range of about 5 ηM to about 40 µM. In some embodiments, the IC50 is about from 5 nM to about 20 nM. In some embodiments, the IC50 is from about 5 nM to about 100 nM. In some embodiments, the IC50 is from about 10 nM to about 100 nM. In some embodiments, the IC50 is from about 50 nM to about 5 µM. In some embodiments, the IC50 is from about 0.5 µM to about 10 µM. In some embodiments, the IC50 is from about 5 µM to about 40 µM as listed in FIG. 7A and FIG. 7B). Further examples of the inhibition effect of exemplary compounds of the invention of galectin-3 interaction with Integrin amB2 are shown in FIG. 8B and of the inhibition of galectin-3 with integrin aVM6 are shown in FIG. 9.

Example 2

Compound Inhibition of Galectin Binding to Labeled Probes

Fluorescein-labeled probes have been developed which bind to galectin-3 and other galectin proteins and these probes have been used to establish assays that measure the binding affinity of ligands for the galectin proteins using Fluorescence Polarization (Sörme P, et al. Anal Biochem. 2004 Nov. 1; 334(1):36-47).

Compounds described herein avidly bind to galectin-3, as well as other galectin proteins, using this assay format (FIG. 6B) and displace the probe with high affinity, with $IC_{50}$'s (concentration at 50% inhibition) of between about 5 nM to about 40 µM. In some embodiments, the IC50 is about from 5 nM to about 20 nM. In some embodiments, the IC50 is from about 5 nM to about 100 nM. In some embodiments, the IC50 is from about 10 nM to about 100 nM. In some embodiments, the IC50 is from about 50 nM to about 5 µM. In some embodiments, the IC50 is from about 0.5 µM to about 10 µM. In some embodiments, the IC50 is from about 5 µM to about 40 µM.

Figure 8A:
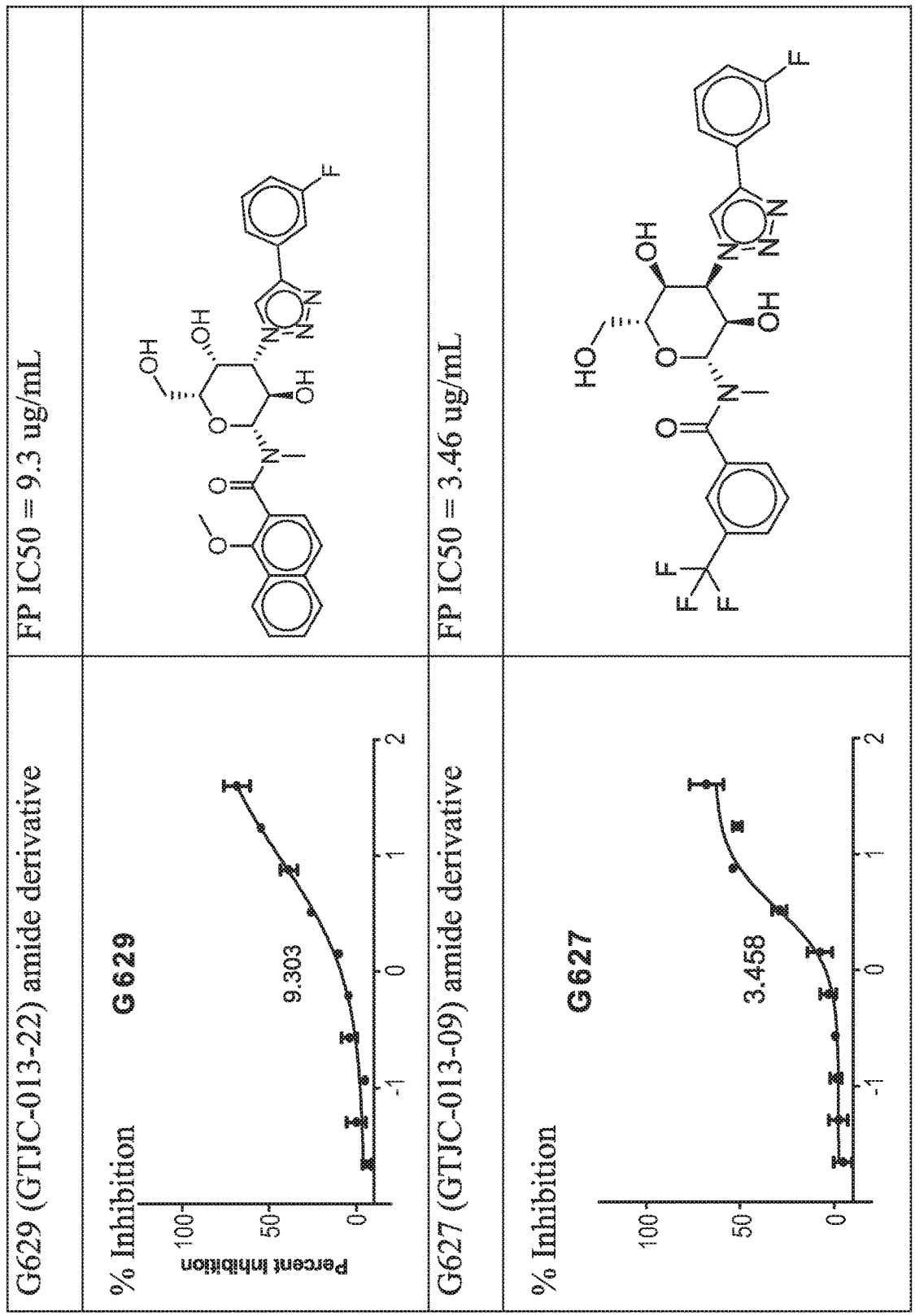
FIG. 8A shows reduction of Fluorescent Polarization of a CRD specific binding of fluorescent ligand by compounds (600 series) according to some embodiments.
Figure 8A:
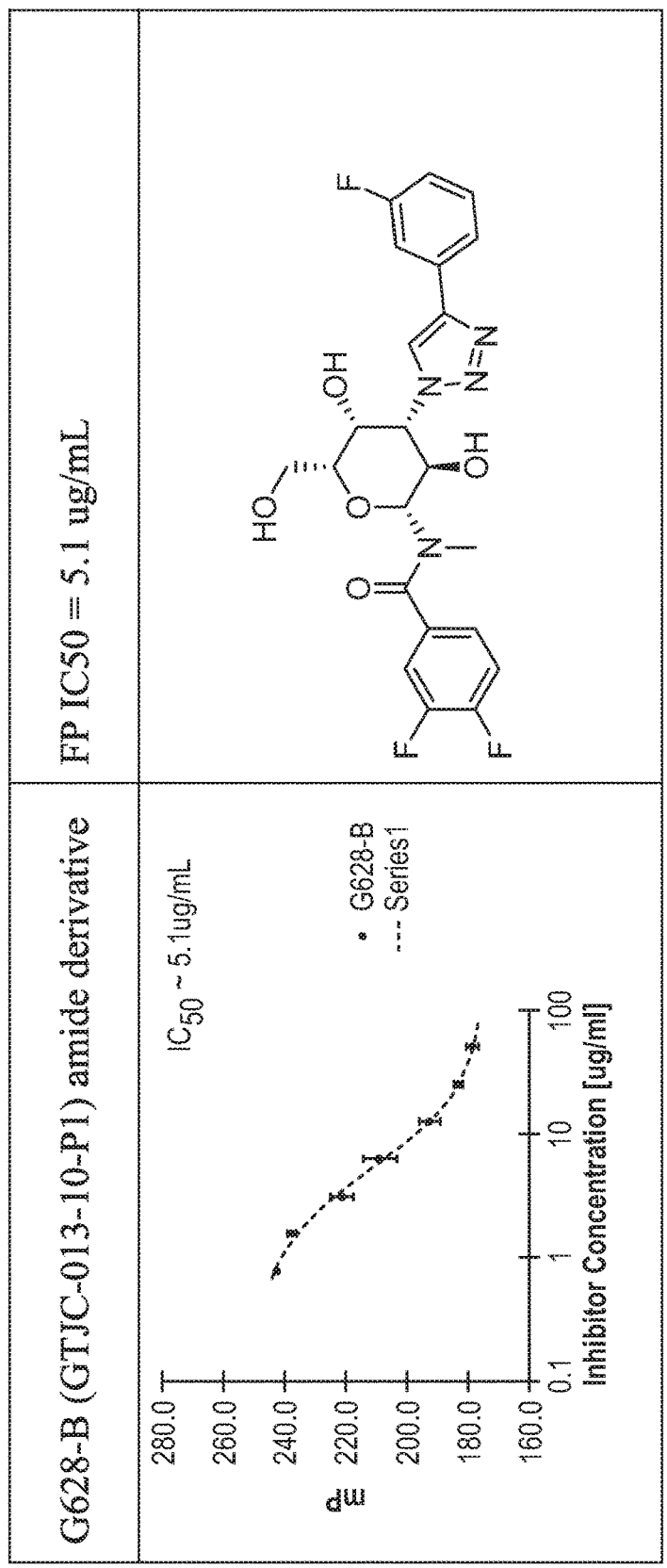

Exemplary compounds of the invention were synthesized (FIG. 4) and showed an inhibitory activity in the Fluorescent polarization assay (FIG. 8A).

Example 3

Compound Inhibition of Galectin Binding Using FRET Assay

Figure 6A:
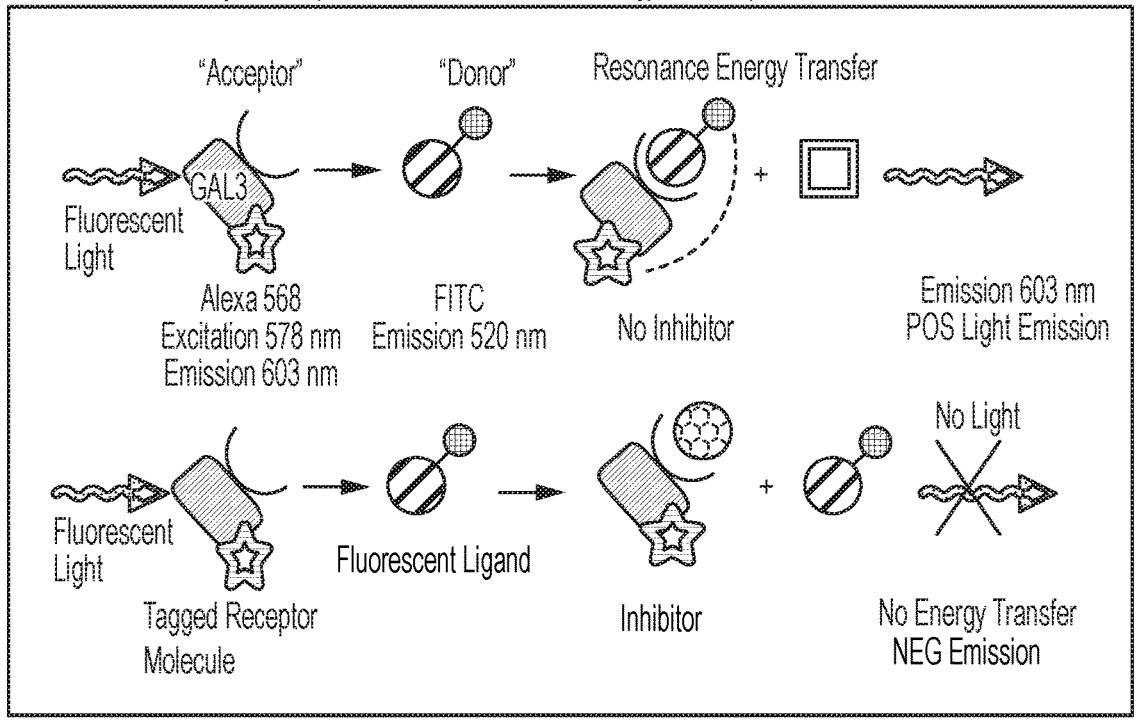
FIG. 6A depicts a Fluorescence Resonance Energy Transfer analytical assay (FRET Format) for screening anti-galectin active compounds according to some embodiments.
Figure 6B:
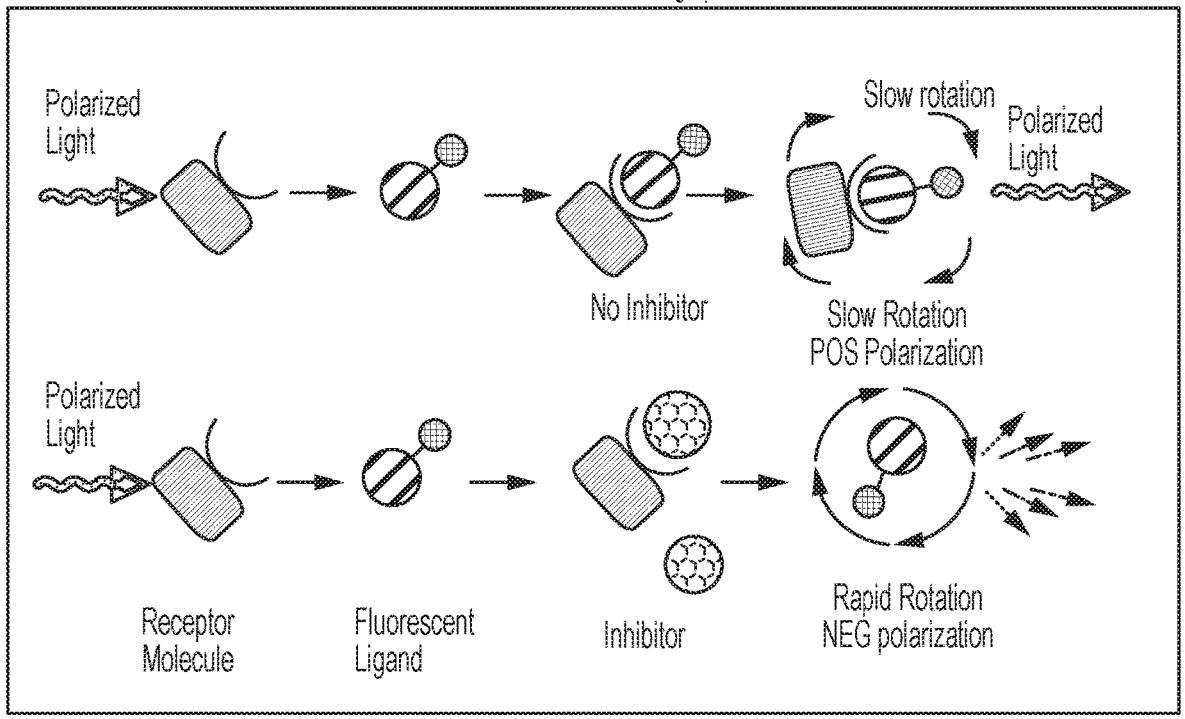
FIG. 6B depicts a Fluorescent Polarization Assay Format which detects compounds that bind specifically to the CRD according to some embodiments.

FRET assay (fluorescent resonance energy transfer) assays were developed for evaluating the interaction of galectin proteins, including but not limited to galectin-3, with a model fluorescent-labeled probe (see FIG. 6A). Using this assay, compounds described herein avidly bind to galectin-3, as well as other galectin proteins, using this assay and displace the probe with high affinity, with $IC_{50}$'s (concentration at 50% inhibition) of between about 5 nM to about 40 µM. In some embodiments, the IC50 is about from 5 nM to about 20 nM. In some embodiments, the IC50 is from about 5 nM to about 100 nM. In some embodiments, the IC50 is from about 10 nM to about 100 nM. In some embodiments, the IC50 is from about 50 nM to about 5 µM. In some embodiments, the IC50 is from about 0.5 µM to about 10 µM. In some embodiments, the IC50 is from about 5 µM to about 40 µM.

Example 4

Compound Binding to Amino Acid Residues in Galectin Proteins

Heteronuclear NMR spectroscopy is used to evaluate the interaction of compounds described herein with galectin molecules, including but not limited to galectin-3, to assess the interaction residues on the galectin-3 molecule.

Uniformly $^{15}$N-labeled Gal-3 is expressed in BL21 (DE3) competent cells (Novagen), grown in minimal media, purified over a lactose affinity column, and fractionated on a gel filtration column, as described previously for production of Gal-1 (Nesmelova I V, Pang M, Baum L G, Mayo K H. 1H, 13C, and 15N backbone and side-chain chemical shift assignments for the 29 kDa human galectin-1 protein dimer. Biomol NMR Assign 2008 December; 2(2):203-205).

Uniformly $^{15}$N-labeled Gal-3 is dissolved at a concentration of 2 mg/ml in 20 mM potassium phosphate buffer at pH 7.0, made up using a 95% H$_2$O/5% D$_2$O mixture. $^1$H-$^{15}$N HSQC NMR experiments are used to investigate binding of a series of compounds described herein. $^1$H and $^{15}$N resonance assignments for recombinant human Gal-3 were previously reported (Ippel H, et al. (1)H, (13)C, and (15)N backbone and side-chain chemical shift assignments for the 36 proline-containing, full length 29 kDa human chimera-type galectin-3. Biomol NMR Assign 2015 April; 9(1):59-63.).

NMR experiments are carried out at 30° C. on Bruker 600 MHz, 700 MHz or 850 MHz spectrometers equipped with H/C/N triple-resonance probes and x/y/z triple-axis pulse field gradient units. A gradient sensitivity-enhanced version of two-dimensional $^1$H-$^{15}$N HSQC is applied with 256 (t1)×2048 (t2) complex data points in nitrogen and proton dimensions, respectively. Raw data are converted and processed by using NMRPipe and were analyzed by using NMRview.

These experiments show differences between compounds described herein and galactose in the binding residues in the carbohydrate binding domain of galectin-3.

Example 5

Cellular Activity of Cytokine Activity Related to Galectin Binding Inhibition

Example 1 describes the ability of compounds of this application to inhibit the binding of physiologic ligands to galectin molecules. In the experiments of this example, the functional implications of those binding interactions are evaluated.

One of the interactions with galectin-3 that is inhibited by the compounds described herein was TGF-β receptor. Therefore, experiments are done to evaluate the effect of compounds on TGR-β receptor activity in cell lines. Various TGF-β responsive cell lines, including but not limited to LX-2 and THP-1 cells, are treated with TGF-β and response of the cells is measured by looking at activation of second messenger systems, including but not limited to phosphorylation of various intracellular SMAD proteins. After establishing that TGF-β activates the second messenger systems in the various cell lines, the cells are treated with compounds described herein. This experiments show that these compounds inhibit TGF-β signaling pathways, confirming that the binding interaction inhibition described in Example 1 has a physiological role in cellular models.

Cellular assays are also performed to evaluate the physiological significance of inhibiting the interaction of galectin-3 with various integrin molecules. Cell-cell interaction studies are performed using monocytes binding to vascular endothelial cells, as well as other cell lines. Treatment of cells with compounds described herein is found to inhibit these integrin-dependent interactions, confirming that the binding interaction inhibition described in Example 1 has a physiological role in cellular models.

Cellular motility assays are performed to evaluate the physiological significance of inhibiting the interaction of galectin-3 with various integrin and other cell surface molecules defined in Example 1. Cellular studies are performed using multiple cell lines in a semi-permeable membrane separated well apparatus. Treatment of cells with compounds described herein is found to inhibit cellular motility, confirming that the binding interaction inhibition described in Example 1 has a physiological role in cellular models.

Example 6

In-Vitro Inflammatory Model (a Monocyte Based Assay)

Figure 10A:
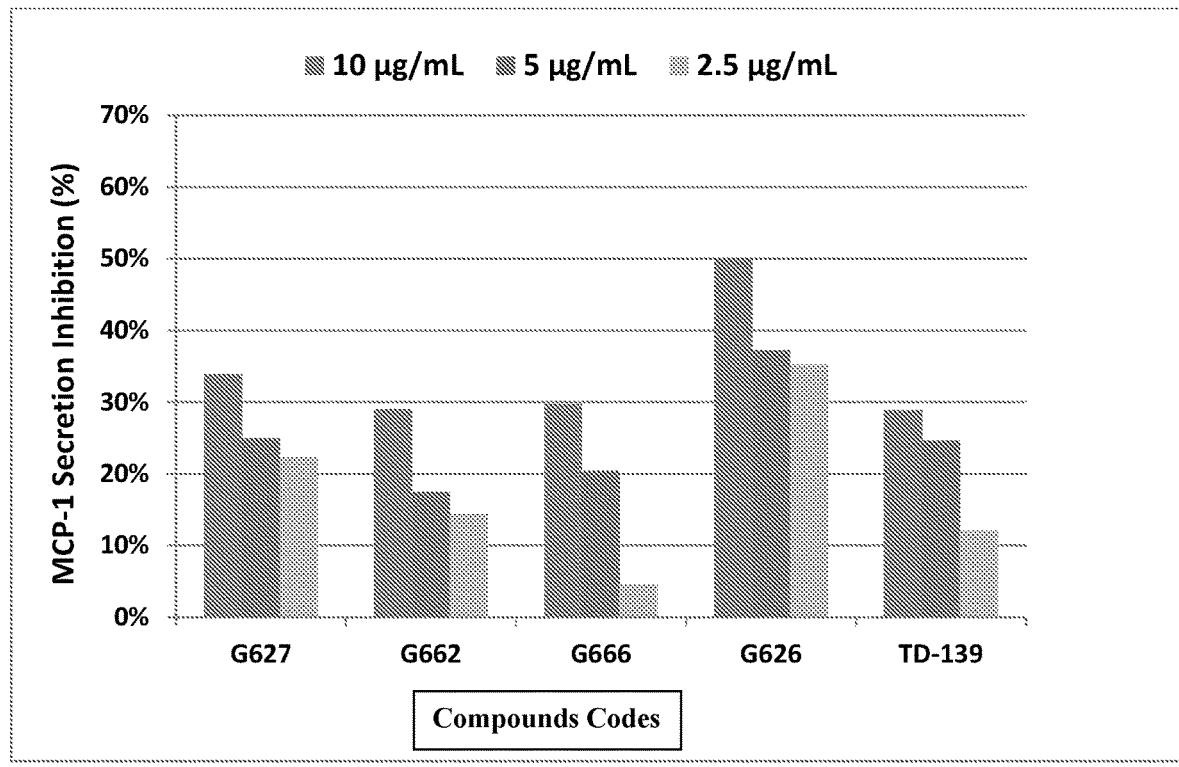
FIGS. 10A and 10B show examples of Inhibition of the cytokine MCP-1 secretion by Inflammatory Macrophages (LPS stressed THP-1 cell culture) by compounds and compound IC50 (600 series) according to some embodiments of the invention.

A model of macrophage polarization is set up, starting from THP-1 monocytes culture which is differentiated into inflammatory macrophages using PMA (Phorbol 12-myristate 13-acetate) for 2-4 days. Once differentiated (M0 macrophages), the macrophages are induced with LPS or LPS and IFN-gamma for macrophage activation (M1) to inflammatory stage for 1-3 days. Array of cytokines and chemokines are analyzed to confirm the polarization of THP-1-derived macrophages to inflammatory stage. The impact of the anti-galectin-3 compounds on macrophage polarization is assessed first by monitoring cell viability using a colorimetric method (using a tetrazolium reagent) to determine the number of viable cells in proliferation or cytotoxicity assays (Promega, The CellTiter 96® AQueous One Solution Cell Proliferation Assay which contains a novel tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES)) and inflammatory stage evaluated by a quantitatively measure of the chemokine Monocyte Chemoattractant Protein-1 (MCP-1/CCL2), a key protein that regulates migration and infiltration of monocytes/macrophages in cellular process of inflammation. Follow-up testing for the expression and secretion of other cytokines and chemokines are done for leading active compounds. Results are expressed in percentage reduction of MCP-1 as shown in FIG. 10A for compounds according to some embodiments.

Figure 10B:
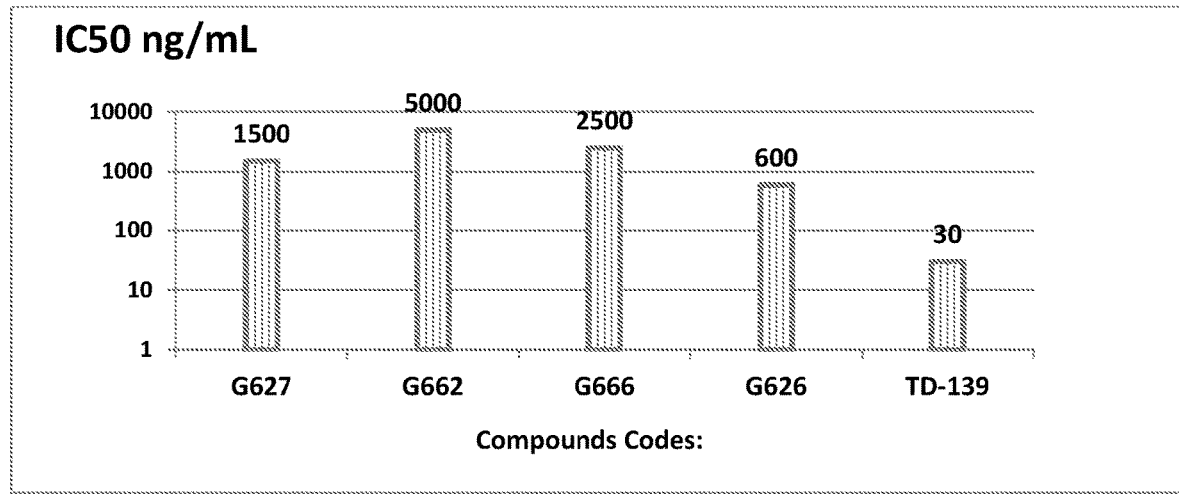

Example of method steps:
1) THP-1 cells were cultured in media containing Gentamicin
2) THP-1 cells are transfer to wells in a 96 well plate 2,000 cells/well for 2 days incubation in assay media containing 5-50 ng/ml PMA
3) Serial dilution of test compounds is made in LPS (1-10 ng/ml) containing media
4) To each well 100 ml of compounds/LPS solution is added to a final assay volume of each well of 200 ml which contains also Gentamicin and 5-20 ng/ml PMA
5) Cells are incubated up to 8 days.
6) Every other day samples of 20-60 ul are removed for biomarker assays
7) At termination 15 ml of Promega Substrate CellTiter 96 Aqueous One Solution is prepared and added to each well to monitor cytotoxicity (at 490 nm)
8) For cellular biomarkers evaluation the cells are washed 1×PBS and extracted with 200 ul of Lysis buffer for 1 hour. Extract is spinned down 10 minutes and 120 ul sample is removed from top. All samples are kept at −70 C until testing. (See FIG. 10)

Example 7

Cell Culture Fibrogenesis Model

Experiments are performed with fibrogenic stellate cell cultures, including but not limited to LX-2 cells, to evaluate the cellular effect of compounds herein. LX-2 cells are activated in culture using serum deprived media and media spiked with different percentages of THP-1 cell conditioned media. Activation of LX-2 cells is monitored by various well defined markers, including but not limited to TIMP-1. Demonstrable LX-2 cell activation is evident by 24 hours after treatment. The treatment of cells with compounds described herein is found to inhibit activation, confirming a physiological role in cellular models.

Example 8

In Vivo Animal Models of Liver Fibrosis

NASH Mouse Fibrosis Model

The NASH model uses male newborn mice [C57BL/6J mice]. The disease is induced by a single subcutaneous injection of streptozotocin (Sigma, St. Louis, Mo.) solution 2 days after birth which induced diabetes. After four weeks of age a high fat diet (HFD, 57% of kcal from fat) is introduced for 12 and up to 16 weeks as demonstrate in the time line enclosed graph. Vehicle and test substances at the various doses are administered orally or SQ or intravenously weekly and calculated as mg/kg body weight. Animal care follows protocols accordance with accepted Guidelines for Animal Use. Animals are fasted for 3 hours before sacrifice which is performed by exsanguination through direct cardiac puncture under ether anesthesia.

Randomization of mice into treatment groups is done prior to treatment based on the plasma ALT levels and body weight. At minimum 3 treatment groups are in a study.

Group 1: Twelve normal mice are fed with a normal diet ad libitum without any treatment, Group 2: Twelve NASH mice are intravenously administered vehicle (0.9% sodium chloride) once weekly from 6 to 12 weeks of age Group 3: Twelve NASH mice are intravenously administered test article in vehicle (0.9% sodium chloride) once weekly from 6 to 12 weeks of age Mice are sacrificed for the following 4 weeks of treatment The seleno-galactoside compounds described herein reduce live fibrosis as measured by collagen 10% to 80% versus the vehicle control or to almost normal collagen levels as established in group 1.

General Biochemical Tests:

Diabetic fast glucose is measured in whole blood samples using for example G Checker (Sanko Junyaku Co. Ltd., Japan).

Liver functions are evaluated in Plasma for levels of AST, ALT, total bilirubin, creatinine, and TG are measured by example FUJI DRY CHEM 7000 (Fuji Film, Japan).

Liver biochemistry: To quantify liver hydroxyproline content, a quantitative assessment of collagen content, frozen liver samples (40-70 mg) are processed by a standard alkaline-acid hydrolysis method and hydroxyproline content is normalized to total liver proteins.

Total liver lipid-extracts are obtained from caudate lobes by Folch's method and liver TG levels are measured using the Triglyceride E-test (Wako, Japan).

Histopathological and immunohistochemical analyses liver sections are cut from paraffin blocks of liver tissue prefixed in Bouin's solution and stained with Lillie-Mayer's Hematoxylin (Muto Pure Chemicals, Japan) and eosin solution (Wako, Japan).

To visualize collagen deposition, Bouin's fixed liver sections are stained using picro-Sirius red solution (Waldeck GmbH & Co. KG, Germany). NAFLD Activity score (NAS) is also calculated according to established criteria.

Immunohistochemistry for SMA, F4/80, Galectin-3, CD36 and iNOS can be estimated from each positive area as indication for the extent of inflammation and fibrosis.

Rat Fibrosis/Cirrhosis Model (TAA Model):

These experiments use male Sprague-Dawley rats between 160 and 280 g obtained from animal research facility (Jackson Laboratory) which are maintained according to the Guide for the Care and Use of Laboratory Animals (Institute of Laboratory Animal Resources, 1996, Nat. Acad. Press) and Institutional Animal Care and Use committee (IACUC). At the end of experiments, animals are euthanized under phenobarbital anesthesia.

After an acclimation period of two weeks, an eight week induction period is initiated, in which all rats are subjected to intraperitoneal (IP) injections Thioacetamide (TAA, Sigma Chemical Co., St. Louis, Mo., USA) of sterile solutions of dissolved in 0.9% saline, administered by IP injection twice or trice weekly with initial week dosage of 450 mg/kg/wk, followed by seven weeks regimen of 400 mg/kg/wk body weight. To assess for the progression of fibrosis two rats are euthanized at weeks 4 and 8, and the liver examined histologically. To develop cirrhosis animals are administered TAA intraperitoneally (IP) up to 11-12 weeks, for fibrosis 8 weeks are enough. Treatment is for 4 weeks beginning in week 8, vehicle control group is administered 0.9% NaCl intraperitoneally twice weekly for four weeks. Experimental test articles are given intraperitoneally twice or once a week beginning in week 8 or 11 for fibrosis or cirrhosis respectively. At the end of the treatment period, rats are placed under anesthesia using isofluorane between 1-5% through inhalation and a laparotomy is performed. At the time of sacrifice, portal pressure is measured using a 16 G angiocatheter introduced into the portal vein to measure the height of a water column. The liver is removed, weighed, and pieces from the largest lobes are used for further analysis. The spleen is also removed and weighed before being discarded.

Representative histology of Sirius red stained liver sections from experiment shows a 20% reduction in mean collagen which is statistical acceptable for anti-fibrosis effect. Strands of bridging fibrosis indicate advance fibrosis stage (these are strands of collagen fibers).

Biochemical Tests:

As in the NASH model various diagnostic tests are done to evaluate the extend of liver damage due to the fibrosis:

Liver functions are evaluated in Plasma for levels of AST, ALT, total bilirubin, creatinine, and TG are measured by example FUJI DRY CHEM 7000 (Fuji Film, Japan).

Liver biochemistry: To quantify liver hydroxyproline content, a quantitative assessment of collagen content, frozen liver samples (40-70 mg) are processed by a standard alkaline-acid hydrolysis method and hydroxyproline content is normalized to total liver proteins.

Total liver lipid-extracts are obtained from caudate lobes by Folch's method and liver TG levels are measured using the Triglyceride E-test (Wako, Japan).

Histopathological and immunohistochemical analyses liver sections are cut from paraffin blocks of liver tissue prefixed in Bouin's solution and stained with Lillie-Mayer's Hematoxylin (Muto Pure Chemicals, Japan) and eosin solution (Wako, Japan).

To visualize collagen deposition, Bouin's fixed liver sections are stained using picro-Sirius red solution (Waldeck GmbH & Co. KG, Germany). NAFLD Activity score (NAS) is also calculated according to established criteria.

Immunohistochemistry for SMA, F4/80, Galectin-3, CD36 and iNOS can be estimated from each positive area as indication for the extent of inflammation and fibrosis.

Bile Duct Models of Liver Fibrosis

These experiments are done to evaluate the efficacy of the compounds described herein on the fibrosis of the liver following bile duct ligation or treatment with drugs that cause biliary fibrosis. Animals treated with the compounds herein described show that liver fibrosis was reduced in comparison to vehicle controls.

Example 9

In Vivo Animal Models of Lung Fibrosis

These experiments are done to evaluate the efficacy of the compounds described herein on the prevention of bleomycin-induced pulmonary fibrosis. An untreated control group with intratracheal saline infusion consists of 10 mice. Bleomycin is administered by slow intratracheal infusion into the lungs of other groups on Day 0. On Days −1, 2, 6, 9, 13, 16 and 20, mice are dosed (iv, ip, subcut, or oral) once daily with vehicle or various doses of compounds described herein (iv, ip, subcut, or oral). Animals are weighed and evaluated for respiratory distress daily. On Day 21, all animals are euthanized and the wet weight of lungs is measured. Upon sacrifice, blood is collected via retro-orbital bleed for preparation of serum. The right lobe of the lung is snap frozen for subsequent hydroxyproline analysis while the left is insufflated and fixed in 10% formalin for histological analysis. The formalin-fixed lung is processed for routine histological evaluation.

Example 10

In Vivo Animal Models of Kidney Fibrosis

These experiments are done to evaluate the efficacy of the compounds described herein on the fibrosis of the kidney using models of unilateral ureteral ligation and diabetic nephropathy. Animals treated with various compounds herein show that kidney fibrosis is reduced in comparison to vehicle controls.

Example 11

In Vivo Animal Models of Cardiovascular Fibrosis

These experiments are done to evaluate the efficacy of the compounds described herein on the fibrosis of the heart and vessels using models of heart failure, atrial fibrillation, pulmonary hypertension, and atherosclerosis. Animals treated with various compounds herein show that cardiovascular fibrosis was reduced in comparison to vehicle controls.

Example 12

VEGF-A-Induced Angiogenesis

Vascular endothelial growth factors (VEGFs) signaling though VEGF receptor-2 (VEGFR-2) is the primary angiogenic pathway. Galectin proteins are important for the signaling pathway. Compounds described herein are able to inhibit neovascularization of mouse cornea in response to injury.

Example 13

Evaluation of Compound Absorption, Distribution, Metabolism, and Elimination

Compounds described herein are evaluated for physicochemical properties, including but not limited to solubility (Thermodynamic and Kinetic method), various pH changes, solubility in biorelevant medium (FaSSIF, FaSSGF, FeSSIF), Log D (Octanol/water and Cyclohexane/water), chemical stability in plasma, and blood partitioning.

Compounds described herein are evaluated for in vitro permeability properties, including but not limited to PAMPA (parallel artificial membrane permeability assay), Caco-2, and MDCK (wild type)

Compounds described herein are evaluated for animal pharmacokinetic properties, including but not limited to pharmacokinetics by various routes viz., oral, intravenous, intraperitoneal, subcutaneous in mice (Swiss Albino, C57, Balb/C), rats (Wistar, Sprague Dawley), rabbits (New Zealand white), dogs (Beagle), Cynomolgus monkeys, etc., tissue distribution, brain to plasma ratio, biliary excretion, and mass balance.

Compounds described herein are evaluated for protein binding, including but not limited to plasma protein binding (ultra Filtration and Equilibrium Dialysis) and microsomal protein binding.

Compounds described herein are evaluated for in vitro metabolism, including but not limited to cytochrome P450 inhibition, cytochrome P450 time dependent inhibition, metabolic stability, liver microsome metabolism, S-9 fraction metabolism, effect on cryopreserved hepatocyte, plasma stability, and GSH trapping.

Compounds described herein are evaluated for metabolite identification, including but not limited to identification in vitro (microsomes, S9 and hepatocytes) and in vivo samples.

Example 14

Synthesis of GalactoAmide and GalactoSulfonamides Compounds

Non-limiting examples of compounds according to some embodiments are shown in Table 1 and FIG. 4.

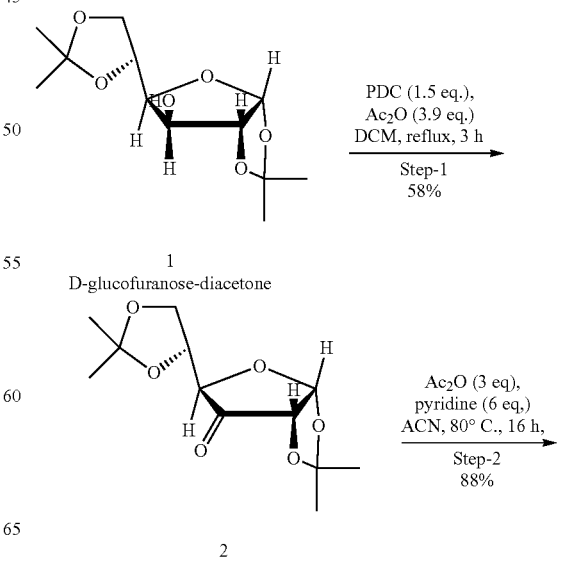

Figure 4A:
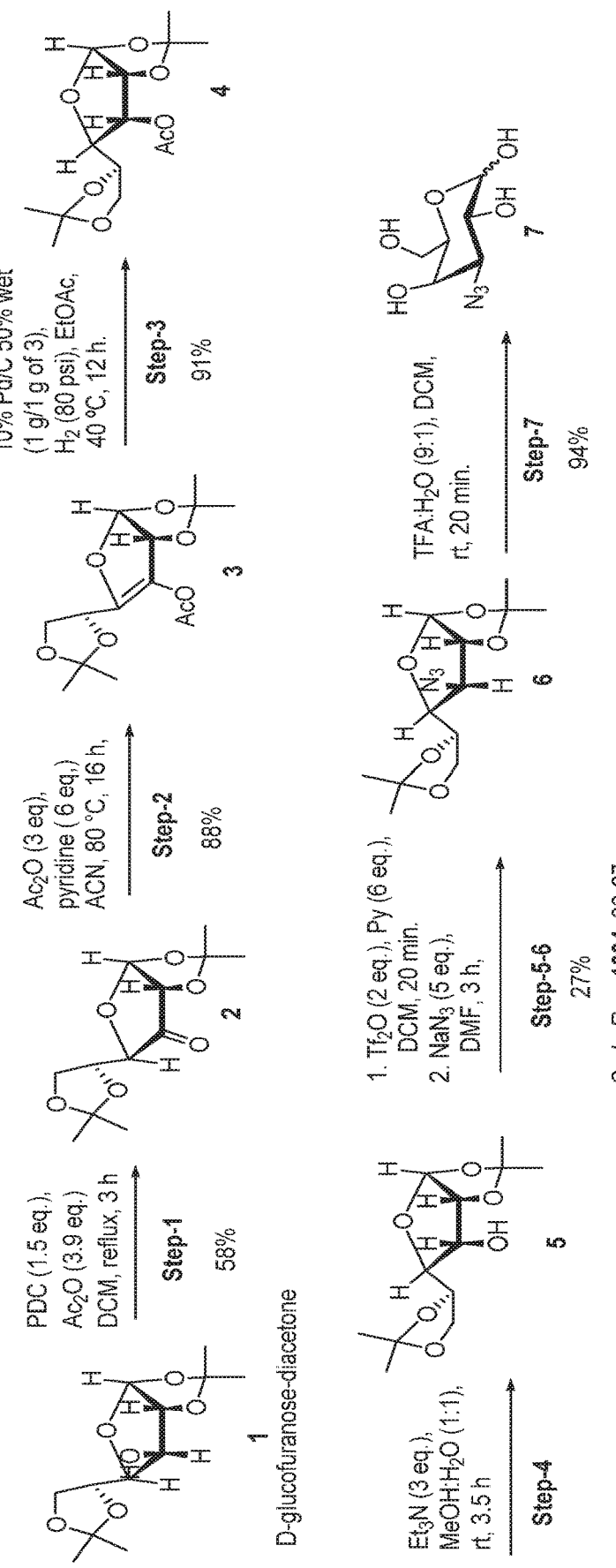
Figure 4A:
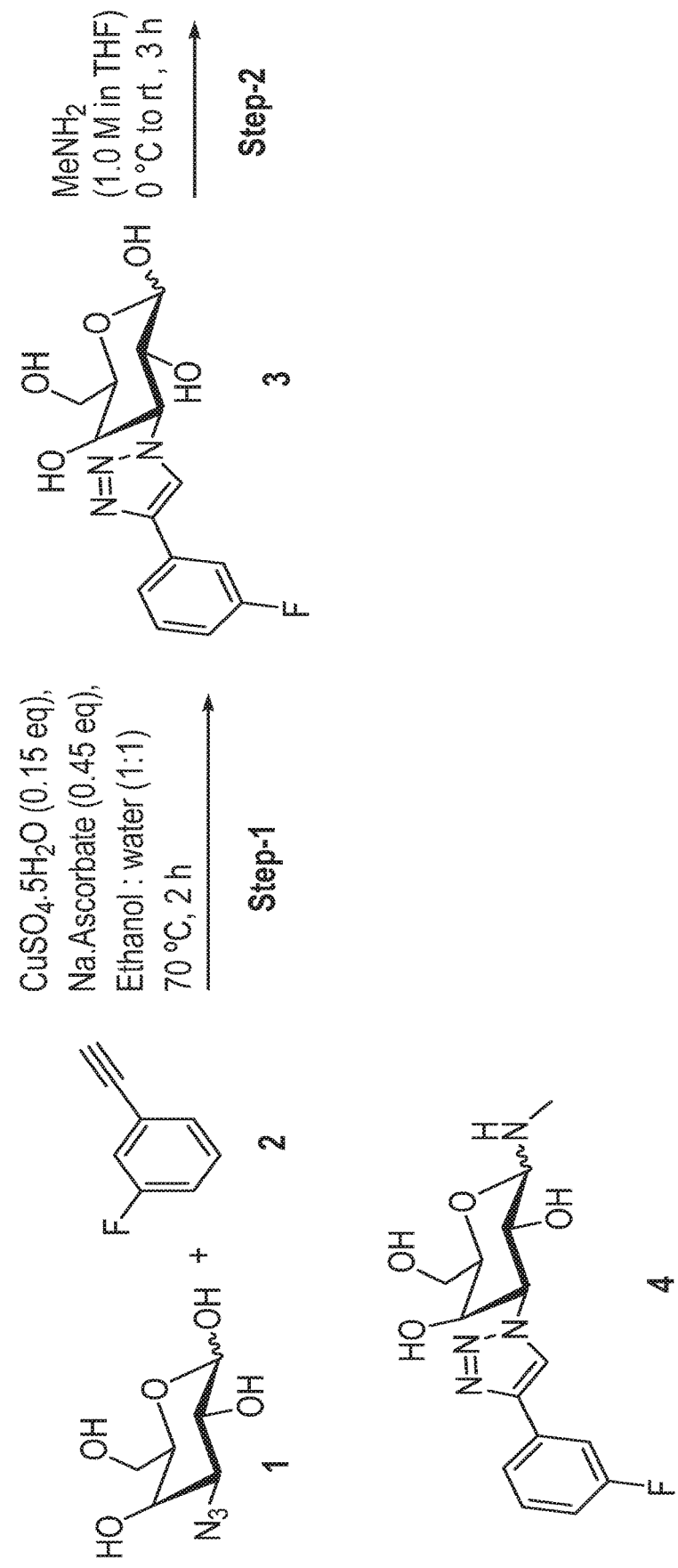

Scheme 1 - Synthesis of C$_3$-N$_3$-galactoside intermediate (Figure 4A)

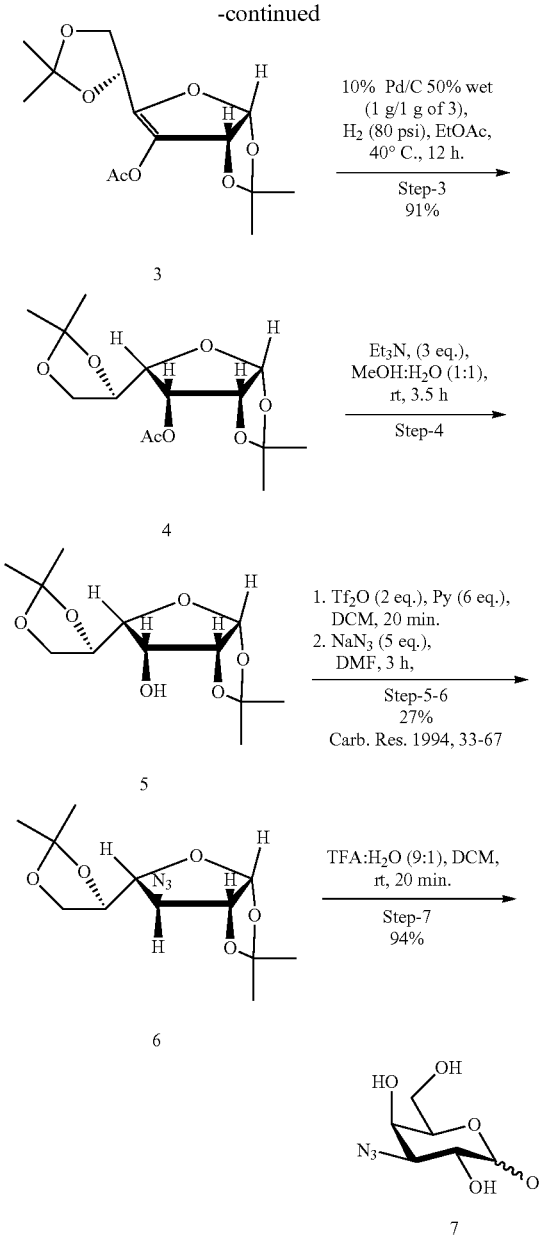

Step 1:

(3aR,5R,6aS)-5-((S)-2,2-dimethyl-1,3-dioxolan-4-yl)-2,2-dimethyldihydrofuro [2,3-d][1,3]dioxol-6(5H)-one:

To a stirred solution of (3aR,5S,6S,6aR)-5-((S)-2,2-dimethyl-1,3-dioxolan-4-yl)-2,2-dimethyltetrahydrofuro[2,3-d][1,3]dioxol-6-ol (1000 g, 3846 mmol) in DCM (8000 mL) was added Ac2O (3.9 eq) followed by PDC (1.5 eq) portion wise at room temperature over a period of 2 h. The reaction mixture was reflux for 3 h. After completion, the crude product was passed through a SiO2 column (60-120 mesh, 15 kg) and eluted with ethyl acetate (40 L). The solvent was evaporated to afford the title compound as a sticky yellow liquid (580 g, 58%). 1H NMR (400 MHz; CDCl3): ☐ 6.13 (d, J=4.4 Hz, 1H), 4.35-4.42 (m, 3H), 4.01-4.07 (m, 2H), 1.54 (s, 3H), 1.44 (s, 3H), 1.36 (s, 3H), 1.31 (S, 3H).

Step 2:

(3aR,6aR)-5-((S)-2,2-dimethyl-1,3-dioxolan-4-yl)-2,2-dimethyl-3a,6a-dihydro furo[2,3-d][1,3]dioxol-6-yl acetate: To a stirred solution of (3aR,5R,6aS)-5-((S)-2,2-dimethyl-1,3-dioxolan-4-yl)-2,2-dimethyldihydrofuro [2,3-d][1,3]dioxol-6(5H)-one (580 g, in ACN and pyridine was added Ac2O and the reaction mixture was heated to 80° C. for 16 h. After consumption of the starting material (monitored by TLC), the reaction mixture was concentrated in vacuum and codistilled with toluene (3×250 mL) to afford the title compound as a dark brown sticky liquid (595 g, crude, 88%).

1H-NMR (400 MHz; CDCl3): ☐ 6.03-6.02 d, 1H), 5.39-5.38 (d, J=5.4 Hz, 1H), 4.7 (t,1H), 4.0-4.10 (m, 2H), 2.23 (s, 3H), 1.54 (s, 3H), 1.46 (s, 3H), 1.44 (s, 3H), 1.37 (s, 3H).

Step 3:

(3aR,5S,6R,6aR)-5-((R)-2,2-dimethyl-1,3-dioxolan-4-yl)-2,2-dimethyl tetrahydrofuro [2,3-d][1,3]dioxol-6-yl acetate: To a stirred solution of (3aR,6aR)-5-((S)-2,2-dimethyl-1,3-dioxolan-4-yl)-2,2-dimethyl-3a,6a-dihydro furo [2,3-d][1,3]dioxol-6-yl acetate (595 g,) in EtOAc (8 volume) was added 10% Pd/C (200 g, 50% wet) and the reaction mixture was stirred at 40° C. for 12 h under H2 atm (80 psi). After completion, the reaction mixture was filtered through celite, washed with EtOAc (5×300 and concentrated in vacuum to afford the title compound as a sticky yellow liquid (544 g, 91%), 1H NMR (400 MHz; CDCl3): ☐ 5.80 (d, J=4.0 Hz, 1H), 5.04 (t, J=12.3 Hz, 1H), 4.78-4.81 (m, 1H), 4.58-4.64 (m, 1H), 4.01-4.13 (m, 2H), 3.5 (t, J=15.7 Hz, 1H), 2.16 (s, 3H), 1.57 (s, 3H), 1.43 (s, 3H), 1.37 (s, 3H), 1.34 (s, 3H).

Step 4:

(3aR,5R,6R,6aR)-5-((R)-2,2-dimethyl-1,3-dioxolan-4-yl)-2,2-dimethyltetra hydrofuro[2,3-d][1,3]dioxol-6-ol: To a stirred solution of (3aR,5S,6R,6aR)-5-((R)-2,2-dimethyl-1,3-dioxolan-4-yl)-2,2-dimethyl tetrahydrofuro [2,3-d][1,3] dioxol-6-yl acetate (544.0 g) in MeOH:H2O (1900 mL:1900 mL) was added Et3N (3.0 eq) and the reaction mixture was stirred at rt for 3.5 h. After completion, the reaction mixture was concentrated in vacuum and codistilled with toluene (3×500 mL) to afford the title compound as a black solid (510 g, crude). The crude was used for next step without purification. 1H NMR (400 MHz; CDCl3): ☐ 5.78 (d, J=4.0 Hz, 1H), 4.66 (t, J=10.2 Hz, 1H), 4.44-4.50 (m, 1H), 4.2 (m, 1H), 3.9 (m, 1H), 3.03-3.09 (m, 1H), 3.70 (t, J=4.5 Hz, 1 H), 1.44 (s, 3H), 1.42 (s, 3H), 1.37 (s, 3H).

Steps 5 and 6

(3aR,5R,6S,6aR)-6-azido-5-((R)-2,2-dimethyl-1,3-dioxolan-4-yl)-2,2-dimethyl tetrahydrofuro[2,3-d][1,3]dioxole:

To a stirred solution of (3aR,5R,6R,6aR)-5-((R)-2,2-dimethyl-1,3-dioxolan-4-yl)-2,2-dimethyltetra hydrofuro[2,3-d][1,3]dioxol-6-ol (510 g) in DCM:pyridine (3.0 eq) was slowly added triflic anhydride in DCM at −20° C. and the reaction mixture was stirred at same temperature for 30 min. after completion, the reaction mixture was quenched with ice cold 1N HCl (pH~6) and the aqueous layer was extracted with DCM (2×1000 mL), dried (Na2SO4) and concentrated. This crude residue was dissolved in DMF and NaN3 (5.0 eq) was added portionwise at 0° C. and stirred at the same temperature for 3 h. After completion, the reaction mixture was poured into ice water (500 mL) and extracted with ethyl acetate (2×1000 mL). The combined organic layer was again washed with ice cold water (3×500 mL), dried (Na2SO4) and concentrated. The residue was purified by flash column chromatography [normal phase, silica gel (100-200 mesh), gradient 0 to 5% EtOAc in hexane] to afford the title compound as pale yellow gum (150 g, 27%). 1H NMR (400 MHz, CDCl3): ☐ 5.80 (d, J=3.8 Hz, 1H), 4.60-4.63 (m,1H) 4.35-4.39 (m, 1H), 4.10 (t, J=3.6 Hz, 1H), 3.94 (d, J=2.8 Hz, 1H), 3.89-3.93 (m, 2H), 1.58 (s, 3H), 1.55 (s, 3H), 1.45 (s, 3H), 1.36 (s, 3H).

Step 7:

Synthesis of (3R,4S,5R,6R)-4-azido-6-(hydroxymethyl) tetrahydro-2H-pyran-2,3,5-triol: To a solution of (3aR,5R,6S,6aR)-6-azido-5-((R)-2,2-dimethyl-1,3-dioxolan-4-yl)-2,2-dimethyl tetrahydrofuro [2,3-d][1,3]dioxole (150 g) in DCM (500 mL) 90% TFA in water was slowly added at −20° C. and stirred at same temperature for 15 min. After completion the reaction mixture was concentrated in vacuum and codistilled with toluene (3×500 mL) to afford (3R,4S,5R,6R)-4-azido-6-(hydroxymethyl)tetrahydro-2H-pyran-2,3,5-triol (100 g, 94%) as a yellow solid.

1H-NMR (400 MHz; CDCl3): ☐ 5.23 (d, J=3.44 Hz, 1H), 4.59 (d, J=7.64 Hz, 1H), 4.64 (t, J=15.7 Hz, 2H), 3.87-3.93 (m, 1H), 3.58 (t, J=17.7 Hz, 1H), 3.48-3.56 (m, 1H).

Scheme 2 - Synthesis of an "galactoamide" intermediate (Figure 4A)

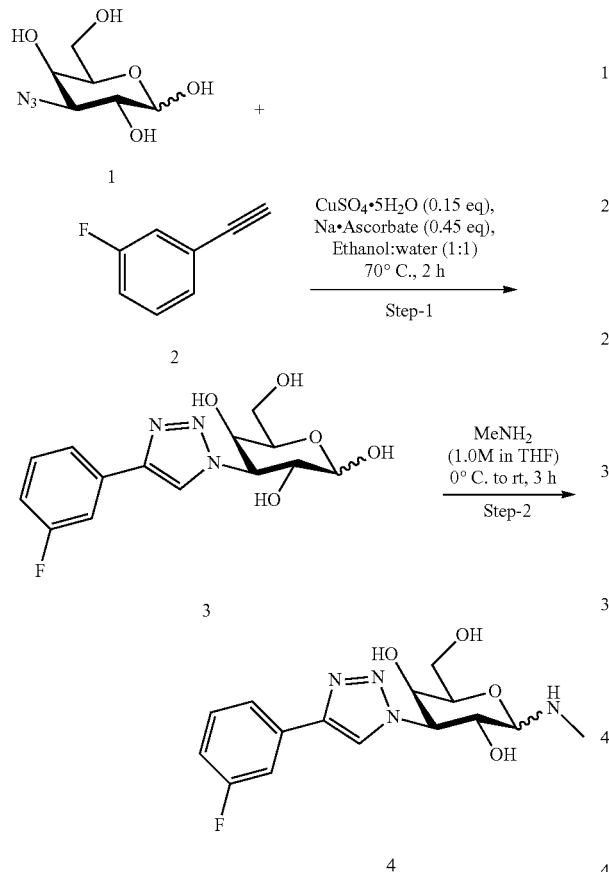

Step 1:

(3R,4S,5R,6R)-4-(4-(3-fluorophenyl)-1H-1,2,3-triazol-1-yl)-6-(hydroxymethyl) tetrahydro-2H-pyran-2,3,5-triol (3)

CuSO4.5H2O (638 mg, 1.64 mmol) and sodium ascorbate (870 mg, 4.39 mmol) were added to a solution of (3R,4S,5R,6R)-4-azido-6-(hydroxymethyl)tetrahydro-2H-pyran-2,3,5-triol (2.0 g, 9.75 mmol) and 1-ethynyl-3-fluorobenzene (2.46 g, 19.51 mmol) in EtOH—H2O (1:1, 20 mL) at room temperature and the reaction mixture was heated to 70° C. for 5 h. After completion, the reaction mixture was cooled to room temperature. The volatiles were evaporated and the aqueous part was extracted with EtOAc (3×30 mL). The organic layer was dried (Na2SO4) and concentrated and the residue was triturated with Et2O to afford the title compound as a yellow solid (2.8 g, 90%). ESIMS m/z 326 [M+H]+: 1H NMR (400 MHz, DMSO-d6, anomeric mixture, α:β=1:1): d 3.37-3.46 (m, 3H), 3.49-3.57 (m, 3H), 3.66 (t, J=6.1 Hz, 1H), 3.86-3.89 (m, 1H), 3.92-3.96 (m, 2H), 4.03 (t, J=6.2 Hz, 1H), 4.25-4.32 (m, 1H), 4.53-4.61 (m, 2H), 4.66 (t, J=5.5 Hz, 1H), 4.71 (dd, J=11.0 & 3.1 Hz, 1H), 4.84-4.89 (m, 2H), 5.11-5.17 (m, 3H), 5.23 (d, J=5.7 Hz, 1H),6.71 (d, J=4.5 Hz, 1H), 6.93 (d, J=6.1 Hz, 1H), 7.14 (t, J=8.5 Hz, 2H), 7.46-7.51 (m, 2H), 7.69 (d, J=10.2 Hz, 2H), 7.73 (d, J=7.8 Hz, 2H), 8.57 (s, 1H), 8.61 (s, 1H).

Step 2:

(2R,3R,4S,5R)-4-(4-(3-fluorophenyl)-1H-1,2,3-triazol-1-yl)-2-(hydroxymethyl)-6-(methylamino)tetrahydro-2H-pyran-3,5-diol (4)

Methyl amine (1.0 M in THF, 10.0 mL) was added a solution of (3R,4S,5R,6R)-4-(4-(3-fluorophenyl)-1H-1,2,3-triazol-1-yl)-6-(hydroxymethyl)tetrahydro-2H-pyran-2,3,5-triol (950 mg, 2.91 mmol) in THF (4 mL), at 0° C. The resulting reaction mixture was stirred at rt for 3 h. After completion the volatiles were evaporate under reduced pressure to the title compound as a greenish solid (900 mg, crude). ESIMS m/z 347.12 [M+H]+; 1H NMR (400 MHz, CDCl3): ☐ 2.04 (S, 3H), 2.06 (s, 3H), 2.18 (s, 3H), 2.45 (s, 3H), 2.76-2.80 (m, 1H), 4.03-4.17 (m, 3H), 5.44-5.53 (m, 3H), 7.27 (d, J=8.1 Hz, 2H), 7.75 (d, J=8.1 Hz, 2H).

Figure 4B:
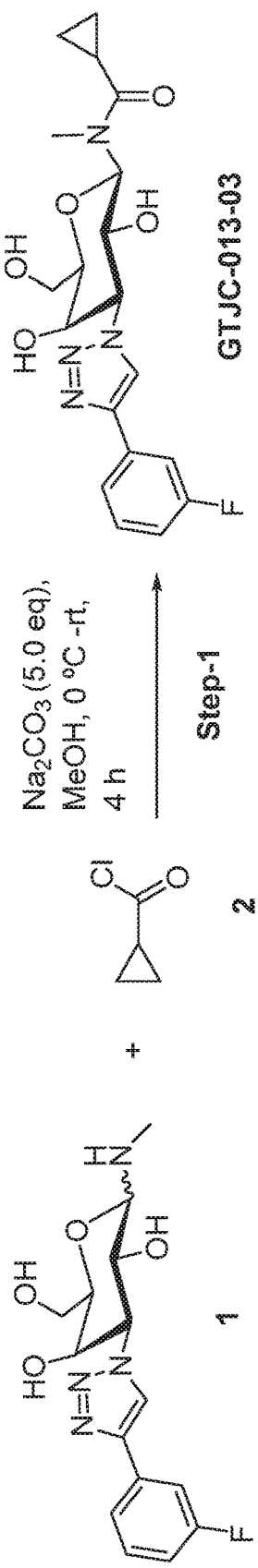
Figure 4B:
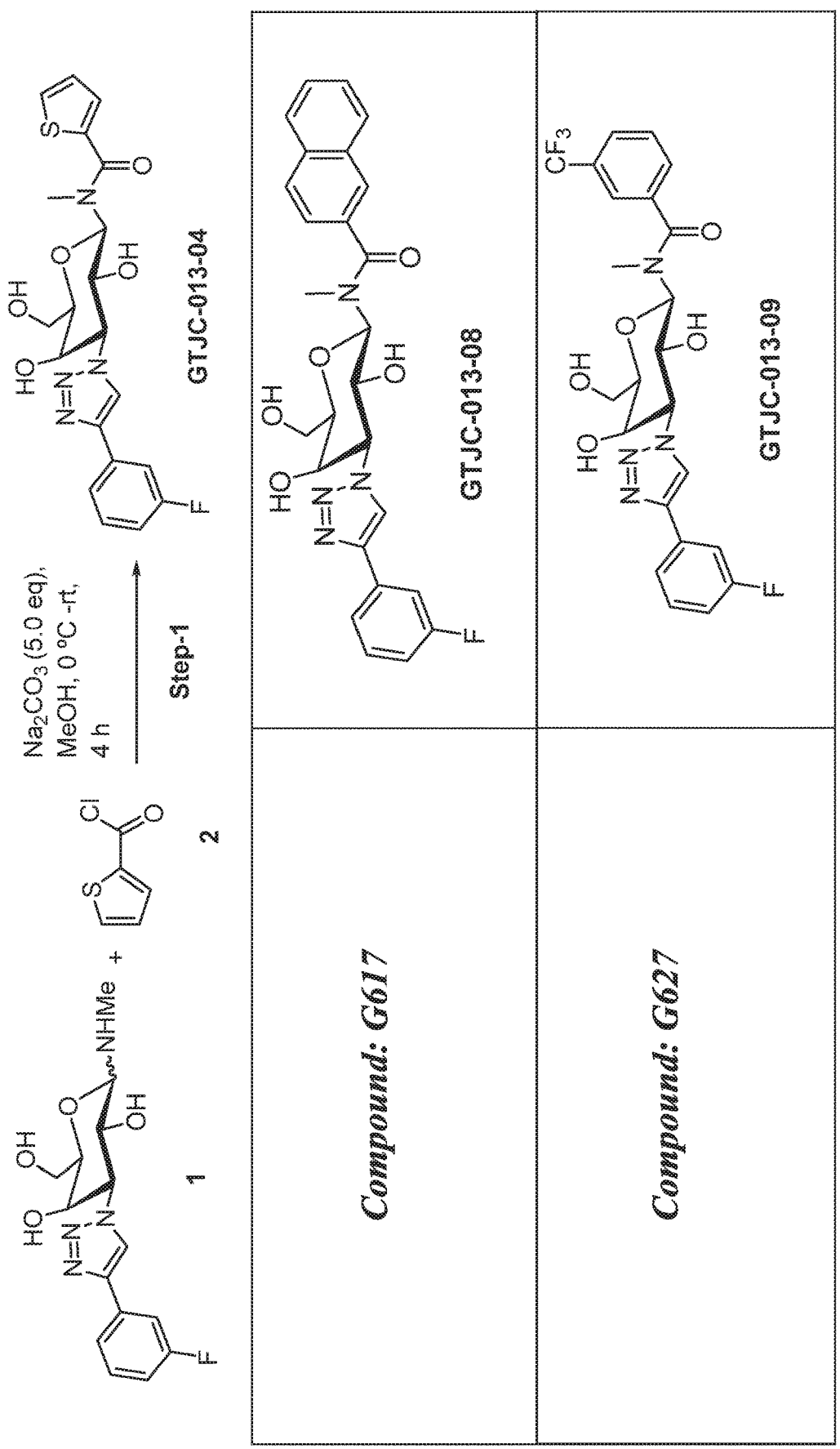
Figure 4B:
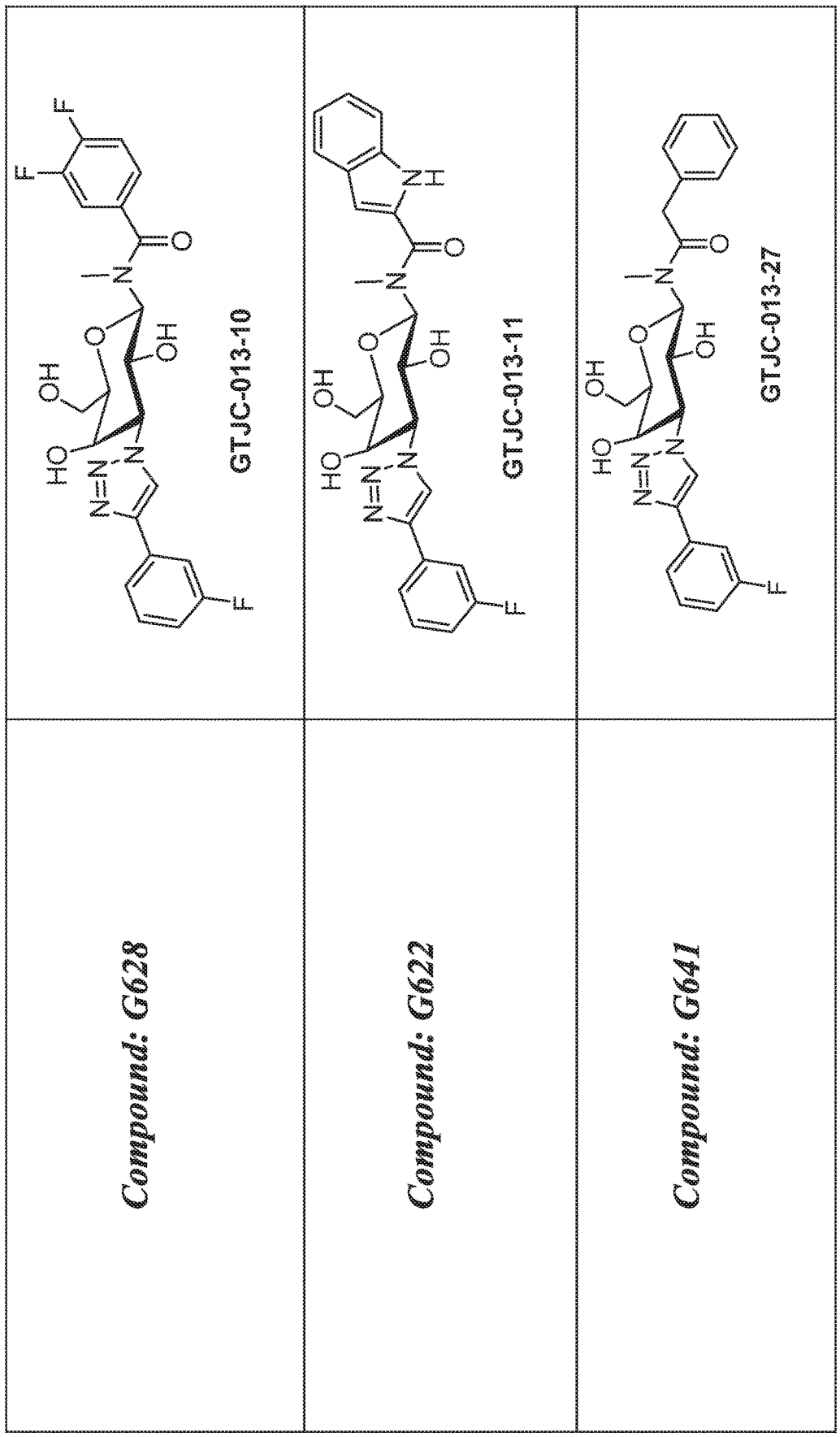

Scheme 3 - synthesis of G623 (Figure 4B)

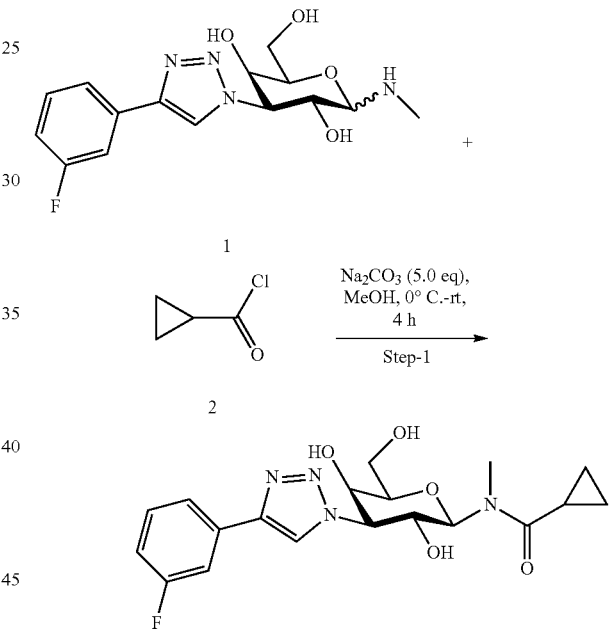

GTJC-013-03

Step 1:

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylcyclopropanecarboxamide (GTJC-013-03)

Na2CO3 (235 mg, 2.212 mmol) and cyclopropanecarbonyl chloride 2 (94 mg, 0.885 mmol) were added to a solution of (2R,3R,4S,5R)-4-(4-(3-fluorophenyl)-1H-1,2,3-triazol-1-yl)-2-(hydroxymethyl)-6-(methylamino)tetrahydro-2H-pyran-3,5-diol 1 (150 mg, 0.442 mmol) in methanol (3 mL) at 0° C. The reaction mixture was stirred at room temperature. After completion the reaction mixture was quenched with water (5 mL) and extracted with EtOAc (3×25 mL). The combined organic layers were washed with brine, dried (Na2SO4), filtered and concentrated under reduced pressure at 45° C. The residue was purified by flash column chromatography eluting with 4% Methanol in DCM to afford the title compound as a white solid (35 mg, 19%), HRMS: (ESI) [M+H]+ calc. for C19H23FN4O5 406.17, found: 407.36 [M+H]+; LCMS: m/z 407 [M+H]+ (ES+) at 89.73% at 3.92 min and 7.08% at 4.14 min.

1H NMR (400 MHz, DMSO-d6, anomeric mixture, α:β=1:9): ☐ 8.72 (s, 1H), 7.69-7.76 (m, 2H), 7.43-7.52 (m, 1H), 7.13-7.17 (m, 1H), 5.54-5.57 (m, 1H), 5.34 (d, 0.9 H, J1-2=6.4 Hz, α-H-1), 5.33 (d, 0.1 H, J1-2=2.7 Hz, β-H-1), 4.96-5.00 (m, 1H), 4.48-4.82 (m, 2H), 3.74-3.92 (m, 2H), 3.48-3.53 (m, 2H), 3.13 (s, 3H), 2.08 (m, 1H) 0.75-0.85 (m, 4H),

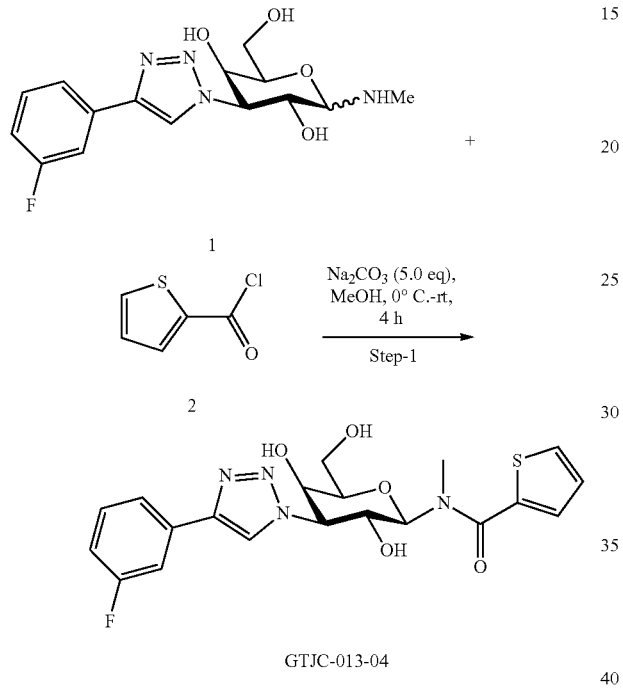

Scheme 4 - Synthesis of G620 (Figure 4B)

Step 1:

N-((2R,3R,4S,5R,6R)-4-(4-(3-fluorophenyl)-1H-1,2, 3-triazol-1-yl)-3,5-dihydroxy-6-(hydroxymethyl) tetrahydro-2H-pyran-2-yl)-N-methylthiophene-2-carboxamide (GTJC-013-04)

Na2CO3 (47.04 mg, 0.4437 mmol) and thiophene-2-carbonyl chloride 2 (43.19 mg, 0.2958 mmol) were added to a solution of (2R,3R,4S,5R)-4-(4-(3-fluorophenyl)-1H-1,2, 3-triazol-1-yl)-2-(hydroxymethyl)-6-(methylamino)tetrahydro-2H-pyran-3,5-diol 1 (50 mg, 0.1479 mmol) in methanol (3 mL) at 0° C. The reaction mixture was stirred at room temperature. After completion the reaction mixture was quenched with water (5 mL) and extracted with EtOAc (3×25 mL). The combined organic layers were washed with brine, dried (Na2SO4), filtered and concentrated under reduced pressure at 45° C. The residue was purified by flash column chromatography by using 2% Methanol in DCM to afford the title compound as a white solid (15 mg, 23%). HRMS (ESI) [M+H]+ calc. for C20H21FN4O5S: 448.12, found: 449.35 [M+H]+; LCMS: m/z 449 [M+H]+;

1H NMR (400 MHz, DMSO-d6, single β isomer): ☐ 8.66 (s, 1 H), 7.83 (d, 1H), 7.75-7.82 (m, 2H), 7.63 (d, 1H), 7.47-7.52 (m, 1H), 7.13-7.17 (m, 2H), 5.60 (s, 1H), 5.35 (d, J1-2=6.5 Hz, α-H-1), 5.19 (s, 1H), 4.91-4.94 (m, 1H), 4.86 (m, 1H), 4.52-4.54 (m, 1 H), 3.90 (m, 1 H), 3.79 (m, 1H), 3.52-3.56 (m, 2H), 3.06 (s, 3H).

Synthesis of G617 (FIG. 4B)

N-((2R,3R,4S,5R,6R)-4-(4-(3-fluorophenyl)-1H-1,2, 3-triazol-1-yl)-3,5-dihydroxy-6-(hydroxymethyl) tetrahydro-2H-pyran-2-yl)-N-methyl-2-naphthamide (GTJC-013-08)

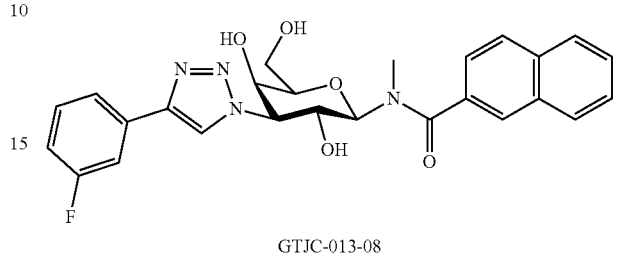

GTJC-013-08

Synthesized following the standard procedure used for GTJC-013-03 or GTJC-013-04

Appearance: white solid; synthesized: 85 mg; yield 23%

LCMS: m/z 493 [M+H]+; 1H NMR (400 MHz, DMSO-d6): ☐ 3.13 (s, 3H), 3.52-3.60 (m, 2H), 3.66-3.72 (m, 1H), 3.79-3.83 (m, 1H), 4.50-4.56 (m, 1H), 4.72-4.77 (m, 1H), 4.85 (d, J=8.8 Hz, 1H), 5.01 (t, J=5.3 Hz, 1H), 5.33 (d, J=6.8 Hz, 1H), 5.55 (d, J=6.4 Hz, 1H), 7.13-7.18 (m, 1H), 7.46-7.52 (m, 1H), 7.58-7.74 (m, 5H), 7.99 (d, J=8.0 Hz, 2H), 8.05 (d, J=7.6 Hz, 1H), 8.25 (s, 1H), 8.71 (s, 1H).

Synthesis of G627 (FIG. 4B)

N-((2R,3R,4S,5R,6R)-4-(4-(3-fluorophenyl)-1H-1,2, 3-triazol-1-yl)-3,5-dihydroxy-6-(hydroxymethyl) tetrahydro-2H-pyran-2-yl)-N-methyl-3-(trifluoromethyl)benzamide (GTJC-013-09)

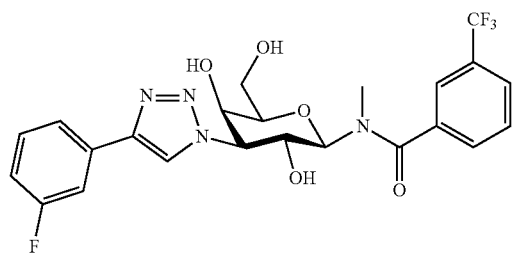

GTJC-013-09

Synthesized following the standard procedure used for GTJC-013-03 or GTJC-013-04

Appearance: white solid; synthesized: 40 mg; yield 13%

HRMS (ESI) [M+H]+ calc. for C23H22F4N4O5 510.15, found: 511.37 [M+H]+

1H NMR (400 MHz, DMSO-d6) (anomeric mixture α:β=1:8): ☐ 8.73 (s, 1H), 7.87-7.93 (m, 3H), 7.67-7.74 (m, 3H), 7.47-7.52 (m, 1H), 7.13-7.18 (m, 1H), 5.60 (d, J1-2=6.68 Hz, α-H-1), 5.34 (d, 1H,), 5.01 (d, J1-2=4.7 Hz, β-H-1), 4.43-4.83 (m, 4H), 3.53-3.58 (m, 4H), 3.08 (s, 3H).

Synthesis of G628 (FIG. 4B)

3,4-difluoro-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylbenzamide (GTJC-013-10)

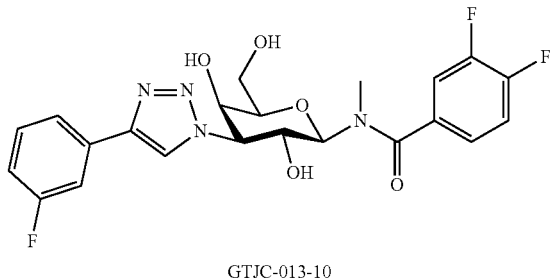

GTJC-013-10

Synthesized following the standard procedure used for GTJC-013-03 or GTJC-013-04

Appearance: white solid; synthesized: 25 mg; yield 9%
α,β isomers are separated by Prep HPLC.
LCMS (β isomer): m/z 479 [M+H]+ (ES+), at 4.65 min (98.44%)
LCMS (α isomer): m/z 479 [M+H]+ (ES+), at 4.79 min (97.98%)
1H-NMR (400 MHz, DMSO-d6, single β isomer) □ 8.73 (s, 1H), 7.72-7.74 (m, 1H), 7.62-7.67 (m, 1H), 7.57-7.60 (m, 1H), 7.50-7.54 (m, 2H), 7.42-7.47 (m,1H), 7.12-7.17 (m,1H), 5.58-5.62 (m, 1H), 5.34 (d, 1H, J=6.68 Hz), 4.82-4.99 (m, 2H), 4.78 (d, 1H, J1-2=11.9 Hz, α-H-1), 4.45-4.52 (m, 1 H), 3.82-3.96 (m, 1H), 3.49-3.60 (m, 3H), 3.05 (s, 3H).
1H-NMR (400 MHz; DMSO-d6, single α isomer) □ 9.00 (s, 1H), 7.72-7.74 (m, 1H), 7.66-7.68 (m, 1H), 7.49-7.62 (m, 3H), 7.42 (m, 1H), 7.16-7.21 (m, 1H), 6.21 (bs, 1H), 5.17-5.29 (m, 3H), 4.78-4.83 (m, 1H), 4.62-4.64 (m, 1H), 4.45 (d, 1H, J1-2=8.12 Hz, β-H-1), 3.38-3.41 (m, 2H), 3.28-3.33 (m, 2H), 3.05 (s, 3H).

Synthesis of G622 (FIG. 4B)

N-((2R,3R,4S,5R6R)-4-(4-(3-fluorophenyl)-1H-1,2,3-triazol-1-yl)-3,5-dihydroxy-6-(hydroxymethyl)tetrahydro-2H-pyran-2-yl)-N-methyl-1H-indole-2-carboxamide (GTJC-013-11)

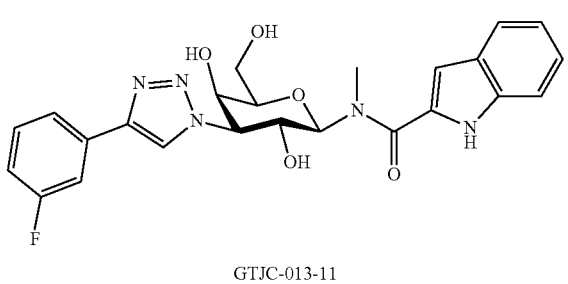

GTJC-013-11

Synthesized following the standard procedure used for GTJC-013-03 or GTJC-013-04

Appearance: white solid; synthesized: 12 mg; yield 8%
HRMS (ESI) [M+H]+ calc. for C24H24FN5O5 481.18, found: 482.38 [M+H]+; LCMS: m/z 482 (M+H)+ (ES+) 93.64% at 4.78 min; 1H NMR (400 MHz, DMSO-d6, single β isomer): □ 11.58 (s, 1H), 8.77 (s, 1H), 7.71-7.73 (m, 1H), 7.62-7.68 (m, 2H), 7.49-7.52 (m, 1H), 7.44-7.47 (m,1 H), 7.19-7.22 (m, 1H), 7.13-7.17 (m, 1H), 7.06-7.08 (m, 1H), 7.03 (s, 1H), 5.60 (s, 2H), 5.36 (d, 1H, J1-2=6.52 Hz, α-H-1), 4.94 (m, 2H), 4.55 (m, 1H), 3.84-3.91 (m, 2H), 3.55-3.64 (m, 2H), 3.10 (s, 3H).

Synthesis of G641 (FIG. 4B)

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methyl-2-phenylacetamide (GTJC-013-27)

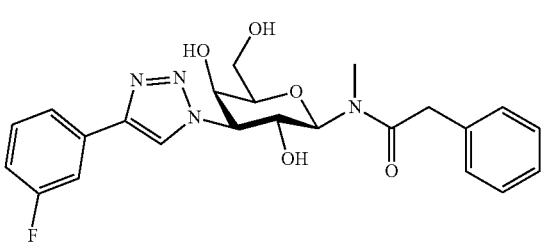

GTJC-013-27

Synthesized following the standard procedure used for GTJC-013-03 or GTJC-013-04

Appearance: white solid; synthesized: 30 mg; yield 23%
ESIMS: m/z 347.12 [M+1]+; 1H NMR (400 MHz, DMSO-d6): □ 3.49-3:61 (m, 4H), 3.72 (t, J=6.2 Hz, 2H), 3.99 (dd, 6.6 & 2.9 Hz, 2H), 4.36-4.43 (m, 2H), 4.70 (t, J=5.5 Hz, 1H), 4.82 (dd, 10.5 & 2.8 Hz, 2H), 5.19 (d, J=9.7 Hz, 2H), 5.31 (d, J=7.2 Hz, 2H), 5.40 (d, J=6.6 Hz, 2H), 7.12-7.17 (m, 2H), 7.46-7.51 (m, 2H), 7:66 (dd, J=10.2 & 2.3 Hz, 2H), 7.72 (d, J=7.8 Hz, 2H), 8.67 (s, 2H).

Synthesis of G649 (FIG. 4B)

2-(3,4-difluorophenyl)-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylacetamide (GTJC-013-37)

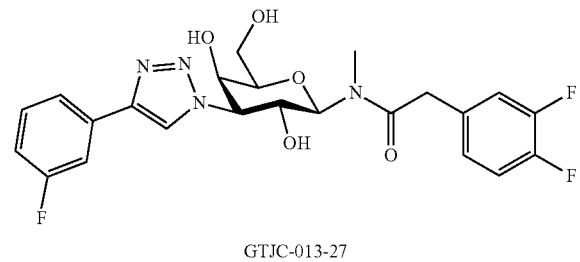

GTJC-013-27

Synthesized following the standard procedure used for GTJC-013-03 or GTJC-013-04

Appearance: white solid; synthesized: 25 mg; yield 17%
HRMS (ESI) [M+H]+ calc. for C23H23F3N4O5 492.16, found: 493.5 [M+H]+
LCMS: m/z 493.5 [M+H]+ (ES+) 88.40% at 4.75 min and 9.81% at 4.88 min,
1H NMR (400 MHz; DMSO-d6, anomeric mixture, α:β=1:9): □ 8.74 (s, 1H), 7.69-7.76 (m, 2H), 7.49-7.53 (m, 1H), 7.31-7.39 (m, 2H), 7.28-7.29 (m, 2H), 5.59 (d, 1H, J1-2=9.48 Hz, α-H-1), 4.70-5.36 (m, 5H), 3.76-3.94 (m, 4H), 3.45-3.51 (m, 2H), 3.03 (s, 3H).

Synthesis of G651 (FIG. 4B)

2-(3,4-difluorophenoxy)-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylacetamide (GTJC-013-38)

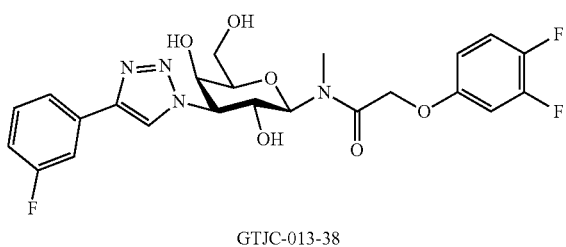

GTJC-013-38

Synthesized following the standard procedure used for GTJC-013-03 or GTJC-013-04

Appearance: white solid; synthesized: 15 mg; yield 11%
HRMS (ESI) [M+H]+ calc. for C23H23F3N4O6 508.16, found: 509.52 [M+H]+
LCMS: m/z 509.5 [M+H]+ (ES+) 91.95% at 4.86 min & 6.98% at 4.96 min,
1H NMR (400 MHz; DMSO-d6, anomeric mixture α:β=1:13): □ 8.77 (s, 2H), 7.74-7.76 (m, 2H), 7.69-7.72 (m, 2H), 7.47-7.53 (m, 2H), 7.30-7.37 (m, 2H), 7.13-7.18 (m, 2H), 7.02-7.08 (m, 2H), 6.76-6.80 (m, 2H), 5.73 (d, 1H, J1-2=6.8 Hz, α-H-1), 5.37-5.41 (m, 2H), 5.29-5.31 (m, 1H), 5.02-5.04 (m, 1H), 4.91-4.98 (m, 5H), 4.76-4.79 (m, 2H), 4.70-4.72 (m, 1H), 4.37-4.44 (m, 2H), 3.91-3.96 (m, 3H), 3.79-3.82 (m, 1H), 3.50-3.56 (m, 2H), 3.00 (s, 2H), 2.88 (s, 3H).

Synthesis of G652 (FIG. 4B)

3-(3,4-difluorophenyl)-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylpropanamide (GTJC-013-41)

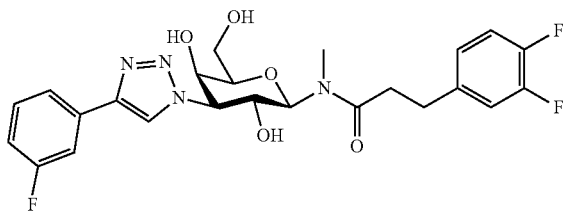

GTJC-013-41

Synthesized following the standard procedure used for GTJC-013-03 or GTJC-013-04

Appearance: white solid; synthesized: 11 mg; yield 9%
HRMS (ESI) [M+H]+ calc. for C24H25F3N4O5 506.18, found: 507.52 [M+H]+; LCMS: m/z 507.5 [M+H]+ (ES+) 75.38% at 5.04 min, 7.07% at 5.15 min, 7.07%, 15.93% at 5.28 min.
1H NMR (400 MHz; DMSO-d6, mixture of 3 isomers): □ 8.71 (s, 1H), 7.51-7.77 (m, 2H), 7.37-7.49 (m, 1H), 7.29-7.35 (m, 2H), 7.14-7.26 (m, 2H), 5.48 (d, 1H, J1-2=6.92 Hz, α-H-1), 4.68-5.32 (m, 4H), 4.40-4.50 (m, 1H), 3.51-3.99 (m, 4H), 2.54-2.89 (m, 7H).

Synthesis of G658 (FIG. 4B)

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-3,4-dimethoxy-N-methylbenzamide (GTJC-013-46-1)

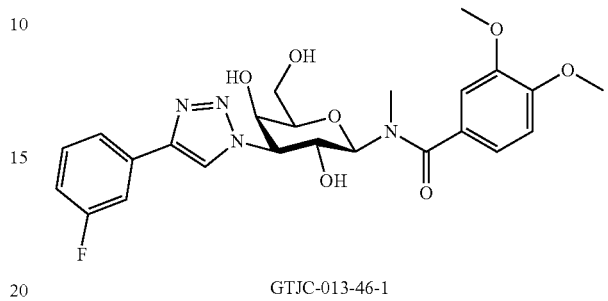

GTJC-013-46-1

Synthesized following the standard procedure used for GTJC-013-03 or GTJC-013-04

Appearance: white solid; synthesized: 110 mg; yield 37%
HRMS (ESI) [M+H]+ calc. for C24H27FN4O7 502.19, found: 503.52 [M+H]+;
LCMS: m/z 503.5 (M+H)+ (ES+) 95.21% at 4.25 min; 1H NMR (400 MHz; DMSO-d6, single β isomer): 8.71 (s, 1H), 7.68-7.75 (m, 2H), 7.46-7.52 (m, 1H), 7.12-7.18 (m, 3H), 7.01 (d, J=8.28 Hz, 1H), 5.55 (d, 1H, J1-2=6.36 Hz, α-H-1), 5.32 (d, J=6.64 Hz, 1 H), 4.90-4.92 (m, 1H), 4.83 (m, 2H), 4.45-4.52 (m, 1H), 3.79-3.85 (m, 7H), 3.61-3.67 (m, 1H), 3.32-3.59 (m, 2H), 3.02 (s, 3H).

Synthesis of G655 (FIG. 4B)

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-3,4-dihydroxy-N-methylbenzamide (GTJC-013-46)

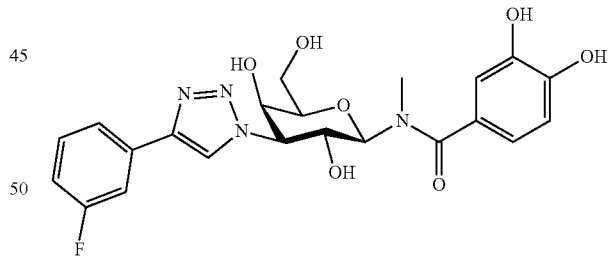

GTJC-013-46

Synthesized following the standard procedure used for GTJC-013-23

Appearance: white solid; synthesized: 18 mg; yield 24%
HRMS (ESI) [M+H]+ calc. for C22H23FN4O7 474.16, found: 475.50 [M+H]+
LCMS: m/z 475.5 [M+H]+ (ES+) 98.93% at 3.86 min.
1H NMR (400 MHz; DMSO-d6, single β isomer): □ 9.11 (bs, 2H), 8.71 (s, 1H), 7.74 (d, 1H, J=7.68 Hz,), 7.69 (d, J=10.32 Hz, 1H), 7.46-7.52 (m, 1H), 7.12-7.17 (m, 1H), 6.94 (s, 2H), 6.73-6.75 (m, 1H), 5.51 (d, 1H, J1-2=6.01 Hz, α-H-1), 5.29 (bs, 1H), 4.45-4.85 (m, 4H), 3.86 (bs,1H), 3.57 (m, 3H), 2.98 (s, 3H).

Synthesis of G642 (FIG. 4B)

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methyl-3-(trifluoromethoxy)benzamide (GTJC-013-45)

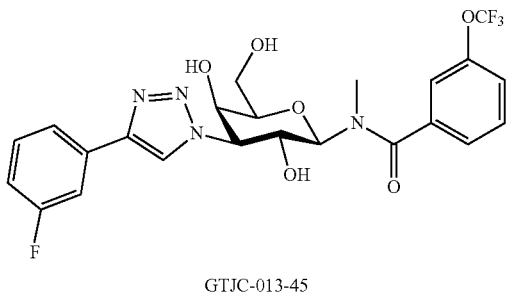

GTJC-013-45

Synthesized following the standard procedure used for GTJC-013-03 or GTJC-013-04

Appearance: white solid; synthesized: 50 mg; yield 33%
HRMS (ESI) [M+H]+ calc. for C23H22F4N4O6 526.15, found: 527.47 [M+H]+
1H NMR (400 MHz, DMSO-d6, anoretic mixture): d 8.82 (s, 1H), 7.83-7.93 (m, 3H), 7.69-7.77 (m, 3H), 7.49-7.52 (m, 1H), 7.13-7.18 (m, 1H), 5.60 (d, 1H, J1-2=6.68 Hz, α-H-1), 5.34 (d, J=6.6 Hz, 1H), 5.14 (d, 1H, J1-2=4.0 Hz, β-H-1), 4.47-4.61 (m, 4H), 3.39-3.60 (m, 4H), 3.08 (s, 3H).

Synthesis of G650 (FIG. 4B)

Synthesis of 2,3,4,5,6-pentafluoro-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylbenzamide (GTJC-013-47)

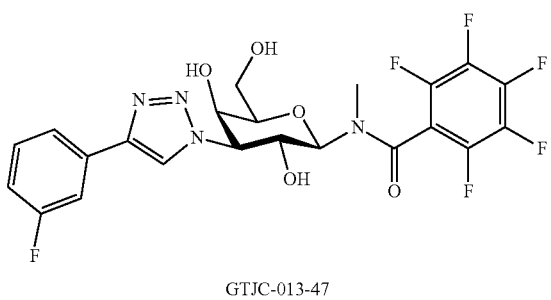

GTJC-013-47

Synthesized following the standard procedure used for GTJC-013-03 or GTJC-013-04

Appearance: white solid; synthesized: 30 mg; yield 19%
HRMS (ESI) [M+H]+ calc. for: C22H18F6N4O5 532.12, found: 533.48 [M+H]+;
LCMS: m/z 533.4 [M+H]+ (ES+) 82.08% at 5.04 min & 14.98% at 5.15 min.
1H NMR (400 MHz, DMSO-d6, anomeric mixture, α:β=1:6): ☐ 8.71 (s, 1H), 7.55-7.74 (m, 2H), 7.47-7.52 (m, 1H), 7.13-7.21 (m, 1H), 5.37 (d, 1H, J1-2=6.6 Hz, α-H-1), 4.37-5.62 (m, 5H), 3.32-3.69 (m, 4H), 3.07 (s, 3H).

Synthesis of G629 (FIG. 4B)

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-1-methoxy-N-methyl-2-naphthamide (GTJC-013-22)

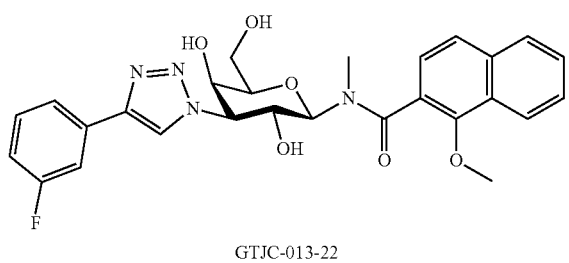

GTJC-013-22

Synthesized following the standard procedure used for GTJC-013-03 or GTJC-013-04

Appearance: white solid; synthesized: 110 mg; yield 35%
ESIMS: m/z 347.12 [M+H]+; 1H NMR (400 MHz, DMSO-d6): 3.49-3.61 (m, 4H), 3.72 (t, J=6.2 Hz, 2H), 3.99 (dd, 6.6 & 2.9 Hz, 2H), 4.36-4.43 (m, 2H), 4.70 (t, J=5.5 Hz, 1H), 4.82 (dd, 10.5, 2.8 Hz, 2H), 5.19 (d, J=9.7 Hz, 2H), 5.31 (d, J=7.2 Hz, 2H), 5.40 (d, J=6.6 Hz, 2H), 7.12-7.17 (m, 2H), 7.46-7.51 (m, 2H), 7.66 (dd, J=10.2 & 2.3 Hz, 2H), 7.72 (d, J=7.8 Hz, 2H), 8.67 (s, 2H).

Scheme 5 (FIG. 4C)

Synthesis of G635

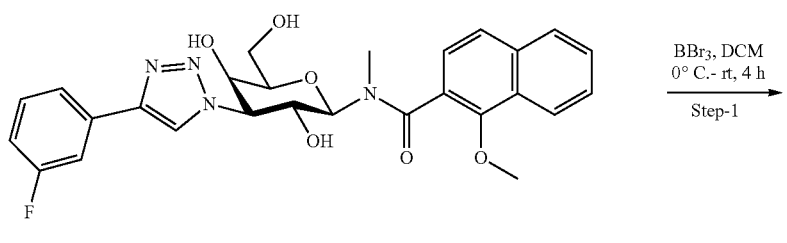

GTJC-013-22

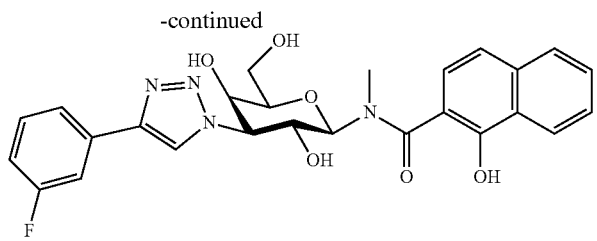

GTJC-013-23

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-1-hydroxy-N-methyl-2-naphthamide (GTJC-013-23)

To a solution of N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-1-methoxy-N-methyl-2-naphthamide (80 mg, 0.1532 mmol) in DCM (4 mL) added BBr3 (115.4 mg, 0.4597 mmol) at 0° C. The resulting mixture was stirred at room temperature for 3 h. After completion, the reaction mixture was quenched with saturated NaHCO3 solution (6 mL) to adjust pH~8 and the aqueous layer was extracted with DCM (3×10 mL). The combined organic layer was dried (Na2SO4) and concentrated in vacuo. The residue was purified by Flash chromatography eluting with 3% Methanol in DCM to afford the title compound as white solid (13 mg, 17%). ESIMS: m/z 347.12 [M+1]+, 1H NMR (400 MHz, DMSO-d6): □ 3.49-3.61 (m, 4H), 3.72 (t, J=6.2 Hz, 2H), 3.99 (dd, 6.6, 2.9 Hz, 2H), 4.36-4.43 (m, 2H), 4.70 (t, J=5.5 Hz, 1H), 4.82 (dd, 10.5 & 2.8 Hz, 2H), 5.19 (d, J=9.7 Hz, 2H), 5.31 (d, J=7.2 Hz, 2H), 5.40 (d, J=6.6 Hz, 2H), 7.12-7.17 (m, 2H), 7.46-7.51 (m, 2H), 7.66 (dd, J=10.2 & 2.3 Hz, 2H), 7.72 (d, J=7.8 Hz, 2H), 8.67 (s, 2H).

Figure 4D:
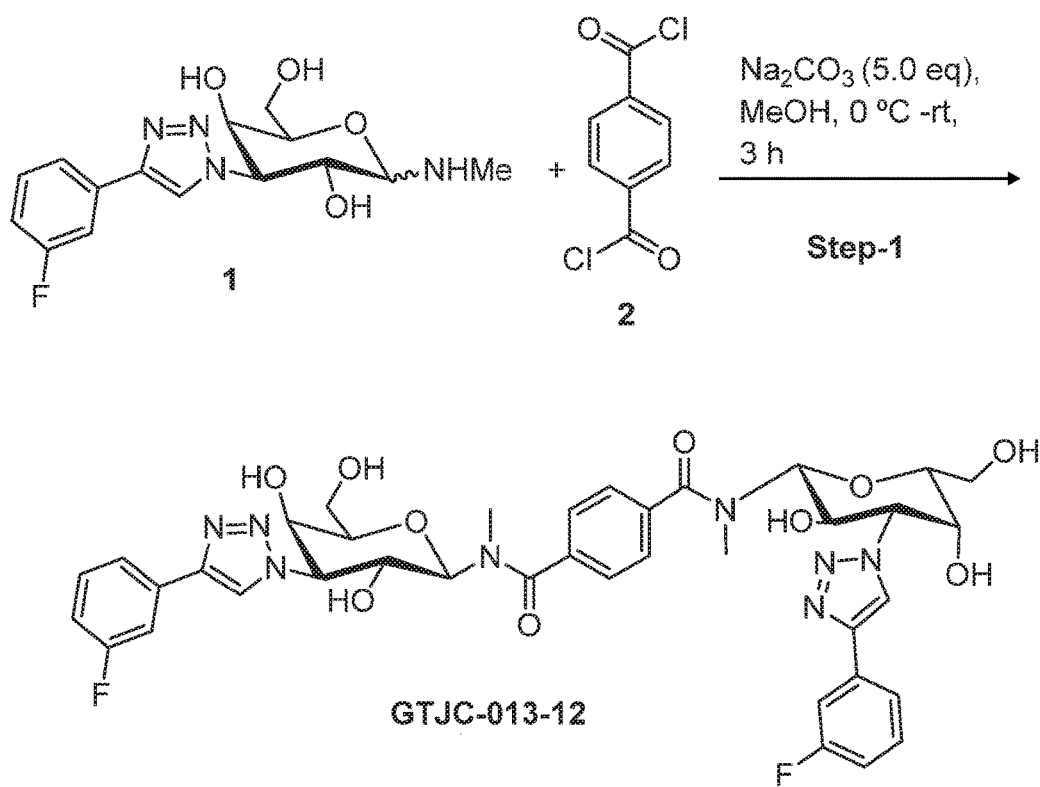

Scheme 6 (FIG. 4D)

Synthesis of G637

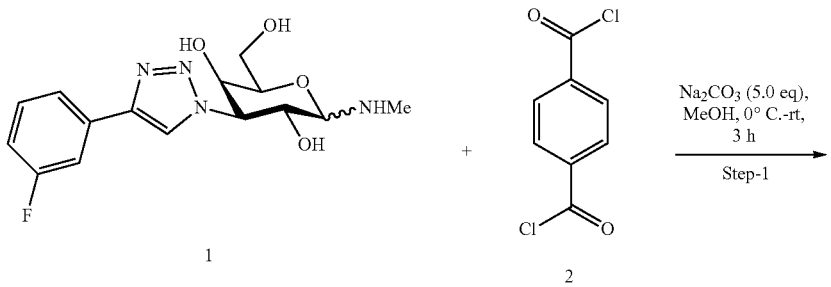

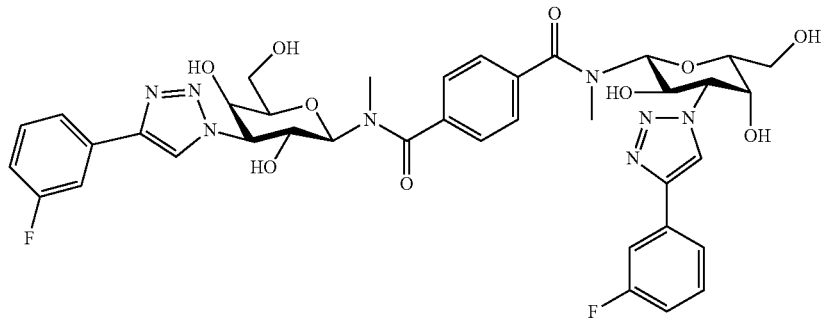

GTJC-013-12

Figure 4E:
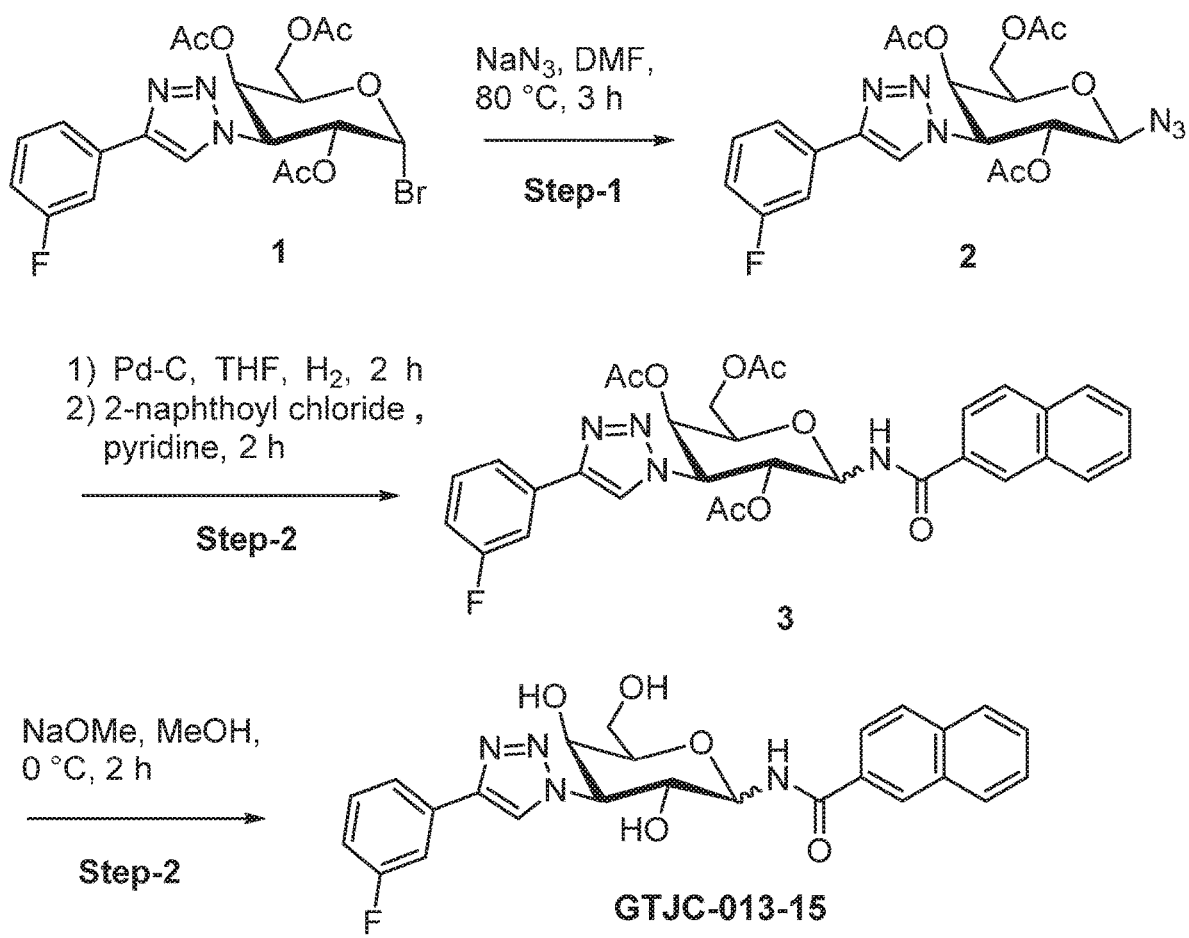

N1,N4-bis((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N1,N4-dimethylterephthalamide (GTJC-013-12): To a solution of (2R,3R,4S,5R)-4-(4-(3-fluorophenyl)-1H-1,2,3-triazol-1-yl)-2-(hydroxymethyl)-6-(methylamino)tetrahydro-2H-pyran-3,5-diol (140 mg, 0.4142 mmol) in methanol (3 mL) was added Na2CO3 (220 mg, 2.0710 mmol) and terephthaloyl dichloride (172 mg, 0.8284 mmol) at 0° C. The reaction mixture was stirred at room temperature. After completion the reaction mixture was quenched with water (5 mL) and extracted with EtOAc (3×25 mL). The combined organic layers were washed with brine and dried (Na2SO4), filtered and concentrated under reduced pressure at 45° C. The residue was purified by Prep HPLC to afford the title compound (3 mg) as white solid. HRMS (ESI) [M+H]+ calc. for C38H40F2N8O10 806.28, found: 807.71 [M+H]+; LCMS: m/z 807.7 (M+H)+ (ES+) 98.10% at 4.49 min. 1H NMR (400 MHz: DMSO-d6, β isomer): ☐ 8.73 (s, 2H), 7.65-7.74 (m, 8H), 7.47-7.52 (m, 2H), 7.13-7.17 (m, 2H), 5.64 (d, 2H, J1-2=6.48 Hz, α-H-1), 5.34-5.36 (m, 2H), 4.76-4.81 (m, 4H), 4.49-4.53 (m, 2H), 3.61-3.73 (m, 2H), 3.54-3.58 (m, 6H), 3.08 (s, 6H).
Scheme 7 (FIG. 4E)

Synthesis of G638

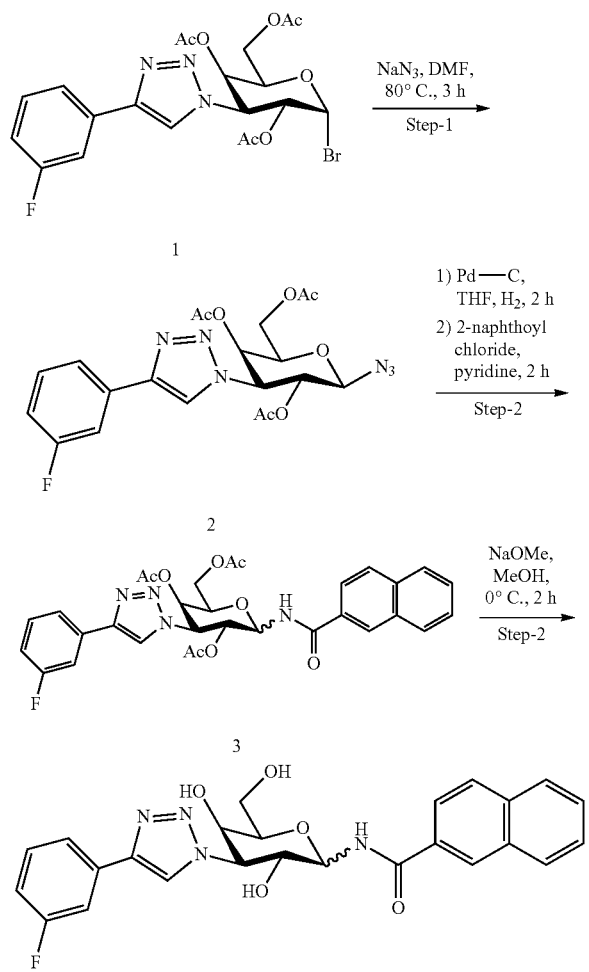

GTJC-013-15

Step-1:

(2R,3R,4S,5R,6R)-2-(acetoxymethyl)-6-azido-4-(4-(3-fluorophenyl)-1H-1,2,3-triazol-1-yl)tetrahydro-2H-pyran-3,5-diyl diacetate To a solution of (2R,3R,4S,5R,6R)-2-(acetoxymethyl)-6-bromo-4-(4-(3-fluorophenyl)-1H-1,2,3-triazol-1-yl)tetrahydro-2H-pyran-3,5-diyl diacetate (1.92 g, 3.74 mmol) in DMF (20 mL), NaN3 (1.21 g, 18.7 mmol) was added at room temperature. The reaction mixture was heated to 80° C. for 3 h. After completion, the reaction mixture was cooled to room temperature and quenched with cold water (20 mL). The aqueous layer was extracted with EtOAc (2×20 mL), dried (Na2SO4) and concentrated in vacuo. The crude residue was purified by flash column chromatography [normal phase, silica gel (100-200 mesh), gradient 0 to 50% EtOAc in hexane] to afford the title compound as a white solid (670 mg, 38%). ESIMS m/z 477 [M+H]+; 1H NMR (400 MHz, CDCl3): d 1.95 (s, 3H), 2.07 (s, 6H), 4.17-4.24 (m, 3H), 4.81 (d, J=8.5 Hz, 1H), 5.17 (dd, J=11.3 & 3.1 Hz, 1H), 5.59 (d, J=2.9 Hz, 1H), 5.62-5.70 (m, 1H), 7.02-7.06 (m, 1H), 7.35-7.41 (m, 1H), 7.52 (t, J=7.7 Hz, 2H), 7.80 (s, 1H), Step-2:

(3R,4S,5R,6R)-2-(2-naphthamido)-6-(acetoxymethyl)-4-(4-(3-fluorophenyl)-1H-1,2,3-triazol-1-yl)tetrahydro-2H-pyran-3,5-diyl diacetate To a solution of (2R,3R,4S,5R,6R)-2-(acetoxymethyl)-6-azido-4-(4-(3-fluorophenyl)-1H-1,2,3-triazol-1-yl)tetrahydro-2H-pyran-3,5-diyl diacetate (100 mg, 0.21 mmol) in THF (5 mL), Pd—C (20 mg, 10%, dry) was added and the reaction mixture was stirred under H2 (1 atm) at room temperature for 2 h. After completion, pyridine (0.05 mL, 0.63 mmol) was added to the reaction mixture, cooled to 0° C. and 2-naphthoyl chloride (80 mg, 0.42 mmol) was slowly added and stirred at room temperature for 2 h. After completion, the reaction mixture was filtered, washed with EtOAc (3×10 mL). The combined organic layers were washed with water (10 mL), dried (Na2SO4), and concentrated in vacuo to afford the title compound as a white sticky solid (158 mg, crude). ESIMS: m/z 605 [M+H]+.

Step-3:

N-((3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-2-naphthamide (GTJC-013-15)

To a solution of (3R,4S,5R,6R)-2-(2-naphthamido)-6-(acetoxymethyl)-4-(4-(3-fluorophenyl)-1H-1,2,3-triazol-1-yl)tetrahydro-2H-pyran-3,5-diyl diacetate (4, 158 mg, 0.26 mmol) MeOH (5 mL), NaOMe (0.26 mL, 1 M, 0.26 mmol) was added at 0° C. The reaction mixture was stirred at 0° C. for 2 h. After completion, the reaction mixture was acidified with Amberlyst 15 (pH ~6) and filtered. Washed with MeOH (3×10 mL) and concentrated in vacuo. The residue was purified by flash column chromatography [normal phase, silica gel (100-200 mesh), gradient 0 to 10% MeOH in DCM] to afford the title compound as a white solid (60 mg, 48%). LCMS: m/z 479 (M+H)+; (ES+) 70.96% at 4.80 min and 23.57% at 4.87 min. 1H NMR (400 MHz; DMSO-d6): ☐ 3.53 (t, J=5.9 Hz, 2H), 3.83 (t, J=6.1 Hz, 1H), 3.97-4.02 (m, 2H), 4.39-4.44 (m, 1H), 4.70-4.74 (m, 1H), 4.93 (dd, J=10.8, 2.8 Hz, 1H), 5.28 (d, J=6.7 Hz, 1H), 5.36 (d, J=6.7

Hz, 1H), 7.16 (td, J=8.8, 2.5 Hz, 1H), 7.46-7.52 (m, 1H), 7.59-7.66 (m, 2H), 7.69-7.76 (m, 2H), 7.96-8.07 (m, 4H), 8.50, 8.60 (each singlet, 1H), 9.27 (d, J=8.9 Hz, 1H).

Scheme 8 (FIG. 4F)

Synthesis of G633

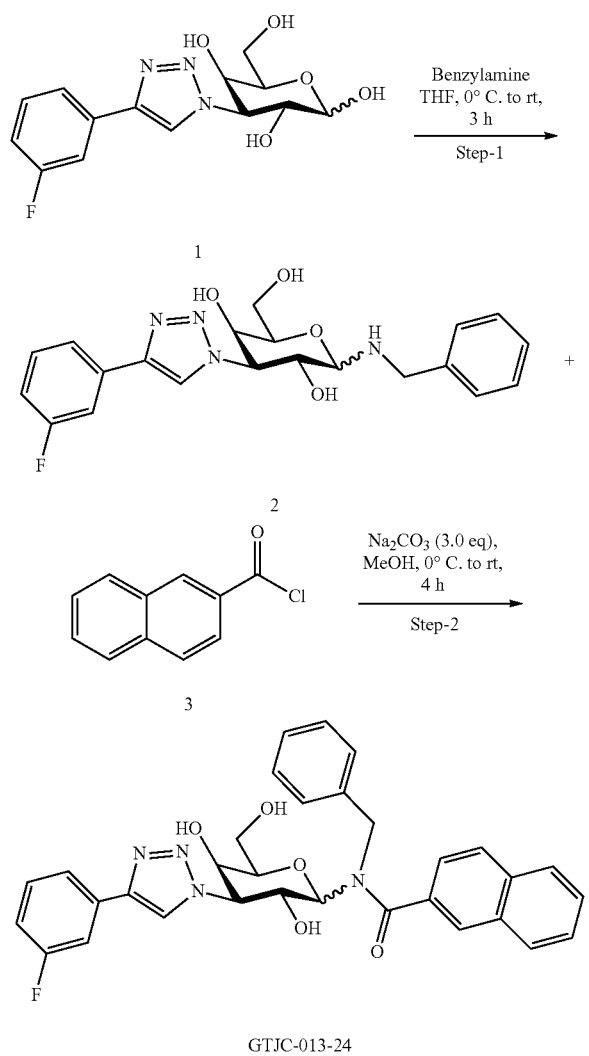

Step-1:

(3R,4S,5R,6R)-2-(benzylamino)-4-(4-(3-fluorophenyl)-1H-1,2,3-triazol-1-yl)-6-(hydroxymethyl)tetrahydro-2H-pyran-3,5-diol Benzylamine (87.1 mg, 0.8136 mmol) was added to a solution of (3R,4S,5R,6R)-4-(4-(3-fluorophenyl)-1H-1,2,3-triazol-1-yl)-6-(hydroxymethyl) tetra hydro-2H-pyran-2,3,5-triol (250 mg, 0.7396 mmol) in THF (2 mL) and the mixture was stirred at room temperature for 2 h. After completion, the reaction mixture was concentrated and the residue was triturated by Et2O to afford the title compound as a light yellow solid (150 mg). The crude material was used in next step. ESIMS: m/z 353 [M+H]+.

Step 2:

N-benzyl-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-O—2-naphthamide Na2CO3 (115.04 mg, 1.0869 mmol) and 2-naphthoyl chloride (190.99 mg, 0.7246 mmol) were added to a solution of (3R,4S,5R,6R)-2-(benzylamino)-4-(4-(3-fluorophenyl)-1H-1,2,3-triazol-1-yl)-6-(hydroxymethyl)tetrahydro-2H-pyran-3,5-diol (150 mg, 0.3623 mmol) in methanol (3 mL) at 0° C. The reaction mixture was stirred at room temperature. After completion, the reaction mixture was quenched with water (5 mL) and extracted with EtOAc (3×25 mL). The combined organic layers were washed with brine, dried (Na2SO4), filtered and concentrated under reduced pressure at 45° C. The residue was purified by prep HPLC to afford anomeric mixture the title compound as white solid (3 mg). HRMS (ESI) [M+H]+ calc. for C32H29FN4O5 568.21, found: 569.53 [M+H]+; LCMS: m/z 569.5 [M+H]+ (ES+) 96.83% at 5.59 min.

1H NMR (400 MHz; DMSO-d6, single β isomer): □ 8.70 (s, 1H), 8.24 (s, 1H), 8.07-8.08 (m, 1H), 7.98-8.01 (m, 2H), 7.51-7.71 (m, 7H), 7.46-7.51 (m, 1H), 7.31-7.35 (m, 2H), 7.20-7.24 (m, 1H), 7.12-7.17 (m, 1H), 5.66 (bs, 1H), 5.32 (bs, 1H), 5.06 (d, 1H, J1-2=7.72 Hz, α-H-1), 4.86-4.89 (m, 1H), 4.77-4.79 (m, 1H), 4.65-4.69 (m, 1H), 4.54-4.59 (m, 1H), 3.83 (s, 1H), 3.62-3.70 (m, 2H), 3.56-3.58 (m, 1H).

Synthesis of G639

N-benzyl-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)benzamide (GTJC-013-20)

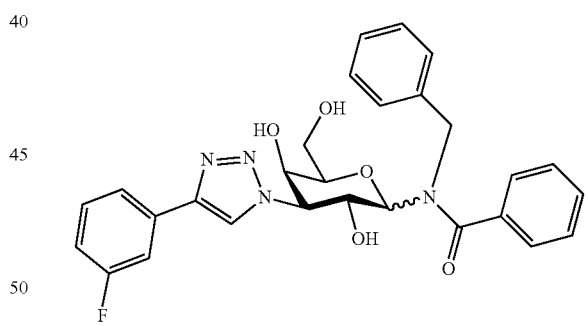

GTJC-013-20

Synthesized following the standard procedure used for GTJC-013-24

Appearance: white solid; synthesized: 1 mg

ESIMS: 949 [M+H]+; LCMS: m/z 697 (M+H)+ (ES+) 96.37% at 4.51 min,

1H NMR (400 MHz, DMSO-d6): □ 3.49-3.61 (m, 4H), 3.72 (t, J=6.2 Hz, 2H), 3.99 (dd, 6.6 & 2.9 Hz, 2H), 4.36-4.43 (m, 2H), 4.70 (t, J=5.5 Hz, 1H), 4.82 (dd, 10.5 & 2.8 Hz, 2H), 5.19 (d, J=9.7 Hz, 2H), 5.31 (d, J=7.2 Hz, 2H), 5.40 (d, J=6.6 Hz, 2H), 7.12-7.17 (m, 2H), 7.46-7.51 (m, 2H), 7.66 (dd, J=10.2 & 2.3 Hz, 2H), 7.72 (d, J=7.8 Hz, 2H), 8.67 (s, 2H).

Figure 4G:
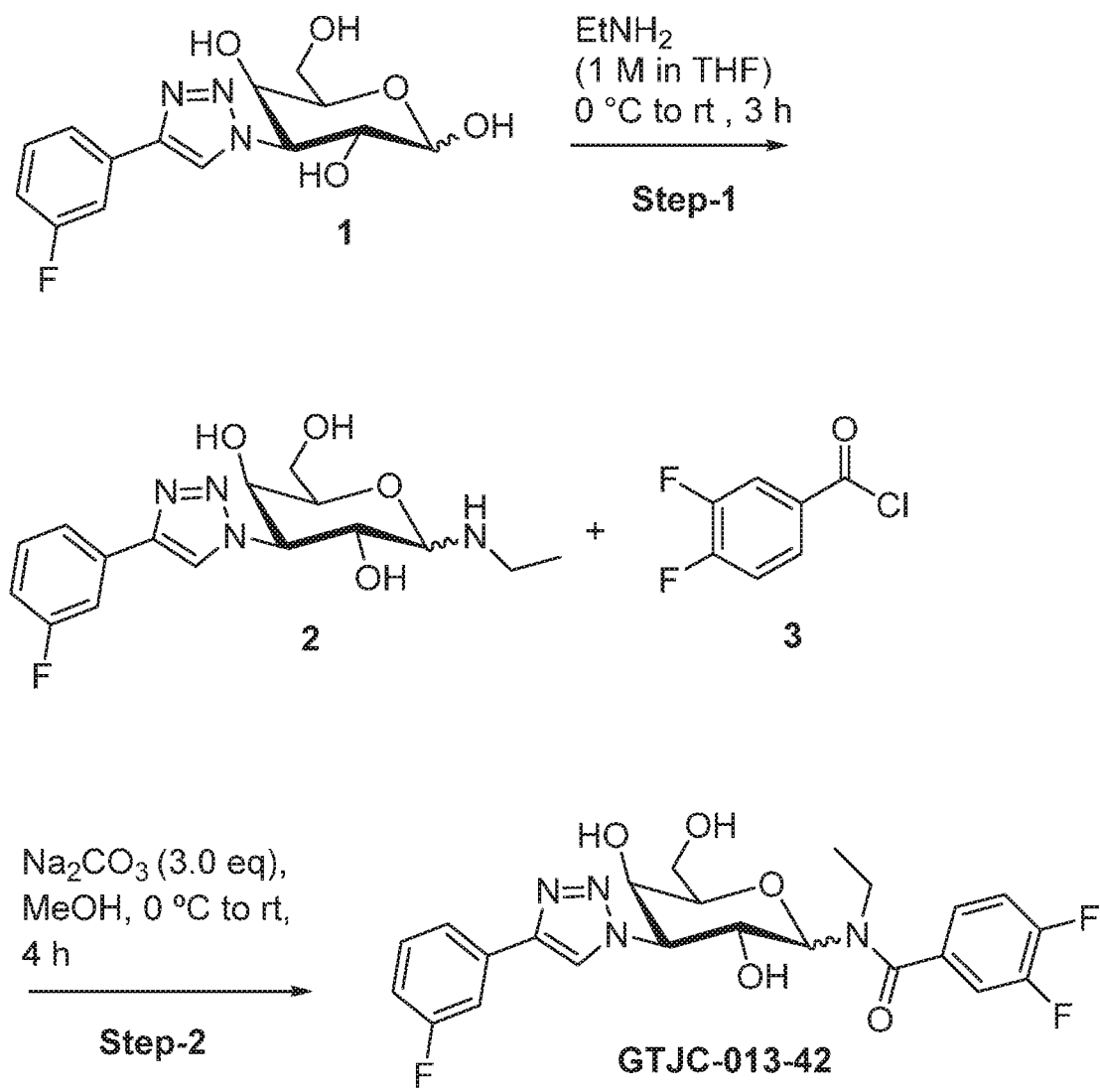

Scheme 9 (FIG. 4G)

Synthesis of G643

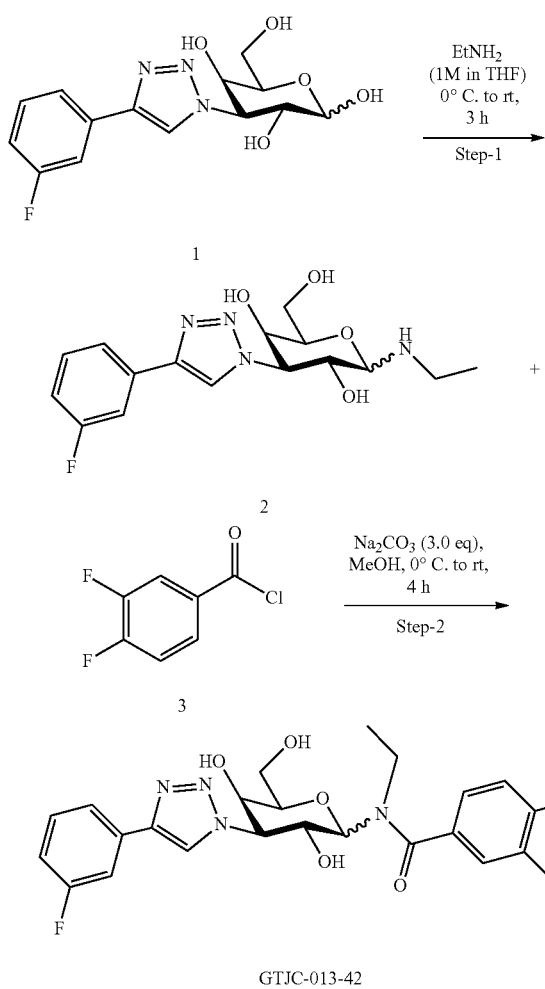

Step 1:

(3R,4S,5R,6R)-2-(ethylamino)-4-(4-(3-fluorophenyl)-1H-1,2,3-triazol-1-yl)-6-(hydroxymethyl)tetrahydro-2H-pyran-3,5-diol (2)

A solution of (3R,4S,5R,6R)-4-(4-(3-fluorophenyl)-1H-1,2,3-triazol-1-yl)-6-(hydroxymethyl) tetra hydro-2H-pyran-2,3,5-triol (3, 150 mg, 1.53 mmol) in ethylamine (1.0 M in THF, 2 mL) was stirred at room temperature for 2 h. After completion, the reaction mixture was concentrated in vacuo. The resulting crude residue was triturated by Et2O to afford the title compound as a light yellow solid (100 mg, crude). The material was taken for next step without further purification. HRMS (ESI) [M+H]+ calc. for C16H21FN4O4 352.15, found: 353.33 [M+H]+; ESIMS: m/z 353 [M+H]+.

Step-2:

N-ethyl-3,4-difluoro-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)benzamide (GTJC-013-42)

To a solution of (3R,4S,5R,6R)-2-(ethylamino)-4-(4-(3-fluorophenyl)-1H-1,2,3-triazol-1-yl)-6-(hydroxymethyl)tetrahydro-2H-pyran-3,5-diol (100 mg, 0.2840 mmol) in methanol (3 mL) was added Na2CO3 (90.04 mg, 0.8522 mmol) and 3,4-difluorobenzoyl chloride (99.99 mg, 0.5681 mmol) at 0° C. The reaction mixture was stirred at room temperature. After 3 h, the reaction mixture was quenched with water (5 mL) and extracted with EtOAc (3×25 mL). The combined organic layers were washed with brine and dried (Na2SO4). The solvent was removed under reduced pressure at 45° C. and the residue was purified by flash column chromatography by using 4.5% Methanol in DCM to afford the title compound as white solid (15 mg, 11%).

HRMS (ESI) [M+H]+ calc. for C23H23F3N4O5 492.16, found: 493.47 [M+H]+

LCMS: m/z 493.4 [M+H]+ (ES+), at 5.28 min (93.45%) & 5.39 min (6.26%).

1H NMR (400 MHz; DMSO-d6, anomeric mixture α:β=1:15): □ 8.75 (s, 1H), 7.71-7.76 (m, 1H), 7.65-7.69 (m, 1H), 7.48-7.59 (m, 3H), 7.41-7.47 (m, 1H), 7.12-7.17 (m, 1H), 5.50 (d, 1H, J1-2=6.92 Hz, α-H-1), 5.34 (d, J=6.48 Hz, 1H), 4.62-4.79 (m, 3H), 4.42-4.49 (m, 1H), 3.82 (bs, 1H), 3.66-3.69 (m, 1H), 3.32-3.54 (m, 4H), 1.25 (m, 3H).

Figure 4H:
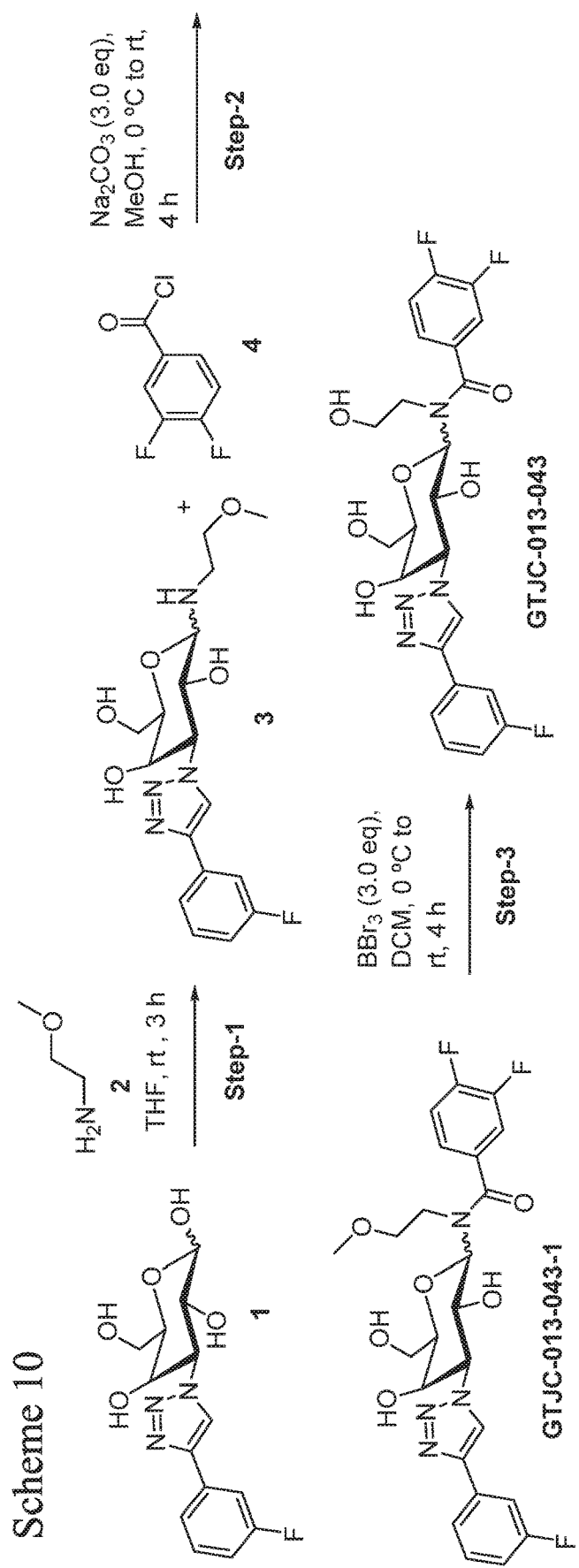
Figure 4J:
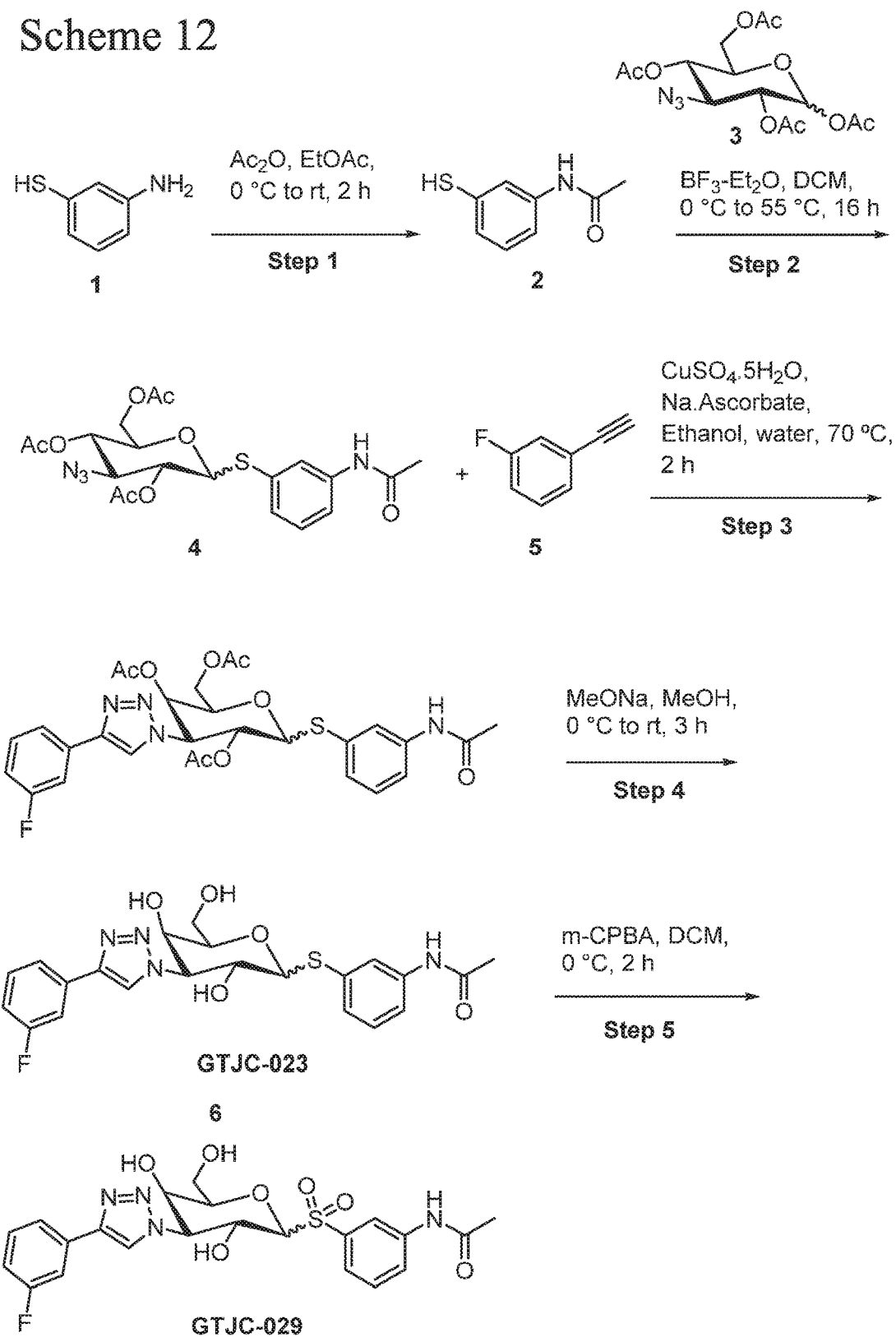

Scheme 10 (FIG. 4H)

Synthesis of G654

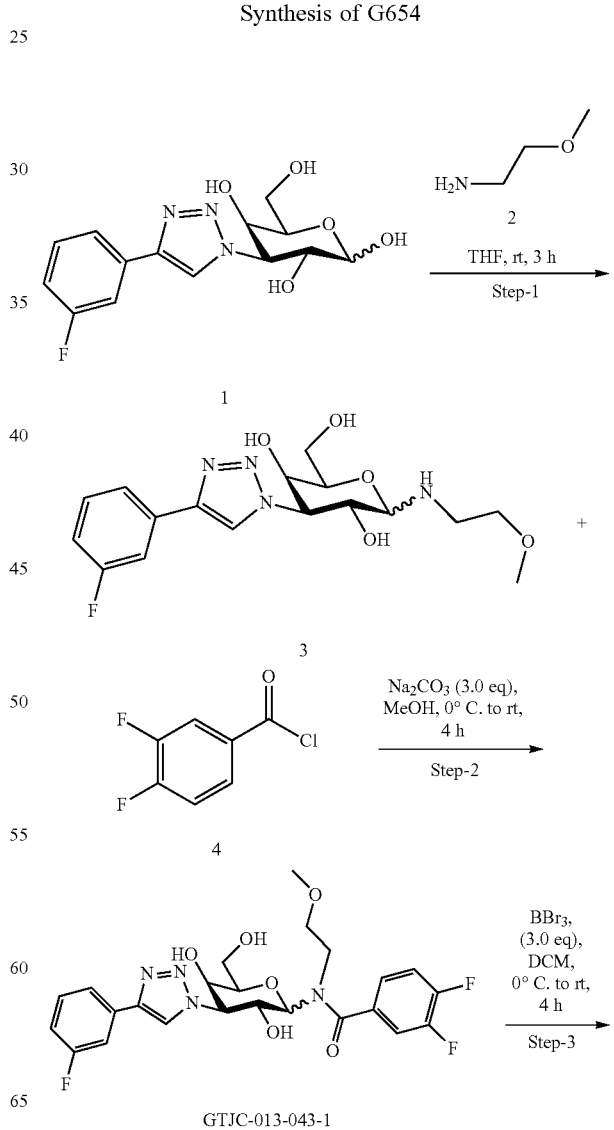

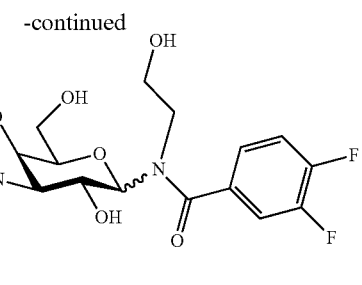

GTJC-013-043

Step 1:

(2R,3R,4S,5R,6R)-4-(4-(3-fluorophenyl)-1H-1,2,3-triazol-1-yl)-2-(hydroxymethyl)-6-((2-methoxyethyl)amino)tetrahydro-2H-pyran-3,5-diol (3)

2-methoxyethan-1-amine 2 (93.25 mg, 1.226 mmol) was added to a solution of (3R,4S,5R,6R)-4-(4-(3-fluorophenyl)-1H-1,2,3-triazol-1-yl)-6-(hydroxymethyl) tetra hydro-2H-pyran-2,3,5-triol (1, 200 mg, 0.613 mmol) in THF (5 ml) and the mixture was stirred at room temperature for 2 h. After completion, the reaction mixture was concentrated in vacuo and the residue was triturated by Et2O to afford the title compound as a light yellow solid (170 mg, crude. The material was taken for next step. HRMS (ESI) [M+H]+ calc. for C17H23FN4O5 382.17, found: 383.17 [M+H]+; ESIMS: m/z 383 [M+H]+.

Step 2:

3,4-difluoro-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-(2-methoxyethyl)benzamide (GTJC-013-43-1)

To a solution of (2R3R,4S,5R,6R)-4-(4-(3-fluorophenyl)-1H-1,2,3-triazol-1-yl)-2-(hydroxymethyl)-6-((2-methoxyethyl)amino)tetrahydro-2H-pyran-3,5-diol (150 mg, 0.3926 mmol) in methanol (3 mL) was added Na2CO3 (124.8 mg, 1.1780 mmol) and 3,4-difluorobenzoyl chloride (138.02 mg, 0.7853 mmol) at 0° C. The reaction mixture was stirred at room temperature. After 3 h, the reaction mixture was quenched with water (5 mL) extracted with EtOAc (3×25 mL). The combined organic phase was washed with brine and dried (Na2SO4). The solvent was removed under reduced pressure at 45° C. and the residue was purified by flash column chromatography by using 2% Methanol in DCM to afford the title compound as a white solid (110 mg, 54%). HRMS (ESI) [M+H]+ calc. for C24H25F3N4O6 522.17, found: 523.58 [M+H]+

1H NMR (400 MHz, DMSO-d6, with D2O, β isomer): □ 8.76 (s, 1H), 7.71-7.75 (m, 1H), 7.68-7.71 (m, 1H), 7.56-7.68 (m, 3H), 7.47-7.51 (m, 1H), 7.12-7.17 (m, 1H), 5.47 (d, 1H, J1-2=6.44 Hz, α-H-1), 5.36 (d, J=6.56 Hz, 1H), 4.83-4.85 (m, 1H), 4.76-4.78 (m, 2H), 4.43-4.50 (m, 1H), 3.83-3.88 (m, 2H), 3.48-3.56 (m, 6H), 3.29 (s, 3H).

Step 3:

3,4-difluoro-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-(2-hydroxyethyl)benzamide (GTJC-013-43)

To a solution of 3,4-difluoro-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-(2-methoxyethyl)benzamide (80 mg, 0.1532 mmol) in DCM (4 mL) BBr3 (115.4 mg, 0.4597 mmol) was added at 0° C. The reaction mixture was stirred at room temperature for 3 h. After completion, the reaction mixture was quenched with saturated NaHCO3 solution (6 mL) to adjust pH~8 and extracted with DCM (3×25 mL). The combined organic phase was washed with brine and dried (Na2SO4) filtered and concentrated under reduced pressure at 45° C. The residue was purified by prep HPLC to afford the title compound as a white solid (6 mg, 8%).

HRMS (ESI) [M+H]+ calc. for C23H23F3N4O6 508.16, found: 509.5 [M+H]+

LCMS: m/z 509.5 (M+H)+ (ES+) 59.89% at 4.57 min, 29.86% at 4.66 min, 9.66% at 4.76 min.

1H NMR (400 MHz; DMSO-d6, mixture of 3 isomers): 8.69 (s, 1H), 7.45-7.77 (m, 6H), 7.13-7.18 (m, 1H), 5.56 (d, 1H, J1-2=6.16 Hz, α-H-1). 5.37 (d, J=6.4 Hz, 1H), 4.41-5.04 (m, 5H), 3.48-4.28 (m, 8H).

Scheme 11 (FIG. 4I)

Synthesis of G631

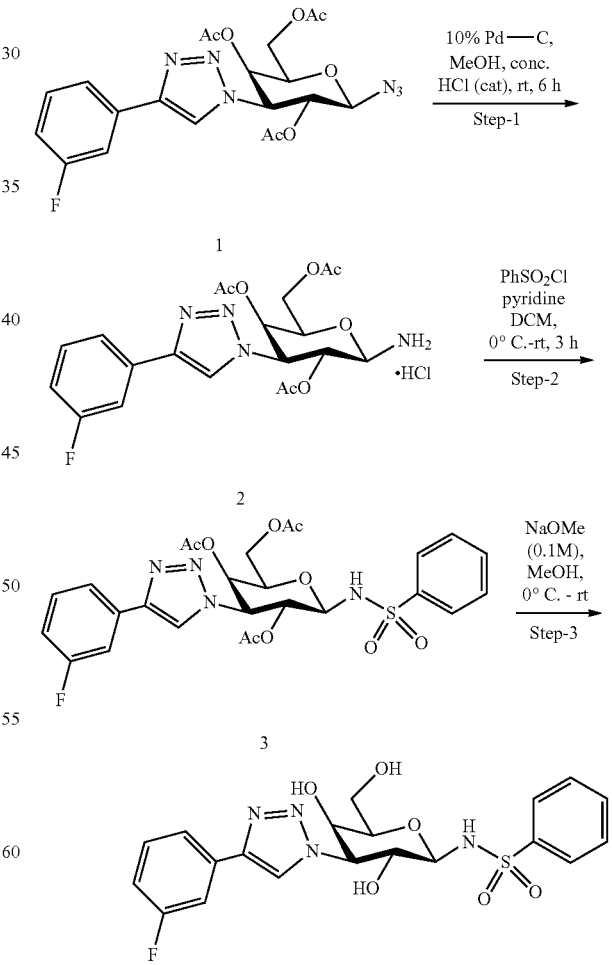

GTJC-026

Step 1:

(2R,3R,4S,5R)-2-(acetoxymethyl)-6-amino-4-(4-(3-fluorophenyl)-1H-1,2,3-triazol-1-yl)tetrahydro-2H-pyran-3,5-diyl diacetate hydrochloride (3)

10% Pd—C (50 mg) and conc. HCl (two drops) were added solution of (2R,3R,4S,5R)-2-(acetoxymethyl)-6-azido-4-(4-(3-fluorophenyl)-1H-1,2,3-triazol-1-yl)tetrahydro-2H-pyran-3,5-diyl diacetate (115 mg, 0.2415 mol) in Methanol (3 mL). The mixture was stirred under hydrogen atmosphere (balloon pressure) at room temperature for 2 h. After completion, the reaction mixture was filtered through celite, washed with methanol (10 mL). The combined filtrate was concentrated in vacuo to afford the title compound as an off white solid (93 mg, 86%). The residue was used in next step without further purification. 1H NMR (400 MHz, CDCl3): ☐ 2.04 (s, 3H), 2.06 (s, 3H), 2.18 (s, 3H), 2.45 (s, 3H), 2.76-2.80 (m, 1H), 4.03-4.17 (m, 3H), 5.44-5.53 (m, 3H), 7.27 (d, J=8.1 Hz, 2H), 7.75 (d, J=8.1 Hz, 2H).

Step 2:

(2R,3R,4S,5R,6R)-2-(acetoxymethyl)-4-(4-(3-fluorophenyl)-1H-1,2,3-triazol-1-yl)-6-(phenylsulfonamido)tetrahydro-2H-pyran-3,5-diyl diacetate (4)

To a solution of (2R,3R,4S,5R)-2-(acetoxymethyl)-6-amino-4-(4-(3-fluorophenyl)-1H-1,2,3-triazol-1-yl)tetrahydro-2H-pyran-3,5-diyl diacetate hydrochloride (3, 93 mg 0.1913 mmol) in DCM (5 mL) pyridine (46 mg, 0.5740 mmol) and benzene sulfonyl chloride chloride (50.69 mg, 0.2870 mmol) were added at 0° C. The reaction mixture was stirred at room temperature for 3 h. After completion, the reaction mixture was quenched with water (3 mL) and extracted with DCM (3×15 mL). The combined organic layers were dried (Na2SO4) and concentrated in vacuo to afford the title compound as an off white semi solid (130 mg, crude). HRMS (ESI) [M+H]+ calc. for C26H27FN4O9S 590.15, found: 591.32 [M+H]+; 1H NMR (400 MHz, DMSO-d6): ☐ 3.49-3.61 (m, 4H), 3.72 (t, J=6.2 Hz, 2H), 3.99 (dd, 6.6 & 2.9 Hz, 2H), 4.36-4.43 (m, 2H), 4.70 (t, J=5.5 Hz, 1H), 4.82 (dd, 10.5 & 2.8 Hz, 2H), 5.19 (d, J=9.7 Hz, 2H), 5.31 (d, J=7.2 Hz, 2H), 5.40 (d, J=6.6 Hz, 2H), 7.12-7.17 (m, 2H), 7.46-7.51 (m, 2H), 7.66 (dd, J=10.2 & 2.3 Hz, 2H), 7.72 (d, J=7.8 Hz, 2H), 8.67 (s, 2H).

Step 3:

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)benzenesulfonamide (GTJC-026)

To a solution of (2R,3R,4S,5R,6R)-2-(acetoxymethyl)-4-(4-(3-fluorophenyl)-1H-1,2,3-triazol-1-yl)-6-(phenylsulfonamido)tetrahydro-2H-pyran-3,5-diyl diacetate (120 mg, 0.203 mmol) in MeOH (5 mL), NaOMe (0.46 mL, 1 M, 0.46 mmol) was slowly added at 0° C. The reaction mixture was stirred at room temperature for 2 h. After completion, the reaction mixture was acidified with Amberlyst 15 resin (pH~5) filtered, washed with MeOH (3×5 mL) and concentrated in vacuo. The residue was purified by prep HPLC to afford anomeric mixture of the title compound (GTJC-026-P1, 3 mg, mixture of 4 isomers, GTJC-026-P2, 1 mg, anomeric mixture, α:β=1:12) as a white solids.

HRMS (ESI) [M+H]+ calc. for C20H21FN4O6S 464.12, found: 465.42 [M+H]+

LCMS: (GTJC-026-P1) m/z 465.4 [M+H]+ (ES+) 58.97% at 4.33 min, 27.97% at 4.38 min, 6.57% at 4.55 min & 2.61% 4.74 min.

1H NMR (GTJC-026-P1) (400 MHz; DMSO-d6, mixture of 4 isomers): ☐ 8.60 (s, 0.5H), 8.58 (s, 0.5H), 7.87-7.90 (m, 2H), 7.62-7.74 (m, 2H), 7.46-7.61 (m, 4H), 7.12-7.16 (m, 1H), 5.38 (d, 1H, J1-2=7.12 Hz, α-H-1), 3.63-5.39 (m, 7H), 3.10-3.13 (m, 2H), 2.49-2.58 (m, 1H).

LCMS: (GTJC-026-P2) m/z 465.38 [M+H]+, (ES+) 89.0% at 4.33 min and 7.34% at 4.38 min.

1H NMR (GTJC-026-P2) (400 MHz; DMSO-d6, anomeric mixture, α:β=1:12): ☐ 8.76 (bs, 1H), 8.48 (s, 1H), 7.89 (d, J=7.32, 2H), 7.68-7.72 (m, 2H), 7.46-7.62 (m, 4H), 7.12-7.17 (m, 1H), 5.40 (d, 1H, J1-2=7.12 Hz, α-H-1), 5.26 (d, J=5.7, 1H), 4.83-4.86 (m, 1H), 4.69 (d, J=8.56, 1H), 4.40-4.52 (m, 1H), 3.89-3.90 (m, 1H), 3.62-3.65 (m, 1H), 3.09-3.14 (m, 1H), 2.50 (s, 1H).

Synthesis of G630

N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)benzenesulfonamide (GTJC-055)

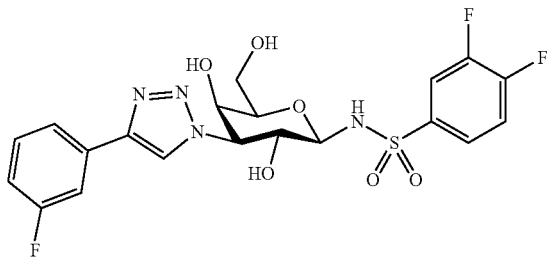

Synthesized following the standard procedure used for GTJC-026

Appearance: White solid

Synthesized: (GTJC-055-P1, 3 isomers, 15 mg) and (GTJC-055-P2, 4 isomers, 8 mg)

HRMS (ESI) [M+H]+ calc. for C20H19F3N4O6S 500.10, found: 501.20 [M+H]+

LCMS (GTJC-055-P1,): m/z 501 [M+H]+ (ES+), 78.32% at 4.66 min, 7.41% at 4.72 min & 12.44% 4.83 min.

1H NMR (GTJC-055-P1) (400 MHz; DMSO-d6): ☐ 8.55 (s, 1H), 7.81-7.91 (m, 1H), 7.60-7.74 (m, 4H), 7.46-7.51 (m, 1H), 7.12-7.17 (m, 1H), 5.43 (d, 1H, J1-2=7.12 Hz, α-H-1), 5.26 (d, 1H, J=5.88 Hz), 4.83-4.86 (m, 1H), 4.67-4.69 (m, 1H), 4.54-4.57 (m, 1H), 4.01-4.04 (m, 1H), 3.89 (be, 1H), 3.66-3.69 (m, 1H), 3.32-3.37 (m, 1H), 3.16-3.19 (m, 1H).

LCMS (GTJC-055-P2,): m/z 501 [M+H]+ (ES+), 62.43% at 4.66 min, 24.51% at 4.72 min, 5.63% 4.85 min & 3.81% 5.04 min.

1H NMR (GTJC-055-P2) (400 MHz, DMSO-d6) ☐ 8.50 (s, 1H), 7.83-7.94 (m, 1H), 7.60-7.74 (m, 5H), 7.46-7.51 (m, 1H), 7.17-7.27 (m, 1H), 5.43 (d, 1H, J1-2=7.2 Hz, α-H-1), 5.24-5.27 (m, 1H), 4.83-4.86 (m, 1H), 4.68 (d, J=8.5 Hz, 1 H), 4.46-4.57 (m, 1H), 4.02-4.04 (m, 1H), 3.89 (m, 1H), 3.66-3.67 (m, 1H), 3.31-3.35 (m, 1H), 3.16-3.19 (m, 1H).

Scheme 12 (FIG. 4J)
Synthesis of G632
Step 1:
N-(3-mercaptophenyl)acetamide (2): To a solution of 3-aminobenzenethiol (2 g, 16.0 mmol) in EtOAc (50 mL), Ac2O (1.66 mL, 17.6 mmol) was slowly added at 0° C. and
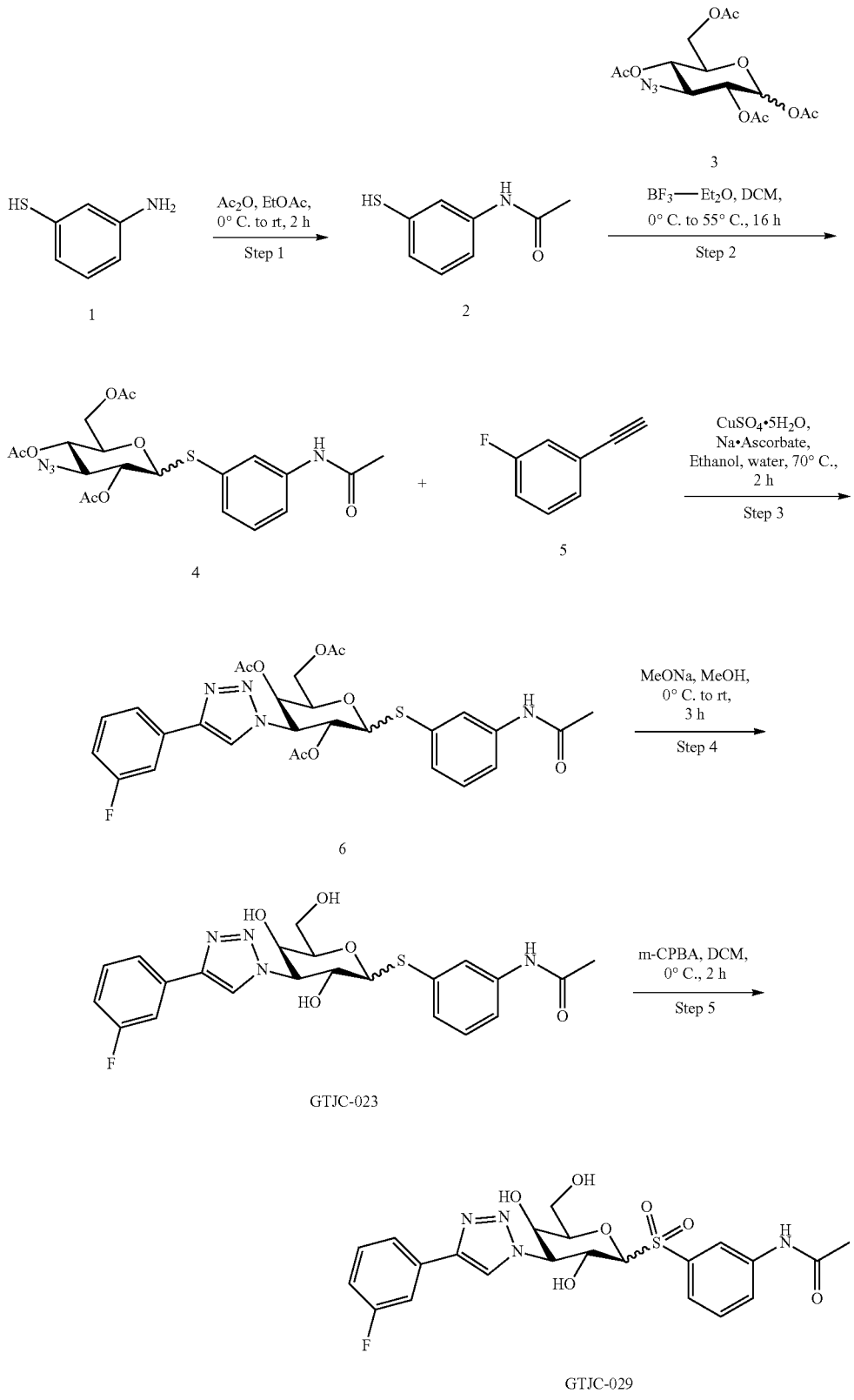
GTJC-023
GTJC-029 the reaction mixture was stirred at room temperature for 2 h. After completion, the reaction mixture was quenched with water (40 mL). After separating the organic layer, the aq layer was extracted with EtOAc (2×10 mL). The combined organic layers were washed with brine, dried (Na2SO4) and concentrated in vacuo to afford the title compound as light brown sticky solid (2.23 g, 83%). ESIMS: m/z 166 [M+H]+; 1H NMR (400 MHz, DMSO-d6): ☐ 2.02 (s, 3H), 5.39 (bs, 1H), 6.94 (d, J=7.6 Hz, 1H), 7.14 (t, J=8.0 Hz, 1H), 7.23 (d, J=8.0 Hz, 1H), 7.60 (s, 1H), 9.90 (s, 1 H).

Step 2:

(3R,4S,5R,6R)-2-((3-acetamidophenyl)thio)-6-(acetoxymethyl)-4-azidotetra hydro-2H-pyran-3,5-diyl diacetate (4)

A solution of N-(3-mercaptophenyl)acetamide (2, 161 mg, 0.96 mmol) and (3R,4S,5R,6R)-6-(acetoxymethyl)-4-azidotetrahydro-2H-pyran-2,3,5-triyl triacetate (180 mg, 0.48 mmol) in DCM (20 mL), BF3.Et2O (304 mg, 0.96 mmol) was slowly added at 0° C. and the reaction mixture was heated at 55° C. for 16 h. After completion, the reaction mixture was quenched with water (10 mL) and extracted with DCM (3×10 mL). The combined organic layers were washed with brine, dried (Na2SO4) and concentrated in vacuo. The crude residue was purified by flash column chromatography [normal phase, silica gel (100-200 mesh), gradient 0% to 70% EtOAc in hexane] to afford the title compound as a off white solid (177 mg, 77%), The crude residue was used for the next step without further purification. ESIMS: m/z 481 [M+H]+

Step 3:

(3R,4S,5R,6R)-2-((3-acetamidophenyl)thio)-6-(acetoxymethyl)-4-(4-(3-fluorophenyl)-1H-1,2,3-triazol-1-yl)tetrahydro-2H-pyran-3,5-diyl diacetate (6)

To a solution of (3R,4S,5R,6R)-2-((3-acetamidophenyl) thio)-6-(acetoxymethyl)-4-azidotetra hydro-2H-pyran-3,5-diyl diacetate (230 mg 0.48 mmol) and 1-ethynyl-3-fluorobenzene (121 mg, 0.96 mmol) in EtOH (5 mL) and water (5 mL), sodium ascorbate (43 mg, 0.21 mmol) and CuSO4.5H2O (32 mg, 0.07 mmol) were added at room temperature. The reaction mixture was heated to 70° C. for 2 h. After completion, the reaction mixture was diluted with EtOAc (10 mL) and filtered through a pad of celite, washed with EtOAc (3×10 mL), and concentrated in vacuo to afford the title compound as an off white solid (243 mg, 84%). The crude residue was used for the next step without further purification. ESIMS: m/z 601 [M+H]+.

Step 4:

Synthesis of N-(3-(((3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)thio)phenyl) acetamide (GTJC-023)

To a solution of (3R,4S,5R,6R)-2-((3-acetamidophenyl) thio)-6-(acetoxymethyl)-4-(4-(3-fluorophenyl)-1H-1,2,3-triazol-1-yl)tetrahydro-2H-pyran-3,5-diyl diacetate (180 mg, 0.3 mmol) in MeOH (5 mL), NaOMe (0.3 mL, 1 M, 0.3 mmol) was slowly added at 0° C. and stirred at rt for 3 h. After completion, the reaction mixture was acidified with Amberlyst 15 resin (pH~5), filtered, washed with MeOH (3×10 mL) and concentrated in vacuo. The crude residue was purified by flash column chromatography [normal phase, silica gel (100-200 mesh), gradient 0% to 10% MeOH in DCM]. The white solid obtained was triturated with Et2O to afford the title compound as a white solid (68 mg, 48%).
LCMS: m/z 475 (M+H)+ (ES+), 75.88% at 4.40 min and 22.76% at 4.63 min.
1H NMR (400 MHz; DMSO-d6): ☐ 2.04 (s, 3H), 3.35-4.05 (overlapping signals, m, 4H), 4.12-5.67 (overlaping signals, m, 6H), 7.23-7.31 (m, 3H), 7.36-7.52 (m, 2H), 7.67-7.76 (m, 2H), 7.80 (s, 1H), 8.69, 8.88 (each singlet, 1H), 9.96, 10.01 (each singlet, 1H).

Step 5:

N-(3-(((3R,4S,5R,6R)-4-(4-(3-fluorophenyl)-1H-1,2,3-triazol-1-yl)-3,5-dihydroxy-6-(hydroxymethyl) tetrahydro-2H-pyran-2-yl)sulfonyl)phenyl)acetamide (GTJC-029)

To a solution of N-(3-(((3R,4S,5R,6R)-4-(4-(3-fluorophenyl)-1H-1,2,3-triazol-1-yl)-3,5-dihydroxy-6-(hydroxymethyl) tetrahydro-2H-pyran-2-yl)thio)phenyl)acetamide (30 mg, 0.063 mmol) in DCM (4 mL), m-CPBA (15 mg, 0.063 mmol) was added at 0° C. and stirred at same temperature for 2 h. After completion, the reaction mixture was quenched with aq. NaOH (10 mL, 2 M) and the aq. layer was extracted with DCM (3×10 mL). The combined organic layers were washed with brine, dried (Na2SO4) and concentrated in vacuo. The residue was triturated with Et2O to afford the title compound as a white solid (16 mg, 50%).
LCMS: m/z 475 [M+H]+ (ES+), 22.84% at 4.18 min, 64.79% at 4.29 min, 8.33% at 4.41 min, 2.40% at 4.91 min.
1H NMR (400 MHz, DMSO-d6): ☐ 2.07, 2.08 (each singlet, 3H), 3.26-3.31 (m, 1H), 3.40-4.74 (overlaping signals, m, 6H), 4.96 (dd, J=10.6 & 2.3 Hz, 1H), 5.22-5.98 (overlaping signals, m, 2H), 7.13-7.17 (m, 1H), 7.46-7.62 (m, 3H), 7.67-7.78 (m, 2H), 7.83-7.88 (m, 1H), 8.20, 8.21, 8.27 (each singlet, 1H). 8.67, 8.68, 8.77 (each singlet, 1H), 10.29, 10.30, 10.34 (each singlet, 1H).

Figure 4K:
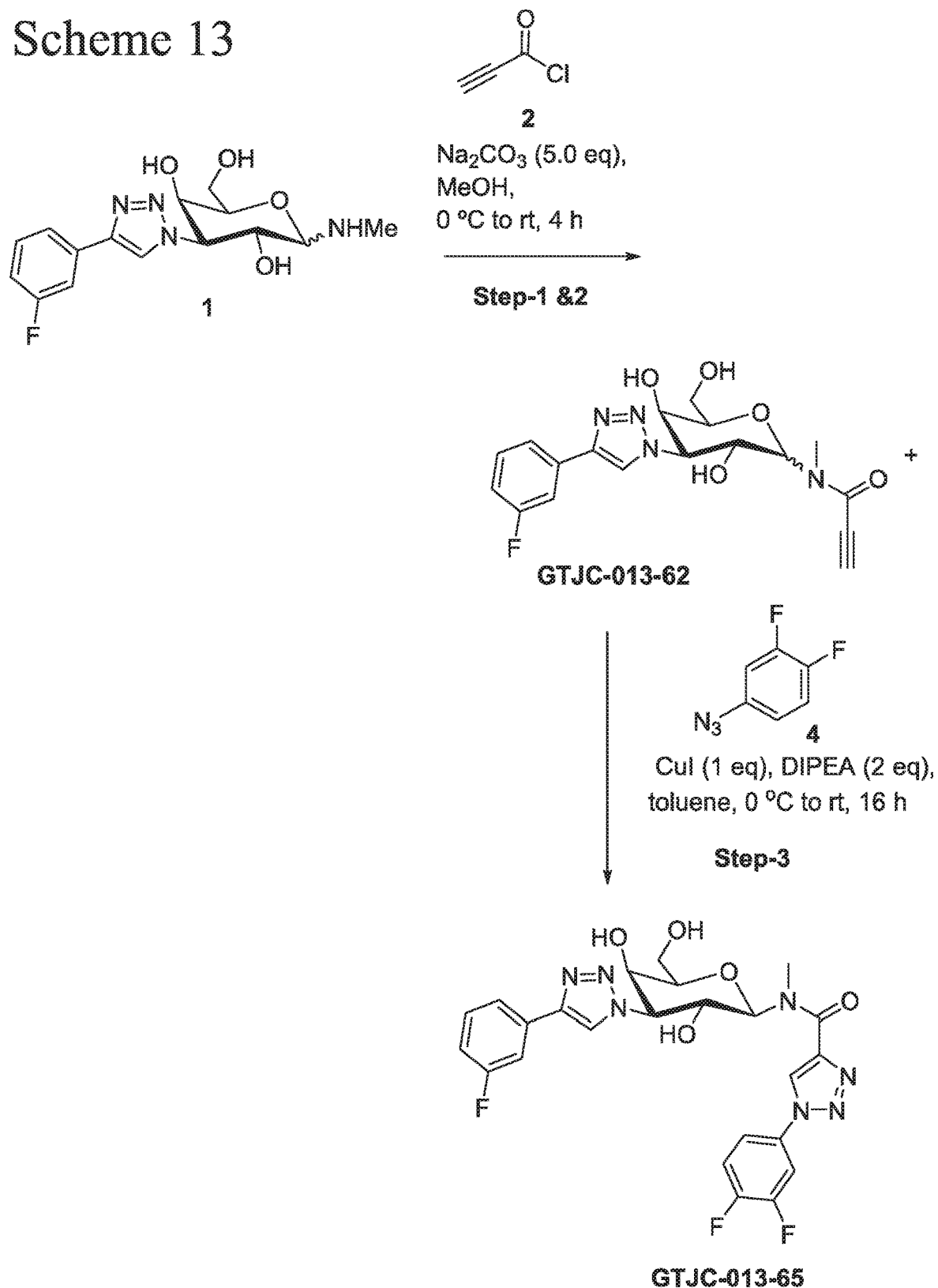
Figure 4K:
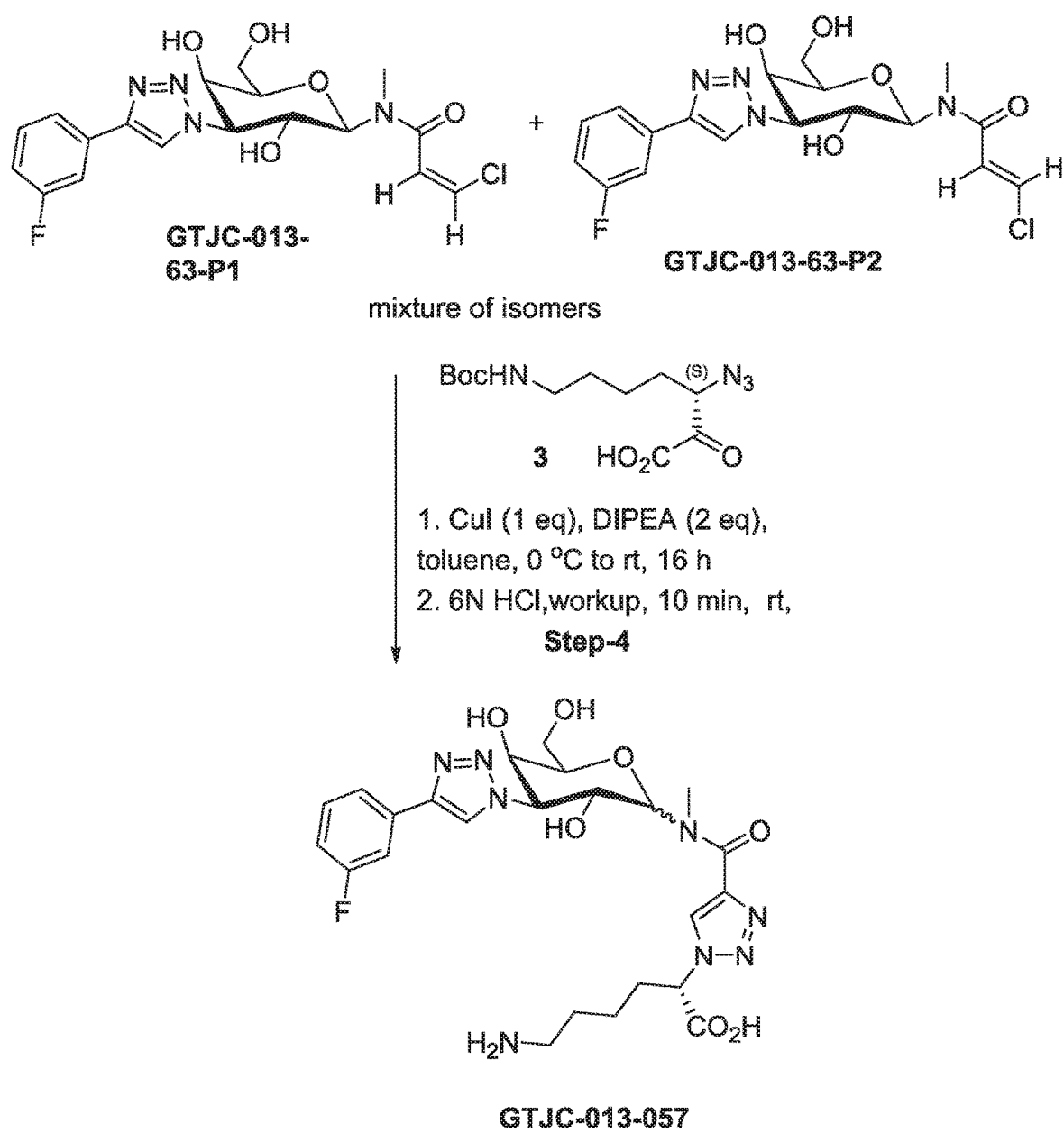

Scheme 13 (FIG. 4K)

Synthesis of G670

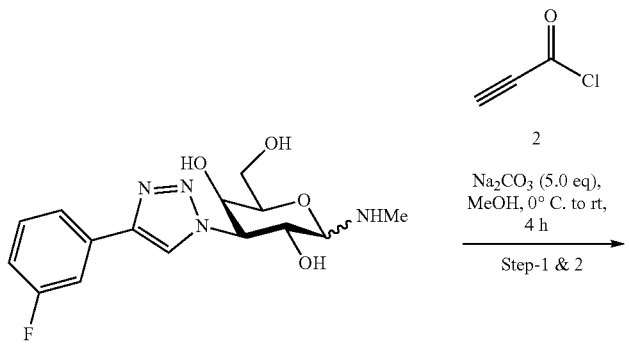

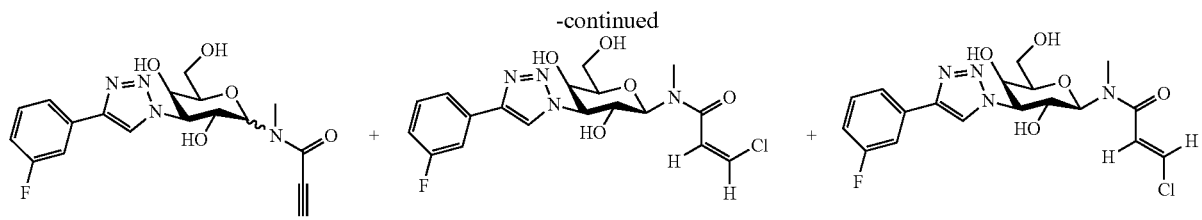

GTJC-013-62

GTJC-013-63-P1

GTJC-013-63-P2 mixture of isomers

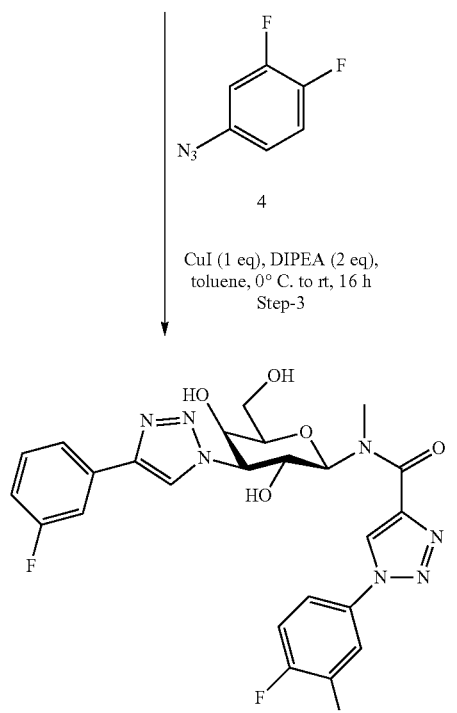

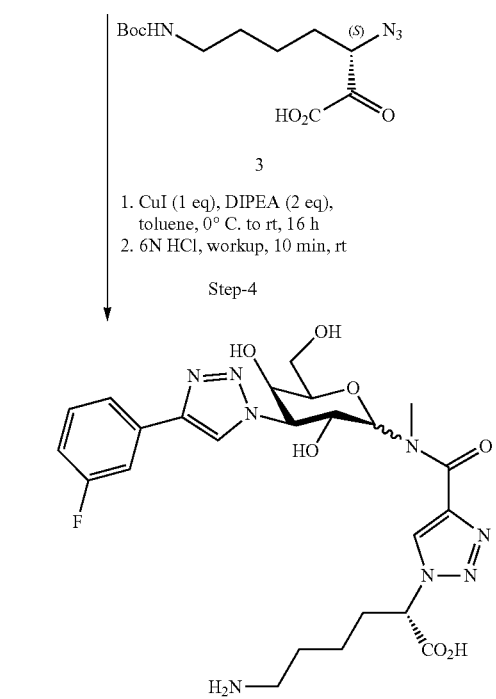

Steps 1 and 2:

N-((3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylpropiolamide (GTJC-013-62)

To a solution of (2R,3R,4S,5R,6R)-4-(4-(3-fluorophenyl)-1H-1,2,3-triazol-1-yl)-2-(hydroxymethyl)-6-(methylamino)tetrahydro-2H-pyran-3,5-diol (300 mg, 0.8875 mmol) in MeOH (10 mL), Na2CO3 (940 mg, 8.8757 mmol) was added and the reaction mixture was cooled to 0° C. propioloyl chloride (156 mg, 1.7751 mmol) was slowly added at 0° C. and the reaction mixture was stirred at room temperature for 2 h. After completion, the reaction mixture was concentrated in vacuo. The crude residue was purified by flash column chromatography [normal phase, silica gel (100-200 mesh), gradient 0 to 10% MeOH in DCM] to give mixture of N-((3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylpropiolamide (GTJC-013-62, single β isomer, 2 mg) as a white solid, (Z)-3-chloro-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylacrylamide (GTJC-013-63-P1, single β isomer, 2 mg) as a white solid and (E)-3-chloro-N-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylacrylamide(GTJC-013-63-P2, single β isomer, 1 mg) as a white solid.

HRMS (ESI) [M+H]+ calc. for C18H19FN4O5 390.13, found: 391.16 [M+H]+

LCMS (GTJC-013-62): m/z 391 [M+H]+ (ES+) 95.11% at 3.88 min.

1H-NMR (400 MHz; DMSO-d6, (GTJC-013-62, single β isomer)): ☐ 8.74 (s, 1H), 7.73-7.75 (m, 1H), 7.68-7.70 (m, 1H), 7.47-7.52 (m, 1H), 7.13-7.17 (m, 1H), 5.66 (d, 1H, J1-2=6.12 Hz, α-H-1), 3.80-5.51 (m, 7H), 3.51-3.53 (m, 2H), 3.15-3.17 (m, 2H), 2.89 (s, 2H).

HRMS (ESI) [M+H]+ calc. for C18H20ClFN4O5 426.11, found: 427.11 [M+H]+

LCMS (GTJC-013-63-P1): m/z 427.1 [M+H]+ (ES+) 93.52% at 3.96 min.

1H NMR (400 MHz, DMSO-d6, (GTJC-013-63-P1, single β isomer)): ☐ 8.73 (s, 1H), 7.53-7.75 (m, 1H), 7.68-7.70 (m, 1H), 7.47-7.52 (m, 1H), 7.13-7.17 (m, 1H), 6.74-6.76 (m, 1H), 6.65-6.67 (m, 1H), 5.60 (d, 1H, J1-2=8.6 Hz, α-H-1), 5.30-5.37 (m, 1H), 4.91-4.95 (m, 2H), 4.74 (m,1H), 4.37 (m, 1H), 3.92 (m, 1H), 3.81 (t, J=5.96 Hz, 1 H), 3.51 (m, 2H), 2.90 (s, 3H).

HRMS (ESI) [M+H]+ calc. for C18H20ClFN4O5 426.11, found: 427.14 [M+H]+

LCMS (GTJC-013-63-P2) m/z 427.1 [M+H]+ (ES+), 90.74% at 4.22 min.

1H NMR (400 MHz; DMSO-d6) (GTJC-013-63-P2, single β isomer): ☐ 8.74 (s, 1H), 7.73-7.75 (m, 1H), 7.68-7.71 (m, 1H), 7.47-7.52 (m, 1H), 7.31-7.34 (m, 1H), 7.13-7.17 (m, 1H), 7.09 (m, 1H), 5.59 (m, 1H), 5.38 (m, 1H), 5.22 (d, 1H, J1-2=8.84 Hz, α-H-1), 4.98 (m, 1H), 4.76 (m, 1H), 4.39 (m, 1H), 3.92-3.93 (m, 2H), 3.04 (m, 2H), 2.90 (s, 3H).

(S)-6-amino-2-(4-(((3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)(methyl)carbamoyl)-1H-1,2,3-triazol-1-yl)hexanoic acid (GTJC-057):

To a solution of N-((3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methylpropiolamide (100 mg 0.2564 mmol) in Toluene (5 mL), was added DIPEA (66.15 mg, 0.5128 mmol), CuI (48.50 mg, 0.2564 mmol) and (S)-3-azido-7-((tert-butoxycarbonyl)amino)-2-oxoheptanoic acid (92.7 mg, 0.3076 mmol) at 0° C. The reaction mixture was stirred at room temperature. After 12 h, the reaction mixture was quenched with in HCl (5 mL) then stirred for 30 minutes. Organic compound from the separated aqueous layer was extracted with 5% MeOH in DCM (3×25 mL). The combined organic layers were washed with brine and dried over anhydrous Na2SO4. The solvent was removed under reduced pressure at 45° C. temperature to afford the title compound as a white solid (GTJC-057, single β isomer, 15 mg, 5.2%).

HRMS (ESI) [M+H]+ calc. for C24H31FN8O7 562.23, found: 563.38 [M+H]+

LCMS: m/z 563.3 (M+H)+ (ES+) 98.41% at 3.13 min.

1H NMR (400 MHz; DMSO-d6, single β isomer): ☐ 8.77 (s, 1H), 8.42 (m, 1H), 7.68-7.75 (m, 2H), 7.38-7.57 (m, 1H), 7.12-7.16 (t, J=8.42 Hz, 1H), 5.72 (d, 1H, J1-2=7.8 Hz, α-H-1), 5.64 (m, 1H), 5.25-5.35 (m, 1H), 4.61-4.70 (m, 1H), 4.51 (bs, 1H), 3.93 (m, 1H), 3.71 (m, 1H), 3.54 (m, 2H), 3.31-3.35 (m, 2H), 3.26-3.31 (m, 2H), 3.05 (s, 2H), 2.78 (m, 1H), 2.49-2.54 (m, 2H), 2.44 (s, 1H), 2.13-2.24 (m, 1H), 1.55-1.59 (m, 1 H), 1.29 (m, 1 H).

TABLE 1

Exemplary compounds with galectin-3 inhibition according to some embodiments

| Structures | Inventory Code |
| --- | --- |
| [Iminogalactose derivative structure] | G603<br>intermediate 1<br>Iminogalactose derivative |
| [Carbogalactose derivative structure] | G606<br>intermediate 2<br>Carbogalactose derivative |
| [Aminogalactose derivative structure] | G609<br>intermediate 3<br>Aminogalactose derivative |
| [Furoyl hydrazide galactose triazole structure] | G611 |

TABLE 1-continued

Exemplary compounds with galectin-3 inhibition according to some embodiments

| Structures | Inventory Code |
|---|---|
| *(structure)* | G610 |
| *(structure)* | G617 |
| *(structure)* | G620 |
| *(structure)* | G622 |
| *(structure)* | G628 |
| *(structure)* | G629 |

TABLE 1-continued

Exemplary compounds with galectin-3 inhibition according to some embodiments

| Structures | Inventory Code |
| --- | --- |
| 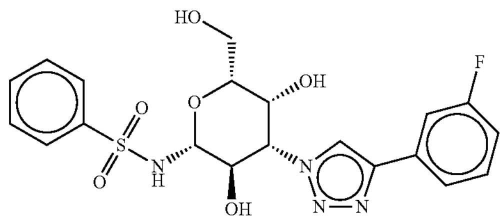 | G630 |
| GTJC-026 | G631 |
| 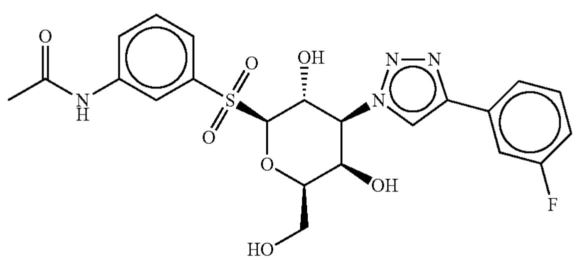 | G632 |
| 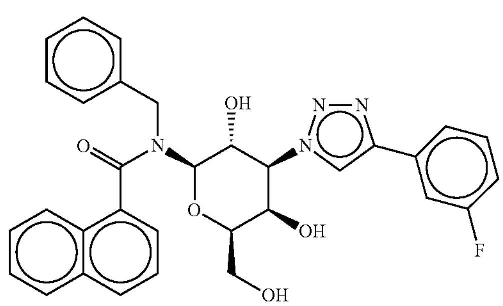 | G633 |
| 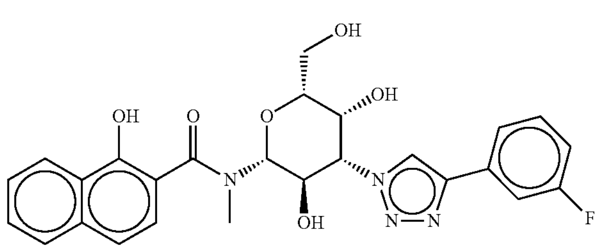 | G635 |

TABLE 1-continued

Exemplary compounds with galectin-3 inhibition according to some embodiments

| Structures | Inventory Code |
|---|---|
| 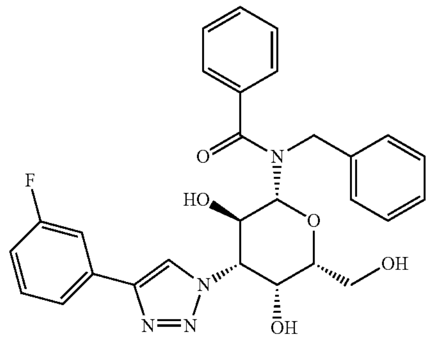 [SMILES: O=C(c1ccccc1)N(Cc1ccccc1)[C@@H]1O[C@H](CO)[C@H](O)[C@H](n2cc(-c3cccc(F)c3)nn2)[C@H]1O] | G639 |
| 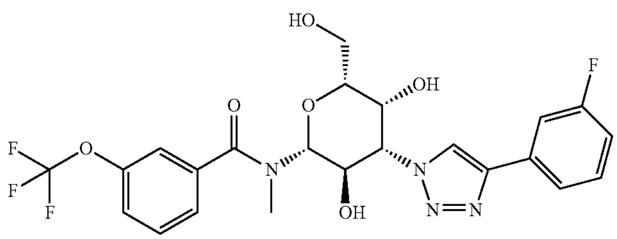 [SMILES: CN(C(=O)c1cccc(OC(F)(F)F)c1)[C@@H]1O[C@H](CO)[C@H](O)[C@H](n2cc(-c3cccc(F)c3)nn2)[C@H]1O] | G642 |
| 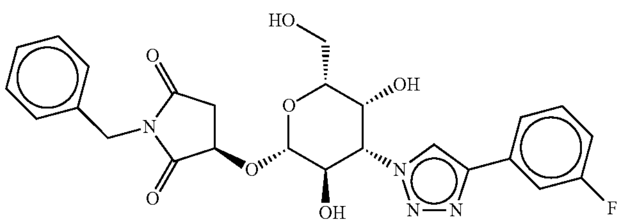 | G646 |
| 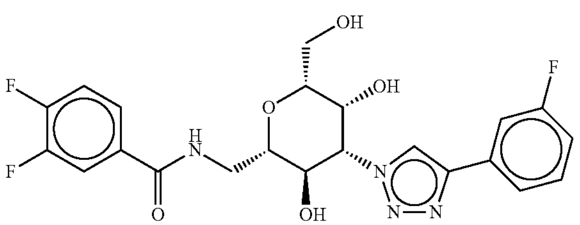 | G647 |
| 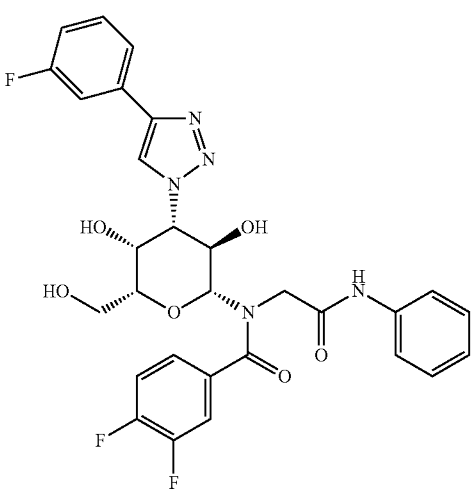 [SMILES: O=C(CN(C(=O)c1ccc(F)c(F)c1)[C@@H]1O[C@H](CO)[C@H](O)[C@H](n2cc(-c3cccc(F)c3)nn2)[C@H]1O)Nc1ccccc1] | G648 |

TABLE 1-continued

Exemplary compounds with galectin-3 inhibition according to some embodiments

| Structures | Inventory Code |
|---|---|
| 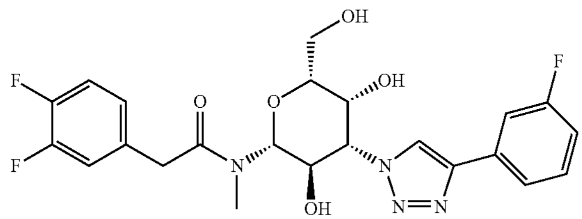 [SMILES: CN(C(=O)Cc1ccc(F)c(F)c1)[C@@H]1O[C@H](CO)[C@H](O)[C@H](n2cc(-c3cccc(F)c3)nn2)[C@H]1O] | G649 |
| 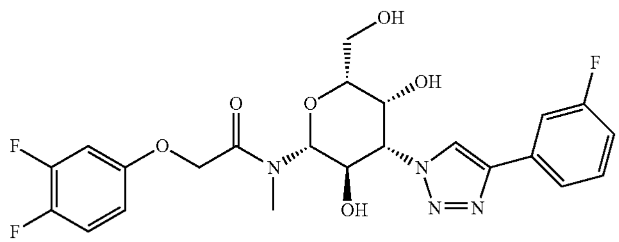 [SMILES: CN(C(=O)COc1ccc(F)c(F)c1)[C@@H]1O[C@H](CO)[C@H](O)[C@H](n2cc(-c3cccc(F)c3)nn2)[C@H]1O] | G651 |
| 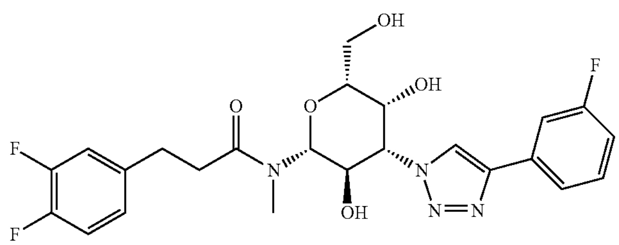 | GS-052 |
| 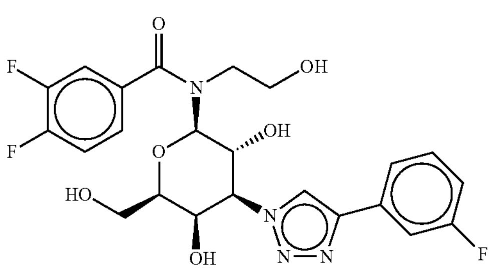 | G653 |
| 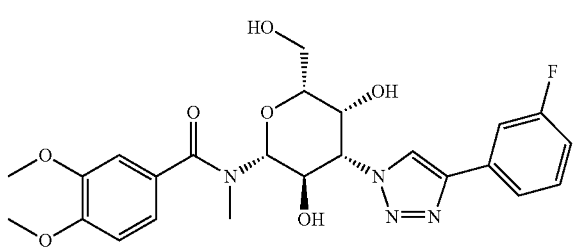 [SMILES: COc1ccc(C(=O)N(C)[C@@H]2O[C@H](CO)[C@H](O)[C@H](n3cc(-c4cccc(F)c4)nn3)[C@H]2O)cc1OC] | G655 |
| 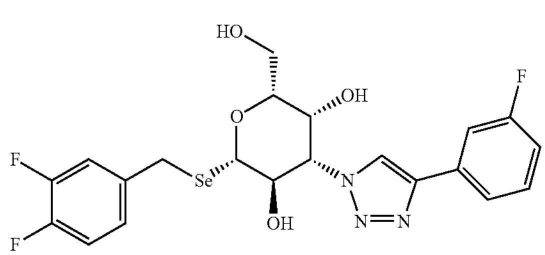 [SMILES: OC[C@H]1O[C@@H]([Se]Cc2ccc(F)c(F)c2)[C@H](O)[C@@H](n2cc(-c3cccc(F)c3)nn2)[C@H]1O] | G656 |

TABLE 1-continued
Exemplary compounds with galectin-3 inhibition according to some embodiments
| Structures | Inventory Code |
| --- | --- |
| 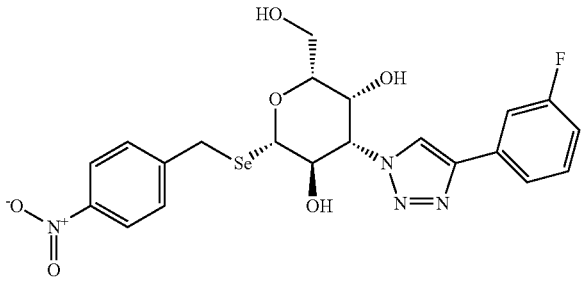 | G657 |
| 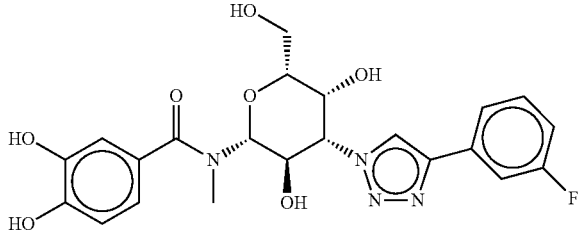 | G658 |
| 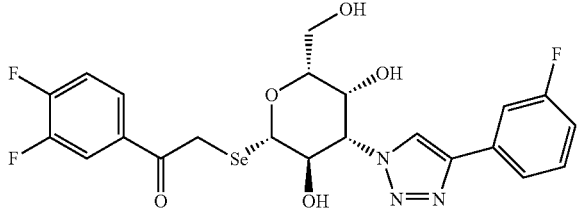 [SMILES: O=C(C[Se][C@@H]1O[C@H](CO)[C@H](O)[C@H](n2cc(-c3cccc(F)c3)nn2)[C@H]1O)c1ccc(F)c(F)c1] | G662 |
| 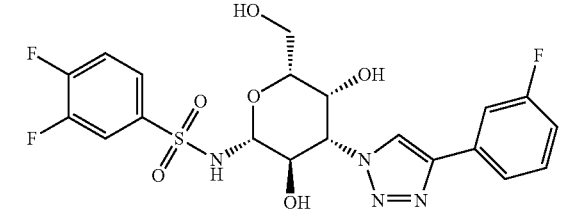 [SMILES: O=S(=O)(N[C@@H]1O[C@H](CO)[C@H](O)[C@H](n2cc(-c3cccc(F)c3)nn2)[C@H]1O)c1ccc(F)c(F)c1] | G666 |
| 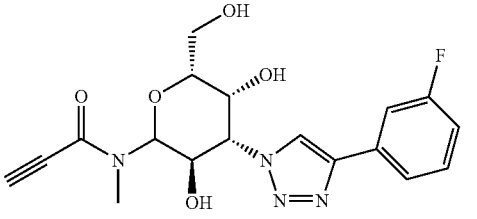 [SMILES: C#CC(=O)N(C)C1O[C@H](CO)[C@H](O)[C@H](n2cc(-c3cccc(F)c3)nn2)[C@H]1O] | G667 |
| 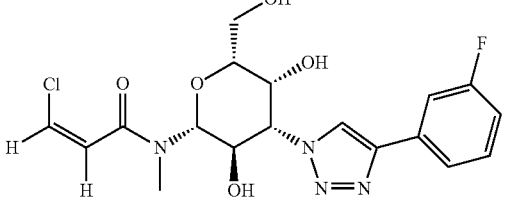 | G668 |

TABLE 1-continued

Exemplary compounds with galectin-3 inhibition according to some embodiments

| Structures | Inventory Code |
| --- | --- |
| 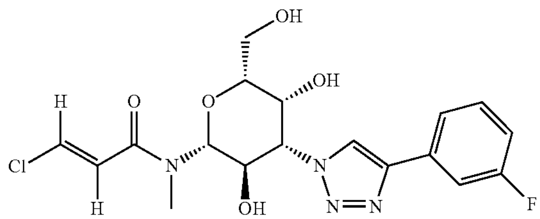 [SMILES: CN(C(=O)/C=C/Cl)[C@@H]1O[C@H](CO)[C@H](O)[C@H](n2cc(-c3cccc(F)c3)nn2)[C@H]1O] | G669 |
| 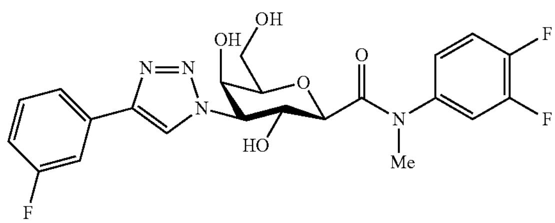 | G678 |
| 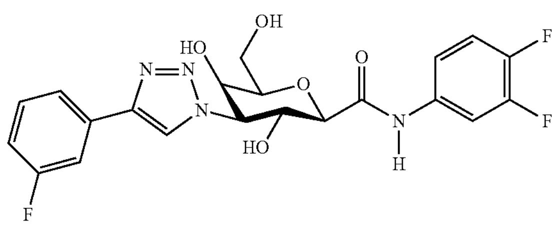 | G679 |
| 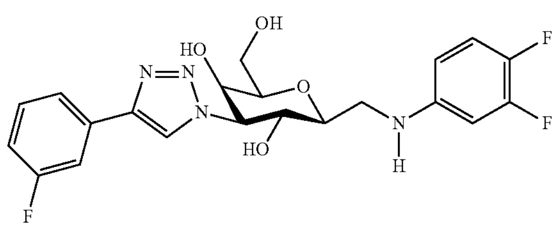 | G680 |
| 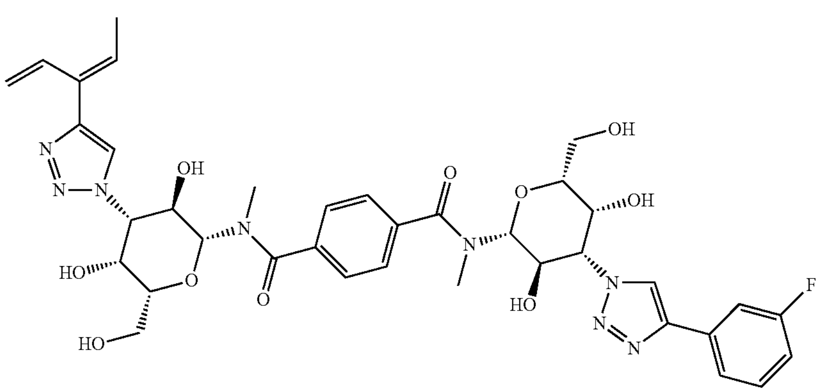 [SMILES: C=C/C(=C\C)c1cn([C@@H]2[C@@H](O)[C@H](N(C)C(=O)c3ccc(C(=O)N(C)[C@@H]4O[C@H](CO)[C@H](O)[C@H](n5cc(-c6cccc(F)c6)nn5)[C@H]4O)cc3)O[C@H](CO)[C@@H]2O)nn1] | G637 |

The invention claimed is:
1. A compound or a pharmaceutically acceptable salt or solvate thereof having the structure
| Structure |
|---|
| 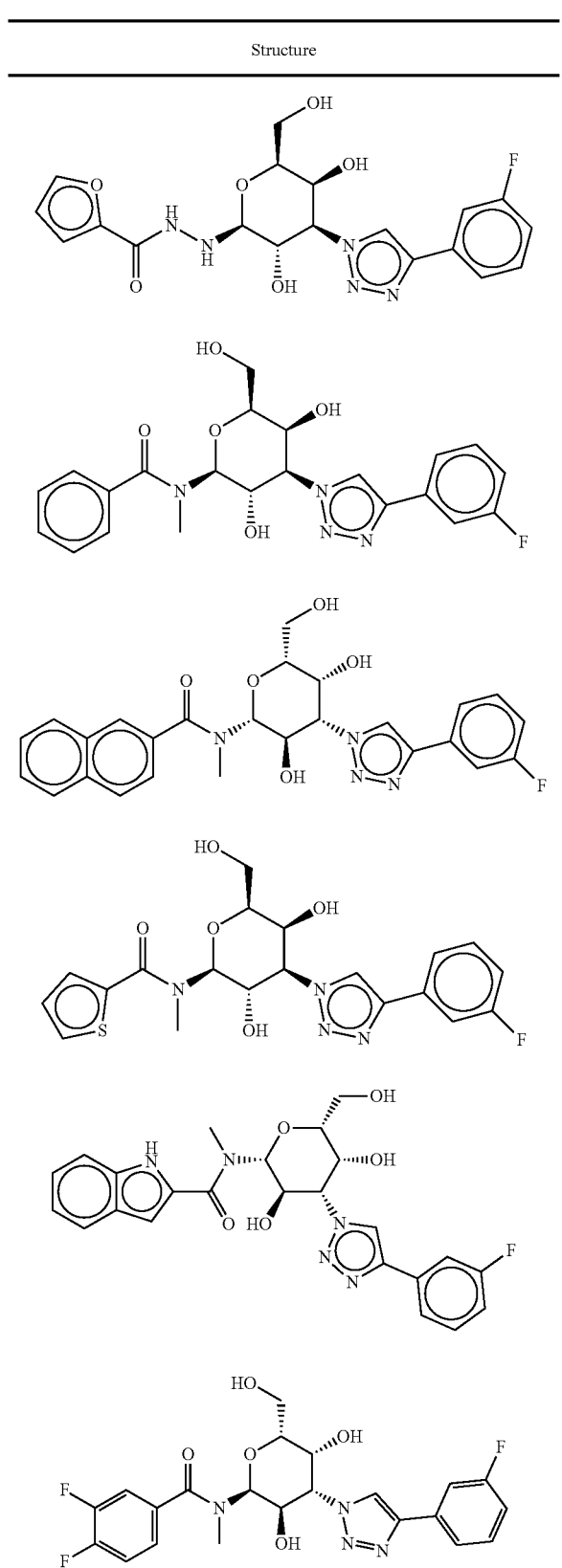 |
-continued
| Structure |
|---|
| 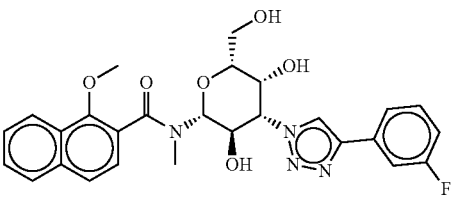 |
| 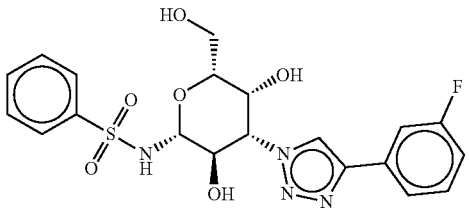 |
| 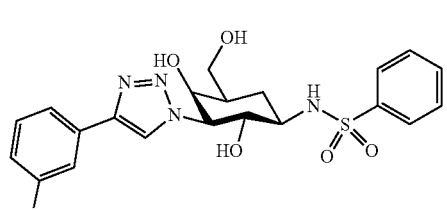 |
| 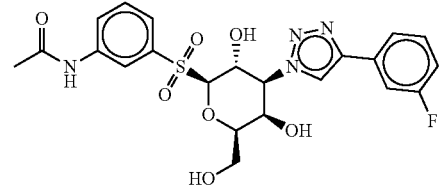 |
| 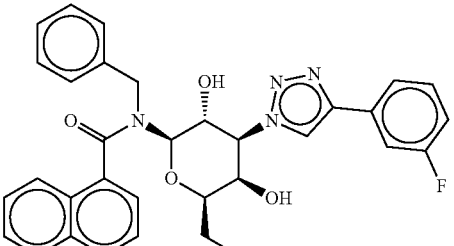 |
| 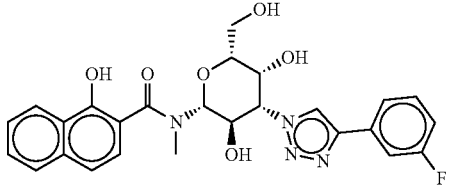 |

| 81 -continued | 82 -continued |
|---|---|
| Structure | Structure |
| 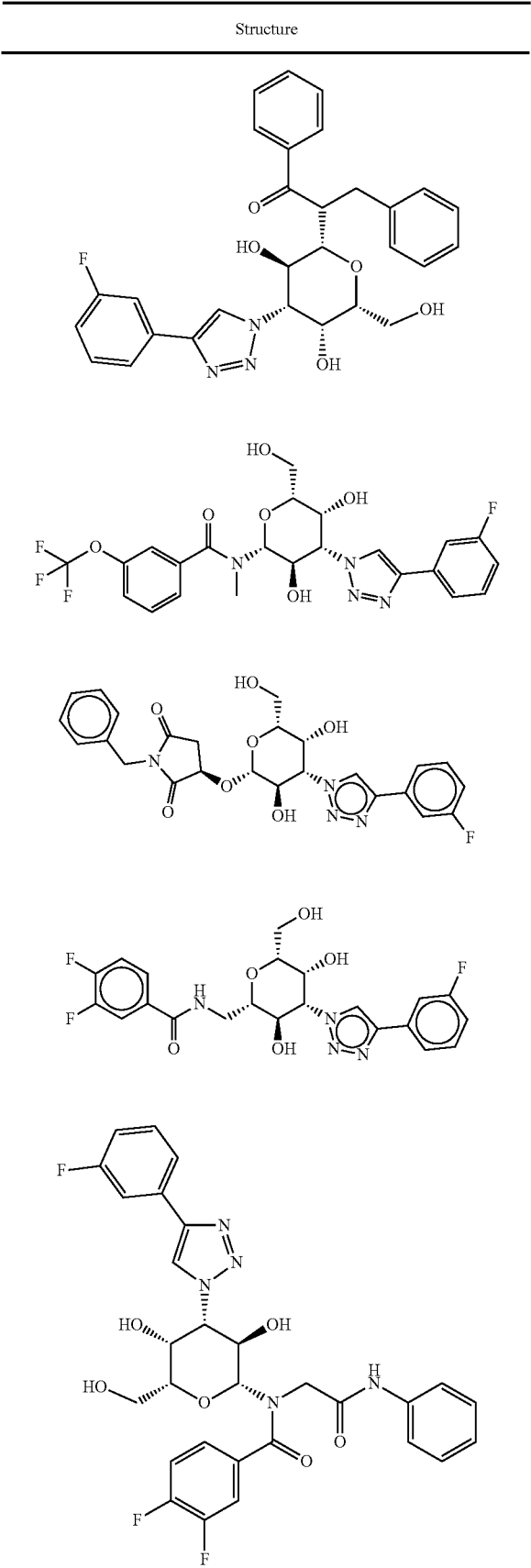 | 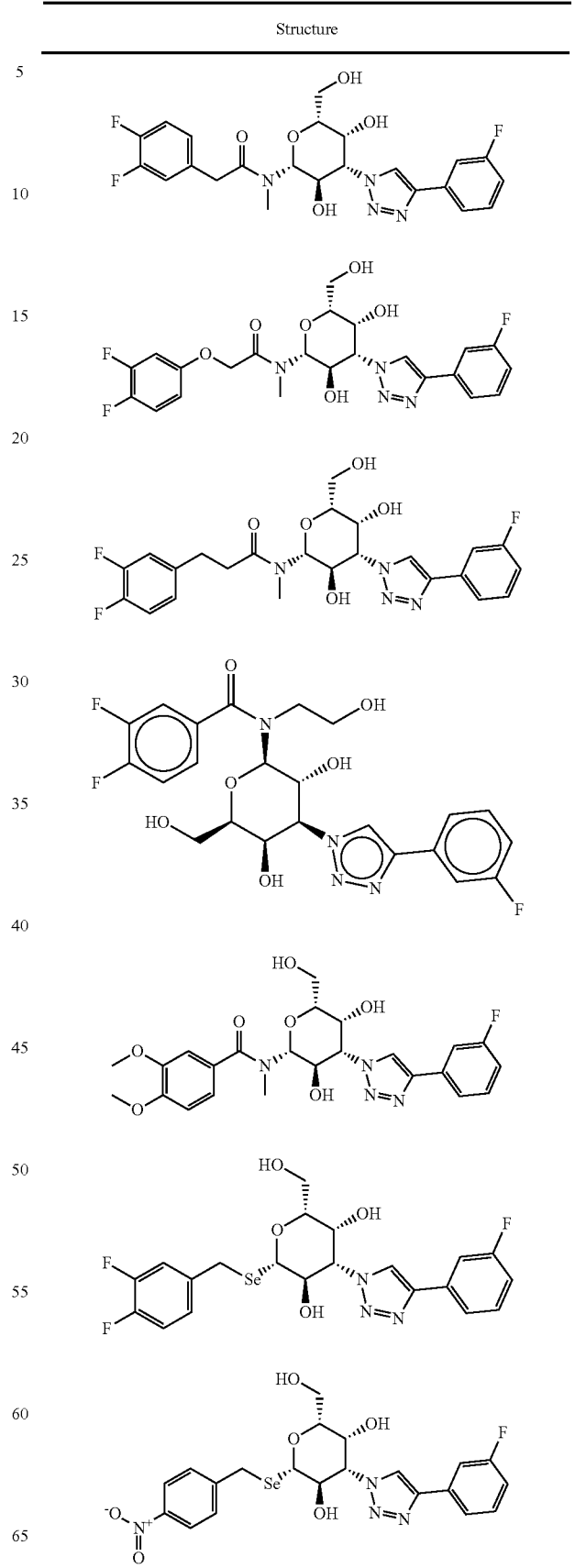 |

| Structure | | Structure |
|---|---|---|
| 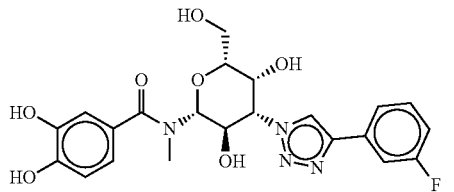 | 5 | 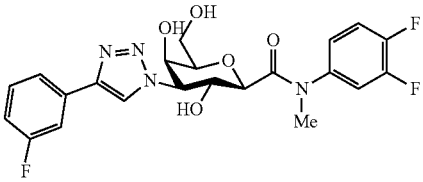 |
| 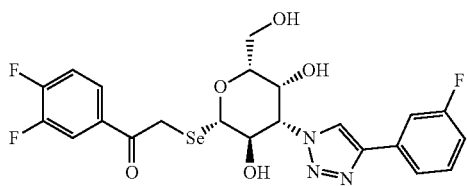 [SMILES: O=C(C[Se][C@@H]1O[C@H](CO)[C@H](O)[C@H](n2cc(-c3cccc(F)c3)nn2)[C@H]1O)c1ccc(F)c(F)c1] | 10, 15 | 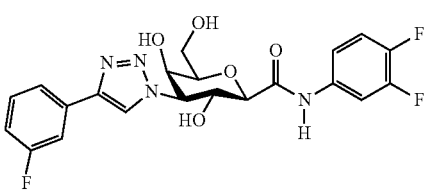 |
| 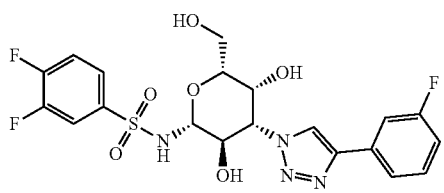 [SMILES: O=S(=O)(N[C@@H]1O[C@H](CO)[C@H](O)[C@H](n2cc(-c3cccc(F)c3)nn2)[C@H]1O)c1ccc(F)c(F)c1] | 20, 25 | 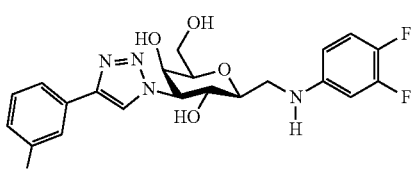 |
| 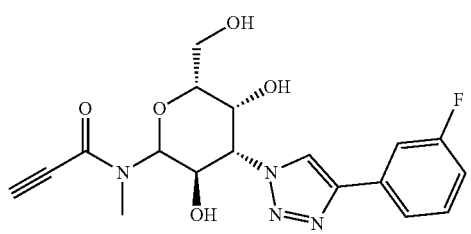 [SMILES: C#CC(=O)N(C)C1O[C@H](CO)[C@H](O)[C@H](n2cc(-c3cccc(F)c3)nn2)[C@H]1O] | 30, 35 | 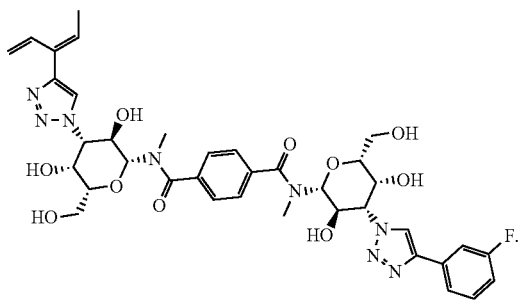 |
| 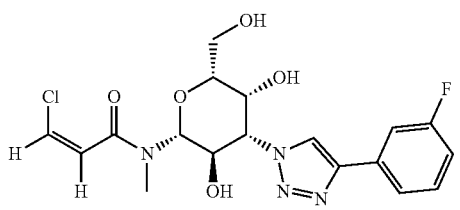 [SMILES: CN(C(=O)/C=C\Cl)[C@@H]1O[C@H](CO)[C@H](O)[C@H](n2cc(-c3cccc(F)c3)nn2)[C@H]1O] | | |
| 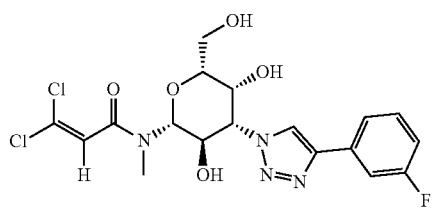 [SMILES: CN(C(=O)C=C(Cl)Cl)[C@@H]1O[C@H](CO)[C@H](O)[C@H](n2cc(-c3cccc(F)c3)nn2)[C@H]1O] | | |

2. The compound of claim 1, wherein the compound has an affinity of about 1 nM to about 50 µM for Galectin-3.

3. A composition comprising a therapeutically effective amount of the compound of claim 1 and a pharmaceutically acceptable adjuvant, excipient, formulation carrier or combinations thereof.

4. A composition comprising a therapeutically effective amount of the compound claim 1 and a therapeutically effective amount of an anti-inflammatory drug, vitamin, pharmaceutical drug, nutraceutical drug, supplement, or combinations thereof.

* * * * *